(12) United States Patent
Arnold et al.

(10) Patent No.: US 7,829,558 B2
(45) Date of Patent: Nov. 9, 2010

(54) FUSED RING HETEROCYCLE KINASE MODULATORS

(75) Inventors: William D. Arnold, San Diego, CA (US); Andreas Gosberg, San Diego, CA (US); Zhe Li, San Diego, CA (US); Ruo W. Steensma, San Diego, CA (US); Mark E. Wilson, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 136 days.

(21) Appl. No.: 12/235,426

(22) Filed: Sep. 22, 2008

(65) Prior Publication Data

US 2009/0203687 A1 Aug. 13, 2009

Related U.S. Application Data

(62) Division of application No. 11/192,318, filed on Jul. 27, 2005, now Pat. No. 7,452,993.

(60) Provisional application No. 60/591,778, filed on Jul. 27, 2004, provisional application No. 60/680,091, filed on May 11, 2005, provisional application No. 60/591,886, filed on Jul. 27, 2004.

(51) Int. Cl.
  A61K 31/5377 (2006.01)
  A61K 31/437 (2006.01)
  A61K 31/496 (2006.01)
  A61P 35/00 (2006.01)
(52) U.S. Cl. ............... 514/234.2; 514/303; 514/253.04
(58) Field of Classification Search ............. 514/234.2, 514/253.04, 303
  See application file for complete search history.

(56) References Cited

U.S. PATENT DOCUMENTS

| | | | |
|---|---|---|---|
| 5,019,586 | A | 5/1991 | Oxford et al. |
| 5,051,412 | A | 9/1991 | Macor |
| 5,338,849 | A | 8/1994 | Festal et al. |
| 5,563,150 | A | 10/1996 | Curtis et al. |
| 5,643,734 | A | 7/1997 | Henderson |
| 5,681,959 | A | 10/1997 | Bishop et al. |
| 6,335,342 | B1 | 1/2002 | Longo et al. |
| 6,589,950 | B1 | 7/2003 | Collingwood et al. |
| 6,699,883 | B1 | 3/2004 | Doeming et al. |
| 7,186,716 | B2 | 3/2007 | Wei et al. |
| 7,361,763 | B2 | 4/2008 | Arnold et al. |
| 2002/0119982 | A1 | 8/2002 | Wang et al. |
| 2004/0019052 | A1 | 1/2004 | Garland et al. |
| 2006/0035898 | A1 | 2/2006 | Arnold et al. |
| 2007/0043068 | A1 | 2/2007 | Arnold et al. |

FOREIGN PATENT DOCUMENTS

| | | |
|---|---|---|
| DE | 10053122 A1 | 5/2001 |
| DE | 199559122 A1 | 6/2001 |
| WO | WO-96-32391 A1 | 10/1996 |
| WO | WO-00-24694 A1 | 5/2000 |
| WO | WO-00-43393 A1 | 7/2000 |
| WO | WO-00-71537 A1 | 11/2000 |
| WO | WO-02-24694 A1 | 3/2002 |
| WO | WO-02-051837 A2 | 7/2002 |
| WO | WO-03-002563 A1 | 1/2003 |
| WO | WO-03-024969 A1 | 3/2003 |
| WO | WO-03-028724 A1 | 4/2003 |
| WO | 03/045949 * | 6/2003 |
| WO | WO-03-045949 A1 | 6/2003 |
| WO | WO-03-068221 A1 | 8/2003 |
| WO | WO-03-068773 A1 | 8/2003 |
| WO | WO-03-082868 A1 | 10/2003 |
| WO | WO-03-082869 A1 | 10/2003 |
| WO | WO-03-087816 A1 | 10/2003 |
| WO | WO-2004-014368 A1 | 2/2004 |
| WO | WO-2004-024895 | 3/2004 |
| WO | WO-2004-032874 A2 | 4/2004 |
| WO | WO-2004-078756 A2 | 9/2004 |
| WO | WO-2004-078757 A2 | 9/2004 |
| WO | WO-2004-101565 A1 | 11/2004 |
| WO | WO-2004-101565 A2 | 11/2004 |
| WO | WO-2005-028475 A2 | 3/2005 |
| WO | WO-2005-062795 A2 | 7/2005 |
| WO | WO-2005-085244 A1 | 9/2005 |
| WO | WO-2005-095400 A1 | 10/2005 |
| WO | WO-2006-124863 | 11/2006 |

OTHER PUBLICATIONS

Milella et al., Reviews in clinical and experimental hematology, (Jun. 2003) vol. 7, No. 2, pp. 160-190.*
Adamczyk, M. et al., "Synthesis of 3,7-dihydro-imidazo[1,2a]pyrazine-3-ones and their chemiluminescent properties," Tetrahedron 59:8129-8142 (2003).
Altschul et al., "Gapped BLAST and PSI-BLAST: a new generation of protein database search programs," Nuc. Acids Rec. 25(17):3389-3402 (1997).
Bach, T. et al., "Synthesis of 2'-Substituted 4-Bromo-2,4'-bithiazoles by Regioselective Cross-Coupling Reactions," J. Org. Chem. 67:5789-5795 (2002).
Berge et al., "Pharmaceutical Salts," J. Pharma. Sci. 66:1-19 (1977).
Blaney, J.M. and Dixon, J.S., "A good ligand is hard to find: Automated docking methods," Perspectives in Drug Discovery and Design 1:301-319 (1993).
Bolm, C. et al., "Iron-Catalyzed Reactions in Organic Synthesis," Chem. Rev. 104:6217-6254 (2004).
Boudier, A. et al., "New Applications of Polyfunctional Organometallic Compounds in Organic Synthesis," Angew. Chem. Int. Ed. 39:4414-4435 (2000).

(Continued)

Primary Examiner—D. Margaret Seaman
Assistant Examiner—Niloofar Rahmani
(74) Attorney, Agent, or Firm—Wilson Sonsini Goodrich & Rosati

(57) ABSTRACT

The present invention provides novel fused ring heterocycle kinase modulators and methods of using the novel fused ring heterocycle kinase modulators to treat diseases mediated by kinase activity.

35 Claims, 1 Drawing Sheet

OTHER PUBLICATIONS

Brooks et al., "CHARMM: A Program for Macromolecular Energy, Minimization, and Dynamics Calculations," J. Comp. Chem. 4(2):187-217 (1983).

Charifson, P.S. et al., "Consensus Scoring: A Method for Obtaining Improved Hit Rates from Docking Databases of Three-Dimensional Structures into Proteins," J. Med. Chem. 42:5100-5109 (1999).

Christman, U. and Villar, R., "Monoligated Palladium Species as Cataylists in Cross-Coupling Reactions," Angew. Chem. 117:370-378 (2005).

Crabtree, S. and Cronan, J.E., "Facile and Gentle Method for Quantitative Lysis of *Escherichia coli* and *Salmonella typhimurium*," J. Bacteriol. 158(1):354-356 (1984).

Feldman et al., "Novel Small Molecule Inhibitors of 3-Phosphoinositide-Dependent Kinase-1 (PDK1)," JBC Papers In Press Published Mar. 16, 2005 as manuscript M501367200.

Fuerstner, A. et al., "Iron-Catalyzed Cross-Coupling Reactions," J. Am. Chem. Soc. 124:13856-13863 (2002).

Goodsell and Olsen: "Automated Docking of Substrates to Proteins by Simulated Annealing," Proteins: Structure, Function and Genetics 8:195-202 (1990).

Goulet et al., "ESPript: analysis of multiple sequence alignments in PostScript," Bioinformatics 15(4):305-308 (1999).

Harrington et al., "VX-680, a potent and selective small-molecule inhibitor of the Aurora kinases, suppresses tumor growth in vivo," Nature Medic ine Advance Online Publication Published online Feb. 22, 2004.

Hartwig, J.F., "Carbon-Heteroatom Bond-Forming Reductive Eliminations of Amines, Ethers, and Sulfides," Acc. Chem. Res. 31:852-860 (1998).

Ishiyama, T. et al., "Palladium(0)-Catalyzed Cross-Coupling Reaction of Alkoxydiboron with Haloarenes: A Direct Procedure for Arylboronic Esters," J. Org. Chem. 60:7508-7510 (1995).

Ji, J. et al., "Selective Amination of Polyhalopyridines Catalyzed by a Palladium-Xanthphos Complex," Org. Lett. 5:4611-4614 (2003).

Jones et al., "Molecular Recognition of Receptor Sites using a Genetic Algorithm with a Description of Desolvation," J. Mol. Biol. 245:43-53 (1995).

Kuntz et al., "A Geometric Approach to Macromolecule-Ligand Interactions," J. Mol. Biol. 161:269-288 (1982).

Ley, S. et al., "Modern Synthetic: Methods for Copper-Mediated C(Aryl)-O-, C(Aryl)-N- und C(Aryl)-S Bond Formation," Angew. Chem. 115:5558-5607 (2003).

Littke, A.F., and Fu, G., "Palladium-Catalyzed Coupling Reactions of Aryl Chlorides," Angew.Chem. 114:4177-4211 (2002).

Maryanoff, B.E. and Reitz, A.B., "The Wittig Olefination Reaction and Modifications Involving Phosphoryl-Stabilized Carbanions. Stereochemistry, Mechanism, and Selected Synthetic Aspects," Chem. Rev. 89:863-927 (1989).

Matsui, T. et al., "Expression of Unphosphorylated Form of Human Double-Stranded RNA-Activated Protein Kinase in *Escherichia coli*," Biochem. Biophys. Res. Commun. 284:798-807 (2001).

Meng et al., "Automated Docking with Grid-Based Energy Evaluation," J. Comp. Chem. 13(4):505-524 (1992).

Mongin et al., "Advances in the directed metallation of azines and diazines (pyridines, pyrimidines, pyrazines, pyridazines, quinolines, benzodiazines, and carbolines). Part 1. Metallation of pyridines, quinolines anc carbolines," Tetrahedron 57:4059-4090 (2001).

Nahm, S. and Weinreb, S.M., "N-Methoxy-N-Methylamides as Effective Acylating Agents," Tetrahedron Lett. 22(39):3815-3818 (1981).

Navarro, O. et al., "Cross-Coupling and Dehalogenation Reactions Catalyzed by (N-Heterocyclic carbene)Pd(allyl)Cl Complexes," J. Org. Chem. 69:3173-3180 (2004).

PCT/US08/65150 Search Report dated Aug. 21, 2008.

Rarey, M. et al., "A Fast Flexible Docking Method using an Incremental Construction Algorithm," J. Mol. Biol. 261:470-489 (1996).

Sakamoto et al., "Condensed Heteroaromatic Ring Systems. XXII. Simple and General Synthesis of 1$H$-Pyrrolo-Pyridines," Heterocycles 34(12):2379-2384 (1992).

Sapountzis, I. et al., "A New General Preparation of Polyfunctional Diarylamines by the Addition of Functionalized Arylmagnesium Compounds to Nitroarenes," J. Am. Chem. Soc. 124:9390-9391 (2002).

Thompson et al., "DbClustal: rapid and reliable global multiple alignments of protein sequences detected by database searches," Nucl. Acids Res. 28(15):2919-2926 (2000).

Travis, "Proteins and Organic Solvents Make an Eye-Opening Mix," Science 262:1374 (1993).

Turck, A. et al., "Advances in the directed metallation of azines and diazines (pyridines, pyrimidines, pyrazines, pyridazines, quinolines, benzodiazines and carbolines). Part 2. Metallation of pyrimidines, pyrazines, pyridazines and benzodiazines," Tetrahedron 57:4489-4505 (2001).

Vilar, R., Christman, U.—Angew. Chem. 117:370(2005).

Weiner et al., "A New Force Field for Molecular Mechanical Simulation of Nucelic Acids and Proteins," J. Am. Chem. Soc. 106:765-784 (1984).

Wolfe, J. et al., "Rational Development of Practical Catalysts for Aromatic Carbon—Nitrogen Bond Formation," Acc. Chem. Res. 31:805-818 (1998).

Zhang et al., "A Simple Statistical Parameter for Use in Evaluation and Validation of High Throughput Screening Assays," J. Biomol. Screening 4(2):67-73 (1999).

Witherington et al., "5-Aryl-pyrazolo[3,4-b]pyridines: Potent Inhibitors of Glycogen Synthase Kinase-3 (GSK-3)," Bioorg. Med. Chem. Ltrs. 13:1577-1580 (2003).

PCT/US08/59965 Search Report dated Jul. 22, 2008.

* cited by examiner

Figure 1

MLEICLKLVGCKSKKGLSSSSSCYLEEALQRPVASDFEPQGLSEAARWNS
1                                                                                                                50
KENLLAGPSENDPNLFVALYDFVASGDNTLSITKGEKLRVLGYNHNGEWC
51                                                                                                              100
EAQTKNGQGWVPSNYITPVNSLEKHSWYHGPVSRNAAEYLLSSGINGSFL
101                                                                                                            150
VRESESSPGQRSISLRYEGRVYHYRINTASDGKLYVSSESRFNTLAELVH
151                                                                                                            200
HHSTVADGLITTLHYPAPKRNKPTVYGVSPNYDKWEMERTDITMKHKLGG
201                                                                                                            250
GQYGEVYEGVWKKYSLTVAVKTLKEDTMEVEEFLKEAAVMKEIKHPNLVQ
251                                                                                                            300
LLGVCTREPPFYIITEFMTYGNLLDYLRECNRQEVNAVVLLYMATQISSA
301                                                                                                            350
MEYLEKKNFIHRDLAARNCLVGENHLVKVADFGLSRLMTGDTYTAHAGAK
351                                                                                                            400
FPIKWTAPESLAYNKFSIKSDVWAFGVLLWEIATYGMSPYPGIDLSQVYE
401                                                                                                            450
LLEKDYRMERPEGCPEKVYELMRACWQWNPSDRPSFAEIHQAFETMFQES
451                                                                                                            500
SISDEVEKELGKQGVRGAVSTLLQAPELPTKTRTSRRAAEHRDTTDVPEM
501                                                                                                            550
PHSKGQGESDPLDHEPAVSPLLPRKERGPPEGGLNEDERLLPKDKKTNLF
551                                                                                                            600
SALIKKKKKTAPTPPKRSSSFREMDGQPERRGAGEEEGRDISNGALAFTP
601                                                                                                            650
LDTADPAKSPKPSNGAGVPNGALRESGGSGFRSPHLWKKSSTLTSSRLAT
651                                                                                                            700
GEEEGGGSSSKRFLRSCSASCVPHGAKDTEWRSVTLPRDLQSTGRQFDSS
701                                                                                                            750
TFGGHKSEKPALPRKRAGENRSDQVTRGTVTPPPRLVKKNEEAADEVFKD
751                                                                                                            800
IMESSPGSSPPNLTPKPLRRQVTVAPASGLPHKEEAEKGSALGTPAAAEP
801                                                                                                            850
VTPTSKAGSGAPGGTSKGPAEESRVRRHKHSSESPGRDKGKLSRLKPAPP
851                                                                                                            900
PPPAASAGKAGGKPSQSPSQEAAGEAVLGAKTKATSLVDAVNSDAAKPSQ
901                                                                                                            950
PGEGLKKPVLPATPKPQSAKPSGTPISPAPVPSTLPSASSALAGDQPSST
951                                                                                                           1000
AFIPLISTRVSLRKTRQPPERIASGAITKGVVLDSTEALCLAISRNSEQM
1001                                                                                                         1050
ASHSAVLEAGKNLYTFCVSYVDSIQQMRNKFAFREAINKLENNLRELQIC
1051                                                                                                         1100
PATAGSGPAATQDFSKLLSSVKEISDIVQR
1101                                                     1130

SEQUENCE LISTING

```
<160> NUMBER OF SEQ ID NOS: 24

<210> SEQ ID NO 1
<211> LENGTH: 1130
<212> TYPE: PRT
<213> ORGANISM: Homo sapiens

<400> SEQUENCE: 1

Met Leu Glu Ile Cys Leu Lys Leu Val Gly Cys Lys Ser Lys Lys Gly
1               5                   10                  15

Leu Ser Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45
```

-continued

```
Asn Ser Lys Glu Asn Leu Leu Ala Gly Pro Ser Glu Asn Asp Pro Asn
 50                  55                  60

Leu Phe Val Ala Leu Tyr Asp Phe Val Ala Ser Gly Asp Asn Thr Leu
 65                  70                  75                  80

Ser Ile Thr Lys Gly Glu Lys Leu Arg Val Leu Gly Tyr Asn His Asn
                 85                  90                  95

Gly Glu Trp Cys Glu Ala Gln Thr Lys Asn Gly Gln Gly Trp Val Pro
                100                 105                 110

Ser Asn Tyr Ile Thr Pro Val Asn Ser Leu Glu Lys His Ser Trp Tyr
            115                 120                 125

His Gly Pro Val Ser Arg Asn Ala Ala Glu Tyr Leu Leu Ser Ser Gly
130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
            420                 425                 430

Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
450                 455                 460
```

-continued

```
Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
            485                 490                 495

Phe Gln Glu Ser Ser Ile Ser Asp Glu Val Lys Glu Leu Gly Lys
        500                 505                 510

Gln Gly Val Arg Gly Ala Val Ser Thr Leu Leu Gln Ala Pro Glu Leu
        515                 520                 525

Pro Thr Lys Thr Arg Thr Ser Arg Arg Ala Ala Glu His Arg Asp Thr
    530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
        595                 600                 605

Lys Thr Ala Pro Thr Pro Pro Lys Arg Ser Ser Ser Phe Arg Glu Met
    610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
    690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
    770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Glu Lys Gly Ser Ala Leu Gly Thr Pro Ala Ala Ala
        835                 840                 845

Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880
```

```
Ser Ser Glu Ser Pro Gly Arg Asp Lys Gly Lys Leu Ser Arg Leu Lys
            885                 890                 895

Pro Ala Pro Pro Pro Ala Ala Ser Ala Gly Lys Ala Gly Gly
            900                 905                 910

Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
            930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
            965                 970                 975

Ser Pro Ala Pro Val Pro Ser Thr Leu Pro Ser Ala Ser Ser Ala Leu
            980                 985                 990

Ala Gly Asp Gln Pro Ser Ser Thr Ala Phe Ile Pro Leu Ile Ser Thr
            995                 1000                1005

Arg Val Ser Leu Arg Lys Thr Arg Gln Pro Pro Glu Arg Ile Ala
            1010                1015                1020

Ser Gly Ala Ile Thr Lys Gly Val Val Leu Asp Ser Thr Glu Ala
            1025                1030                1035

Leu Cys Leu Ala Ile Ser Arg Asn Ser Glu Gln Met Ala Ser His
            1040                1045                1050

Ser Ala Val Leu Glu Ala Gly Lys Asn Leu Tyr Thr Phe Cys Val
            1055                1060                1065

Ser Tyr Val Asp Ser Ile Gln Gln Met Arg Asn Lys Phe Ala Phe
            1070                1075                1080

Arg Glu Ala Ile Asn Lys Leu Glu Asn Asn Leu Arg Glu Leu Gln
            1085                1090                1095

Ile Cys Pro Ala Thr Ala Gly Ser Gly Pro Ala Ala Thr Gln Asp
            1100                1105                1110

Phe Ser Lys Leu Leu Ser Ser Val Lys Glu Ile Ser Asp Ile Val
            1115                1120                1125

Gln Arg
            1130

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ala Ile Tyr Ala Ala Pro Phe Ala Lys Lys Lys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Arg Arg Ala Ser Leu Gly
1               5
```

```
<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp Cys
        35

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcaaaaaaga ggcagtgggc tttg                                          24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgaatttgc tgtgatccag g                                             21

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cataatgggc catcatcatc atcatcacgg tggtcatatg tccctt                  46

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 aaggggatc ctaaactgca gagatcc                                        27

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 9
aaggaggaga tatacataat gggccatcat catcatcatc acggtggtca tatgtccctt    60

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 aaggggatc ctaaactgca gagatcc                                          27

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gly His His His His His His Gly Gly His Met Ser Leu
1               5                   10

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Gly Gly Ser
1

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcagagatcc gaattcgagc tccgtcgacg gatggagtga agagatgcg c               51

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtggtggtg ctcgagtgcg gccgcaagct ttcatcatgc gccttctccc tgtac          55

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 15
gacaagtggg aaatggagc                                                    19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcctcgttt ccccagctc                                                    19

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catatgtccc tt                                                           12

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aagggcatca tcaccatcac cactgatcc                                         29

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaggaggaga tatacatatg tccctt                                            26

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagggcatca tcaccatcac cactgatcc                                         29

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 21

Glu Gly His His His His His
1               5

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccaccattct acataatcat tgagttcatg acctatggg                              39

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cccataggtc atgaactcaa tgattatgta gaatggtgg                              39

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
1               5
```

FUSED RING HETEROCYCLE KINASE MODULATORS

CROSS-REFERENCES TO RELATED APPLICATIONS

This application is a divisional patent application of U.S. patent application Ser. No. 11/192,318, filed Jul. 27, 2005, now U.S. Pat. No. 7,452,993 and to which application we claim priority under 35 U.S.C. §121, and claims the benefit of U.S. Provisional Patent Application No. 60/591,778, filed Jul. 27, 2004, U.S. Provisional Patent Application No. 60/680, 091, filed May 11, 2005, and U.S. Provisional Patent Application No. 60/591,886, filed Jul. 27, 2004. The disclosures of each of these applications are incorporated herein by reference in their entirety for all purposes.

BACKGROUND OF THE INVENTION

Mammalian protein kinases are important regulators of cellular functions. Because dysfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: *Listeria* invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

The Aurora family of serine/threonine kinases is essential for mitotic progression. Expression and activity of the Aurora kinases are tightly regulated during the cell cycle. A variety of proteins having roles in cell division have been identified as Aurora kinase substrates. Based on the known function of the Aurora kinases, inhibition of their activity is believed to disrupt the cell cycle and block proliferation and therefore tumor cell viability. Harrington et al., *Nature Medicine*, advanced publication online (2004).

3-Phosphoinositide-dependent kinase 1 (PDK1) is a Ser/Thr protein kinase that can phosphorylate and activate a number of kinases in the AGC kinase super family, including Akt/PKB, protein kinase C (PKC), PKC-related kinases (PRK1 and PRK2), p70 ribobsomal S6-kinase (S6K1), and serum and glucocorticoid-regulated kinase (SGK). The first identified PDK1 substrate is the proto-oncogene Akt. Numerous studies have found a high level of activated Akt in a large percentage (30-60%) of common tumor types, including melanoma and breast, lung, gastric, prostate, hematological and ovarian cancers. The PDK1/Akt signaling pathway thus represents an attractive target for the development of small molecule inhibitors that may be useful in the treatment of cancer. Feldman et al., *JBC* Papers in Press. Published on Mar. 16, 2005 as Manuscript M501367200.

Because kinases have been implicated in numerous diseases and conditions, such as cancer, there is a need to develop new and potent protein kinase inhibitors that can be used for treatment. The present invention fulfills these and other needs in the art. Although certain protein kinases are specifically named herein, the present invention is not limited to inhibitors of these kinases, and, includes, within its scope, inhibitors of related protein kinases, and inhibitors of homologous proteins.

BRIEF DESCRIPTION OF THE DRAWINGS

FIG. 1 shows the wild-type ABL numbering according to ABL exon Ia.

BRIEF SUMMARY OF THE INVENTION

It has been discovered that, surprisingly, fused ring heterocycle compounds of the present invention may be used to modulate kinase activity and to treat diseases mediated by kinase activity. These novel fused ring heterocycle kinase modulators are described in detail below. In addition, inhibitory activities of selected compounds are disclosed herein.

In one aspect, the present invention provides a fused ring heterocycle kinase modulator having the formula:

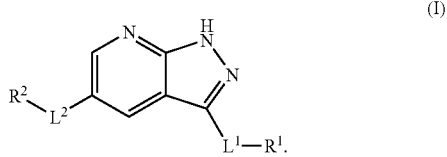

(I)

In Formula (I), $L^1$ and $L^2$ are independently a bond, —S($O)_n$—, —O—, —NH—, unsubstituted $C_1$-$C_5$ alkylene, or unsubstituted 2 to 5 membered heteroalkylene. The symbol n is an integer from 0 to 2. $R^1$ and $R^2$ are independently substituted or unsubstituted cycloalkyl, substituted or unsubstituted heterocycloalkyl, substituted or unsubstituted heteroaryl, or substituted or unsubstituted aryl. In some embodiments, $R^1$ is not substituted or unsubstituted pyrrolyl. In other embodiments, $L^1$ is not unsubstituted 2 to 5 membered heteroalkylene when $R^1$ and $R^2$ are both unsubstituted phenyl. In other embodiments, $L^1$ is not —S(O)$_2$— where $R^2$ is unsubstituted piperazinyl.

In another aspect, the present invention provides a fused ring heterocycle kinase modulator (also referred to herein as a "compound of the present invention") having the formula:

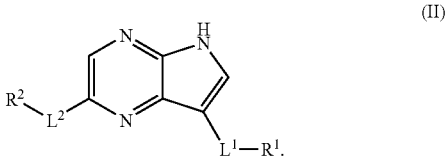

(II)

In Formula (II), $L^1$, $L^2$, $R^1$, and $R^2$ are as defined above in the discussion of Formula (I).

In another aspect, the present invention provides a fused ring heterocycle kinase modulator (also referred to herein as a "compound of the present invention") having the formula:

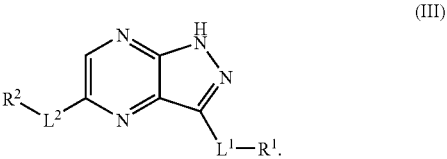

(III)

In Formula (III), $L^1$, $L^2$, $R^1$, and $R^2$ are as defined above in the discussion of Formula (I).

In another aspect, the present invention provides methods of modulating protein kinase activity using the fused ring heterocycle kinase modulators of the present invention. The method includes contacting the protein kinase with a fused ring heterocycle kinase modulator.

In another aspect, the present invention provides methods of treating a disease mediated by kinase activity (kinase-mediated disease or disorder) in a subject (e.g. mammals, such as humans) in need of such treatment. The method includes administering to the subject a therapeutically effective amount of a fused ring heterocycle kinase modulator of the present invention.

In another aspect, the present invention provides a pharmaceutical composition including a fused ring heterocycle kinase modulator in admixture with a pharmaceutically acceptable excipient.

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, —$CH_2CH=CHCH_2$—, —$CH_2C\equiv CCH_2$—, and —$CH_2CH_2CH(CH_2CH_2CH_3)CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, sulfur, and phosphorus atoms may optionally be oxidized and the nitrogen heteroatom may optionally be quaternized. The heteroatom(s)

O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR' R' or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl," and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO₂R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"', —S(O)R', —S(O)₂R', —S(O)₂NR'R", —NRSO₂R', —CN and —NO₂, —R', —N₃, —CH(Ph)₂, fluoro(C₁-C₄)alkoxo, and fluoro (C₁-C₄)alkyl, in a number ranging from zero to the total number of open valences on aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH₂)$_r$—B-, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)₂—, or —S(O)₂NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:
(A) —OH, —NH₂, —SH, —CN, —CF₃, —NO₂, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C₁-C₂₀ alkyl, each substituted or unsubstituted heteroalkyl is a substituted or unsubstituted 2 to 20 membered heteroalkyl, each substituted or unsubstituted cycloalkyl is a substituted or unsubstituted C₄-C₈ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C₁-C₈ alkyl, each substituted or unsubstituted heteroalkyl is a substituted or unsubstituted 2 to 8 membered heteroalkyl, each substituted or unsubstituted cycloalkyl is a substituted or unsubstituted C₅-C₇ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol ~~~ denotes the point of attachment of a moiety to the remainder of the molecule.

I. Fused Ring Heterocycle Kinase Modulators

In one aspect, the present invention provides a fused ring heterocycle kinase modulator (also referred to herein as a "compound of the present invention") having the formula:

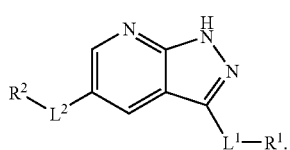

(I)

In Formula (I), $L^1$ and $L^2$ are independently a bond, —S(O)$_n$—, —O—, —NH—, substituted or unsubstituted $C_1$-$C_5$ alkylene, or substituted or unsubstituted 2 to 5 membered heteroalkylene. In some embodiments, $L^1$ and $L^2$ are independently a bond, —S(O)$_n$—, —O—, —NH—, unsubstituted $C_1$-$C_5$ alkylene, or unsubstituted 2 to 5 membered heteroalkylene. The symbol n is an integer from 0 to 2. $R^1$ and $R^2$ are independently substituted or unsubstituted cycloalkyl, substituted or unsubstituted heterocycloalkyl, substituted or unsubstituted heteroaryl, or substituted or unsubstituted aryl.

In some embodiments, $R^1$ is not substituted or unsubstituted pyrrolyl. In other embodiments, $L^1$ is not unsubstituted 2 to 5 membered heteroalkylene when $R^1$ and $R^2$ are both unsubstituted phenyl. In other embodiments, $L^1$ is not —S(O)$_2$— where $R^2$ is unsubstituted piperazinyl.

In some embodiments, $R^1$ is not substituted or unsubstituted 5-membered heteroaryl. In other embodiments $R^1$ is substituted or unsubstituted 6-membered heteroaryl, substituted or unsubstituted heterocycloalkyl, substituted or unsubstituted aryl, or substituted or unsubstituted heteroaryl. $R^1$ may also be a substituted or unsubstituted 6-membered heteroaryl, or substituted or unsubstituted aryl.

In other embodiments, $L^1$ is not unsubstituted 2 to 5 membered heteroalkylene when $R^1$ and $R^2$ are both unsubstituted aryl. In other embodiments, $L^1$ is not unsubstituted 2 to 5 membered heteroalkylene when $R^1$ and $R^2$ are both substituted or unsubstituted phenyl. In other embodiments, $L^1$ is selected from a bond, —S(O)$_n$—, —O—, —NH—, and unsubstituted $C_1$-$C_5$ alkylene. In other embodiments, n is 0 or 1. In other embodiments, $L^1$ is selected from a bond, —O—, —NH—, and unsubstituted $C_1$-$C_5$ alkylene.

In some embodiments, $L^1$ is not —S(O)$_2$— where $R^2$ is substituted or unsubstituted piperazinyl. In other embodiments, $L^1$ is not —S(O)$_2$— where $R^2$ is unsubstituted heterocycloalkyl. In other embodiments, $L^1$ is not —S(O)$_2$— where $R^1$ is substituted or unsubstituted heterocycloalkyl. In other embodiments, n is 0 or 1. In other embodiments, $L^1$ is not —S(O)$_2$— where $L^2$ is a bond.

In some embodiments, $R^2$ is not an unsubstituted 6-membered heterocycloalkyl. In other embodiments, $R^2$ is not a substituted or unsubstituted 6-membered heterocycloalkyl. In other embodiments, $R^2$ is selected from substituted or unsubstituted heteroaryl, substituted or unsubstituted 5-membered heterocycloalkyl, substituted or unsubstituted aryl, and substituted or unsubstituted cycloalkyl. $R^2$ may also be substituted or unsubstituted cycloalkyl, substituted heterocycloalkyl, substituted or unsubstituted heteroaryl, or substituted or unsubstituted aryl.

In some embodiments, $R^1$ is not substituted or unsubstituted isoxazolyl where $R^2$ is unsubstituted pyridinyl. In other embodiments, $R^1$ is not substituted or unsubstituted isoxazolyl where $L^1$ is a bond or —CH$_2$—. In other embodiments, $R^1$ is not substituted or unsubstituted isoxazolyl. In other embodiments, $R^1$ is not a 4-substituted isoxazolyl. In other embodiments, $R^1$ is not a 5-yl-isoxazolyl. In other embodiments, $R^1$ is not a 4-substituted-5-yl-isoxazolyl. In other embodiments, $R^1$ is not an isoxazolyl substituted with a fluoro-substituted aryl.

$L^1$ and $L^2$ may independently be a bond, —S(O)$_n$—, —O—, —NH—, or unsubstituted $C_1$-$C_5$ alkylene. In some embodiments, $L^1$ and $L^2$ are a bond. In other embodiments, $L^1$ or $L^2$ is a bond.

$R^1$ may be a substituted or unsubstituted cycloalkyl, substituted or unsubstituted heterocycloalkyl, substituted or unsubstituted 5- or 6-membered heteroaryl, or substituted or unsubstituted aryl. $R^1$ may also be a substituted or unsubstituted 6-membered heteroaryl, or substituted or unsubstituted aryl.

In other embodiments, $R^1$ is (1) unsubstituted $C_3$-$C_7$ cycloalkyl; (2) unsubstituted 3 to 7 membered heterocycloalkyl; (3) unsubstituted heteroaryl; (4) unsubstituted aryl; (5) substituted $C_3$-$C_7$ cycloalkyl; (6) substituted 3 to 7 membered heterocycloalkyl; (7) substituted aryl; or (8) substituted heteroaryl. In some related embodiments, (5) and (6) are substituted with an oxo, —OH, —CF$_3$, —COOH, cyano, halogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, -$L^{12}$-C($X^1$)$R^7$, -$L^{12}$-OR$^8$, -$L^{12}$NR$^{91}$R$^{92}$, or -$L^{12}$-S(O)$_m$R$^{10}$. $X^1$ is =S, =O, or =NR$^{15}$, wherein $R^{15}$ is H, —OR$^{151}$, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl. $R^{151}$ is hydrogen or $R^{11}$-substituted or unsubstituted $C_1$-$C_{10}$ alkyl. The symbol m is an integer from 0 to 2.

In other related embodiments, (7) and (8) are substituted with an —OH, —CF$_3$, —COOH, cyano, halogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, -$L^{12}$-C($X^1$)$R^7$, -$L^2$-OR$^8$, -$L^{12}$-NR$^{91}$R$^{92}$, or -$L^{12}$-S(O)$_m$R$^{10}$. $L^{12}$ is a bond, unsubstituted $C_1$-$C_{10}$ alkylene, or unsubstituted heteroalkylene. $X^1$ and m are as defined above.

$R^7$ is hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, —OR$^{71}$, or —NR$^{72}$R$^{73}$. $R^{71}$, $R^{72}$, and $R^{73}$ are independently hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl. $R^{72}$ and $R^{73}$ are optionally joined with the nitrogen to which they are attached to form an $R^{11}$-substituted or unsubstituted 3 to 7 membered heterocycloalkyl, or $R^{12}$-substituted or unsubstituted heteroaryl.

$R^8$, $R^{91}$ and $R^{92}$ are independently hydrogen, —CF$_3$, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, —C($X^2$)$R^{81}$, or —S(O)$_w$$R^{81}$. $X^2$ is =S, =O, or =NR$^{16}$. $R^{16}$ is $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl. The symbol w is an integer from 0 to 2. $R^{91}$ and $R^{92}$ are optionally joined with the nitrogen to which they are attached to form an $R^{11}$-substituted or unsubstituted 3 to 7 membered heterocycloalkyl, or $R^{12}$-substituted or unsubstituted heteroaryl.

$R^{81}$ is hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, or —NR$^{811}$R$^{812}$.

$R^{811}$ and $R^{812}$ are independently hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl. $R^{811}$ and $R^{812}$ are optionally joined with the nitrogen to which they are attached to form an $R^{11}$-substituted or unsubstituted 3 to 7 membered heterocycloalkyl, or $R^{12}$-substituted or unsubstituted heteroaryl.

In some embodiments, $R^{81}$ and $R^{16}$ are optionally joined with the atoms to which they are attached to from a substituted or unsubstituted heterocycloalkyl or substituted or unsubstituted heteroaryl. In other embodiments, $R^{811}$ and $R^{16}$ are optionally joined with the atoms to which they are attached to from a substituted or unsubstituted heterocycloalkyl or substituted or unsubstituted heteroaryl. In other embodiments, $R^{81}$ and $R^{92}$ are optionally joined with the atoms to which they are attached to from a substituted or unsubstituted heterocycloalkyl or substituted or unsubstituted heteroaryl. In other embodiments, $R^{811}$ and $R^{92}$ are optionally joined with the atoms to which they are attached to from a substituted or unsubstituted heterocycloalkyl or substituted or unsubstituted heteroaryl.

$R^{10}$ is hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, $R^{12}$-substituted or unsubstituted heteroaryl, or —NR$^{101}$R$^{102}$. $R^{101}$ and $R^{102}$ are independently hydrogen, $R^{11}$-substituted or unsubstituted $C_1$-$C_{10}$ alkyl, $R^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl. $R^{101}$ and $R^{102}$ are optionally joined with the nitrogen to which they are attached to form an $R^{11}$-substituted or unsubstituted 3 to 7 membered heterocycloalkyl, or $R^{12}$-substituted or unsubstituted heteroaryl.

$R^{11}$ is oxo, —OH, —COOH, —CF$_3$, —OCF$_3$, —CN, amino, halogen, $R^{13}$-substituted or unsubstituted 2 to 10 membered alkyl, $R^{13}$-substituted or unsubstituted 2 to 10 membered heteroalkyl, $R^{13}$-substituted or unsubstituted $C_3$-$C_7$ cycloalkyl, $R^{13}$-substituted or unsubstituted 3 to 7 membered heterocycloalkyl, $R^{14}$-substituted or unsubstituted aryl, or $R^{14}$-substituted or unsubstituted heteroaryl.

$R^{12}$ is —OH, —COOH, amino, halogen, —CF$_3$, —OCF$_3$, —CN, $R^{13}$-substituted or unsubstituted 2 to 10 membered alkyl, $R^{13}$-substituted or unsubstituted 2 to 10 membered heteroalkyl, $R^{13}$-substituted or unsubstituted $C_3$-$C_7$ cycloalkyl, $R^{13}$-substituted or unsubstituted 3 to 7 membered heterocycloalkyl, $R^{14}$-substituted or unsubstituted aryl, or $R^{14}$-substituted or unsubstituted heteroaryl.

$R^{13}$ is oxo, —OH, —COOH, amino, halogen, —CF$_3$, —OCF$_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

$R^{14}$ is —OH, —COOH, amino, halogen, —CF$_3$, —OCF$_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

In some embodiments, $R^1$ is (1), (2), (4), (5), (6), or (7) (i.e. unsubstituted $C_3$-$C_7$ cycloalkyl, unsubstituted 3 to 7 membered heterocycloalkyl, unsubstituted aryl, substituted $C_3$-$C_7$ cycloalkyl, substituted 3 to 7 membered heterocycloalkyl, or substituted aryl, respectively). In some embodiments, where $R^1$ is (3), or (8), then the heteroaryl is a 6-membered heteroaryl.

Where $R^1$ is (7) or (8) (i.e. substituted aryl or substituted heteroaryl), (7) and (8) may be substituted with an —OH, —CF$_3$, —OCF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, or -L$^{12}$-OR$^8$. In a related embodiment, L$^{12}$ is a bond. In other related embodiments, (7) and (8) may be substituted with an —OCH$_3$, —OCF$_3$, —CH$_3$, —CF$_3$, —OCH$_2$CH$_3$, halogen, or cyclopropyloxy.

$R^2$ may be: (1) unsubstituted $C_3$-$C_7$ cycloalkyl; (2) unsubstituted 3 to 7 membered heterocycloalkyl; (3) unsubstituted heteroaryl; (4) unsubstituted aryl; (5) substituted $C_3$-$C_7$ cycloalkyl; (6) substituted 3 to 7 membered heterocycloalkyl; (7) substituted aryl; or (8) substituted heteroaryl. In some related embodiments, (5) and (6) are substituted with an oxo, —OH, —CF$_3$, —COOH, cyano, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, -L$^{22}$-C($X^3$)R$^3$, -L$^{22}$-OR$^4$, -L$^{22}$-NR$^{51}$R$^{52}$, or -L$^{22}$-S(O)$_q$R$^6$. $X^3$ is =S, =O, or =NR$^{17}$, wherein $R^{17}$ is H, —OR$^{171}$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. $R^{171}$ is H or $R^{21}$-substituted or unsubstituted $C_1$-$C_{10}$ alkyl. The symbol q is an integer from 0 to 2.

In other related embodiments, (7) and (8) are substituted with an —OH, —CF$_3$, —COOH, cyano, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, -L$^{22}$-C($X^3$)R$^3$, -L$^{22}$-OR$^4$, -L$^{22}$-NR$^{51}$R$^{52}$, or -L$^{22}$-S $(O)_q R^6$. $L^{22}$ is a bond, unsubstituted $C_1$-$C_{10}$ alkylene or unsubstituted heteroalkylene. $X^3$ and q are as defined above.

$R^3$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$OR^{31}$, or —$NR^{32}R^{33}$. $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl.

$R^{31}$, $R^{32}$, and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl.

$R^4$, $R^{51}$ and $R^{52}$ are independently hydrogen, —$CF_3$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$C(X^4)R^{41}$, or —$S(O)_v R^{41}$. $R^{51}$ and $R^{52}$ are optionally joined with the nitrogen to which they are attached to form an $R^{21}$-substituted or unsubstituted 3 to 7 membered heterocycloalkyl, or $R^{22}$-substituted or unsubstituted heteroaryl.

$X^4$ is =S, =O, or =$NR^{18}$, wherein $R^{18}$ is $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. The symbol v is an integer from 0 to 2.

$R^{41}$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —$NR^{411}R^{412}$. $R^{411}$ and $R^{412}$ are independently selected from hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. $R^{411}$ and $R^4$ are optionally joined with the nitrogen to which they are attached to form an $R^{21}$-substituted or unsubstituted 3 to 7 membered heterocycloalkyl, or $R^{22}$-substituted or unsubstituted heteroaryl.

In some embodiments, $R^{41}$ and $R^{18}$ are optionally joined with the atoms to which they are attached to from a substituted or unsubstituted heterocycloalkyl or substituted or unsubstituted heteroaryl. In other embodiments, $R^{411}$ and $R^{18}$ are optionally joined with the atoms to which they are attached to from a substituted or unsubstituted heterocycloalkyl or substituted or unsubstituted heteroaryl. In other embodiments, $R^{41}$ and $R^{52}$ are optionally joined with the atoms to which they are attached to from a substituted or unsubstituted heterocycloalkyl or substituted or unsubstituted heteroaryl. In other embodiments, $R^{411}$ and $R^{52}$ are optionally joined with the atoms to which they are attached to from a substituted or unsubstituted heterocycloalkyl or substituted or unsubstituted heteroaryl.

$R^6$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —$NR^{61}R^{62}R^{61}$ and $R^{62}$ are hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. $R^{61}$ and $R^{62}$ are optionally joined with the nitrogen to which they are attached to form an $R^{21}$-substituted or unsubstituted 3 to 7 membered heterocycloalkyl, or $R^{22}$-substituted or unsubstituted heteroaryl.

$R^{21}$ is oxo, —OH, —COOH, —$CF_3$, —$OCF_3$, —CN, amino, halogen, $R^{23}$-substituted or unsubstituted 2 to 10 membered alkyl, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl.

$R^{22}$ is —OH, —COOH, amino, halogen, —$CF_3$, —$OCF_3$, —CN, $R^{23}$-substituted or unsubstituted 2 to 10 membered alkyl, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl.

$R^{23}$ is oxo, —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

$R^{24}$ is —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

In some embodiments, $R^2$ is (1), (3), (4), (5), (6), (7), or (8) (i.e. unsubstituted $C_3$-$C_7$ cycloalkyl, unsubstituted heteroaryl, unsubstituted aryl, substituted $C_3$-$C_7$ cycloalkyl, substituted 3 to 7 membered heterocycloalkyl, substituted aryl, or substituted heteroaryl, respectively). $R^2$ may also be (3), (4), (7), or (8). In other embodiments, $R^2$ is (7) or (8).

In some embodiments, where $R^2$ is (7) and (8), then (7) and (8) are substituted with an -$L^{22}$-$C(X^3)R^3$, -$L^{22}$-$OR^4$, -$L^{22}$-$NR^{51}R^{52}$, -$L^{22}$-C(NH)—$NR^{32}R^{33}$, or -L $S(O)_q R^6$.

In some embodiments, $R^3$ is —$NR^{32}R^{33}$. $X^3$ may be =O or =$NR^{17}$. $R^6$ may be —$NR^{61}R^{62}$. $R^4$ may be —$C(O)R^{41}$ or —$S(O)_v R^{41}$. $R^{41}$ may be —$NR^{411}R^{412}$.

In other embodiments where $R^2$ is (7) and (8), then (7) or (8) may be substituted with an —OH, —$CF_3$, —COOH, amino, halogen, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, or -L 22-$C(X^3)R^3$. $X^3$ may be =O.

$R^3$ may be unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, or —$NR^{32}R^{33}$. $R^{32}$ and $R^{33}$ may independently be hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl.

In another embodiment where $R^2$ is (7) or (8), then (7) and (8) may be substituted with unsubstituted 2 to 10 membered heteroalkyl, or -$L^{22}$-C(O)$R^3$. $L^{22}$ may be a bond. $R^3$ may be —$NR^{32}R^{33}$. $R^{32}$ and $R^{33}$ may independently be hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl. $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl.

In some embodiments, $R^1$ is a substituted or unsubstituted fused ring aryl or substituted or unsubstituted fused ring heteroaryl. In other embodiments, $R^2$ is substituted or unsubstituted indolyl, substituted or unsubstituted quinolinyl, or substituted or unsubstituted benzodioxolyl. $R^2$ may be a substituted or unsubstituted fused ring aryl or substituted or unsubstituted fused ring heteroaryl. $R^1$ may be a substituted or unsubstituted indolyl, substituted or unsubstituted quinolinyl, or substituted or unsubstituted benzodioxolyl.

$R^1$ and $R^2$ may independently be a substituted or unsubstituted hydantoinyl, substituted or unsubstituted dioxolanyl, substituted or unsubstituted dioxanyl, substituted or unsubstituted trioxanyl, substituted or unsubstituted tetrahydrothienyl, substituted or unsubstituted tetrahydrofuranyl, substituted or unsubstituted tetrahydrothiophenyl, substituted or unsubstituted tetrahydropyranyl, substituted or unsubstituted tetrahydrothiopyranyl, substituted or unsubstituted pyrrolidinyl, substituted or unsubstituted morpholino, substituted or unsubstituted piperidinyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyridyl, substituted or unsubstituted pyrazyl, substituted or unsubstituted pyrimidyl, substituted or unsubstituted pyridazinyl, substituted or unsubstituted thiazolyl, substituted or unsubstituted isothioazolyl, substituted or unsubstituted triazolyl, substituted or unsubstituted thienyl, substituted or unsubstituted triazinyl, substituted or unsubstituted thiadiazolyl, or substituted or unsubstituted tetrazolyl.

In another embodiment, the compound of the present invention is any one of the compounds of Tables 1-18 or 20, and/or of the methods 2-61 in the Examples section below.

In another aspect, the present invention provides a fused ring heterocycle kinase modulator (also referred to herein as a "compound of the present invention") having the formula:

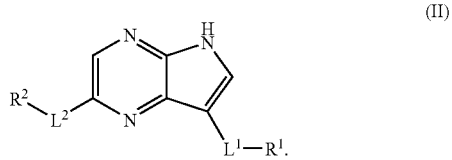

(II)

In Formula (II), $L^1$, $L^2$, $R^1$, and $R^2$ are as defined above in the discussion of Formula (I).

In another aspect, the present invention provides a fused ring heterocycle kinase modulator (also referred to herein as a "compound of the present invention") having the formula:

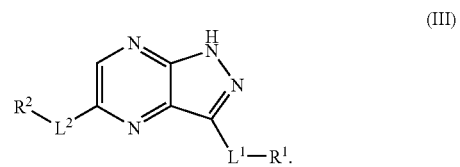

(III)

In Formula (III), $L^1$, $L^2$, $R^1$, and $R^2$ are as defined above in the discussion of Formula (I).

In some embodiments, each substituted group described above in the compounds of Formulae (I)-(III) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compounds of Formulae (I)-(III) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(III), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques. In Schemes 1, 2 and 3, $L^1$, $R^1$, $L^2$, and $R^2$ are as defined above.

The key intermediates for the synthesis of 3,5-disubstituted 1H-pyrazolo[3,4-b]pyridine derivatives are 5-bromo-1H-pyrazolo[3,4-b]pyridine and 5-bromo-3-iodo-1H-pyrazolo[3,4-b]pyridine. The iodine and/or bromine substituents on sp²-hybridized, aromatic carbon atoms present in these building blocks offer numerous synthetic possibilities for functionalization of either position. A great variety of such synthetic methods exists and these procedures are generally well known and familiar to someone with skill in the art and include, by means of example and not limitation: transition metal catalyzed processes, most notably processes utilizing palladium, iron, nickel or copper catalysts, as well as metal-halogen exchange reactions, most notably such procedures introducing lithium or magnesium, and subsequent reaction of the transient or isolated organometallic derivative with an electrophile of suitable reactivity either directly or via trans-metallation to fine tune the reactivity of the organometallic species.

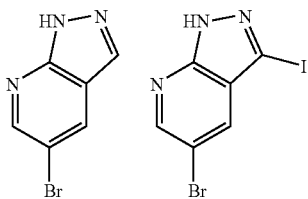

Using such methods, introduction of different substituents on the 3- and 5-position of the 1H-pyrazolo[3,4-b]pyridine core can be accomplished by introducing a chosen substituent at the 5-position starting from 5-bromo-1H-pyrazolo[3,4-b]pyridine and subsequent halogenation, especially iodination, at position 3 of the 1H-pyrazolo[3,4-b]pyridine core to enable the use of the aforementioned methods to introduce another substituent of choice at that position. Alternatively, some of the methods outlined above may be utilized to selectively functionalize 5-bromo-3-iodo-1H-pyrazolo[3,4-b]pyridine at the 3-position by selectively reacting with the iodo substituent over the bromo substituent. It is generally well known and familiar to someone with skill in the art, that a variety of palladium catalysts are known and readily available or accessible which will exhibit higher reaction rates with aromatic iodo substituents as compared to aromatic bromo substituents and such catalysts may be utilized under suitable conditions to effect selective iodine substitution.

5-bromo-1H-pyrazolo[3,4-b]pyridine or a derivative containing an appropriate protecting group may also be functionalized at the 3-position via various electrophilic aromatic substitution reactions that are generally well known and familiar to someone with skill in the art, such as FRIEDEL-CRAFTS-acylation.

The substituents introduced on either position in such fashion may either represent fully elaborated compounds, such as those claimed under this invention, or they may contain functional groups, such as, for example and without limitation, amines, carboxylic acids or esters, nitriles, olefins or halogens, either free or bearing suitable protecting groups, which in turn may be utilized as starting material in generally well known synthetic transformations to synthesize compounds that are claimed under this invention.

Suitably functionalized pyrazolo[3,4-b]pyridine derivatives, particularly 5-bromo-1H-pyrazolo[3,4-b]pyridine and 5-bromo-3-iodo-1H-pyrazolo[3,4-b]pyridine, useful in synthesizing compounds of the present invention can be prepared as outlined in Scheme 1 from commercially available 5-bromo-2-fluoropyridine. 5-Bromo-2-fluoropyridine can be selectively functionalized at the 3-position by the generally well known selective metallation of 2-fluoropyridines in a manner resembling general methods described in Schlosser, M., *Organometallics in Synthesis*, 2nd. ed., Wiley-VCH, 2002; Clayden, J., *Organolithiums: Selectivity for Synthesis*, Pergamon, 2002; and Mongin et al., *Tetrahedron* (2001) 57, 4059-4090. Thus, metallation may be accomplished by treatment with a suitable, non-nucleophilic strong base (e.g. lithium di-iso-propylamide or lithium 2,2,6,6-tetramethylpiperidide) in an aprotic solvent (e.g. THF, hexanes, ether or mixtures thereof) at low temperature, typically −78° C. or below.

The unpurified metallated intermediate can be converted to the corresponding 3-carbaldehyde 2 by treatment with a formylating reagent such as DMF, N-formyl-N-methylaniline, N-formylmorpholine, N-formylpiperidine or ethyl formate. Reaction of the carbaldehyde with hydrazine or a suitable hydrazine derivative (e.g. hydrazine-tert-butylcarbazate, or a soluble organic or inorganic salt derived from hydrazine such as hydrazine hydrochloride) either directly or upon protection of the aldehyde using a suitable protecting group (e.g. acetal) will provide access to 5-bromo-1H-pyrazolo[3,4-b]pyridine. Introduction of a suitable group at the 3-position for further elaboration can be accomplished via methods generally well known in the art, such as an electrophilic aromatic substitution (e.g. bromination or iodination). Thus, the iodide 4 is accessible from 3 by treatment with suitable reagents, such as N-iodosuccinimide, iodine monochloride or iodine, under conditions facilitating such transformation. Other examples of functionalization via electrophilic aromatic substitution are, by means of example and not limitation, FRIEDEL-CRAFTS-acylation using functionalized acyl halides such as, for example, bromoacetyl chloride, acryloyl chloride or trichloroacetyl chloride in the presence of aluminum trichloride in dichloromethane at ambient temperature or below. As will be appreciated by the skilled artisan, the products of such reactions may be utilized as starting materials for the synthesis of certain heterocyclic compounds.

Alternatively, the metallated intermediate derived from deprotonation of 5-bromo-2-fluoropyridine can be transmetallated under suitable conditions to form an organocuprate reagent (c.f. Lipshutz, B., *Organometallics in Synthesis*, 2nd. ed., Wiley-VCH, 2002). Reaction of the cuprate generated in such fashion with an acyl halide gives access to ketones of the general structure 5, which can be cyclized by reaction with hydrazine or a soluble organic or inorganic salt derived from hydrazine (e.g. hydrazine hydrochloride) to afford the corresponding 3-substituted 5-bromo-1H-pyrazolo[3,4-b]pyridines of the general structure 6.

Scheme 1

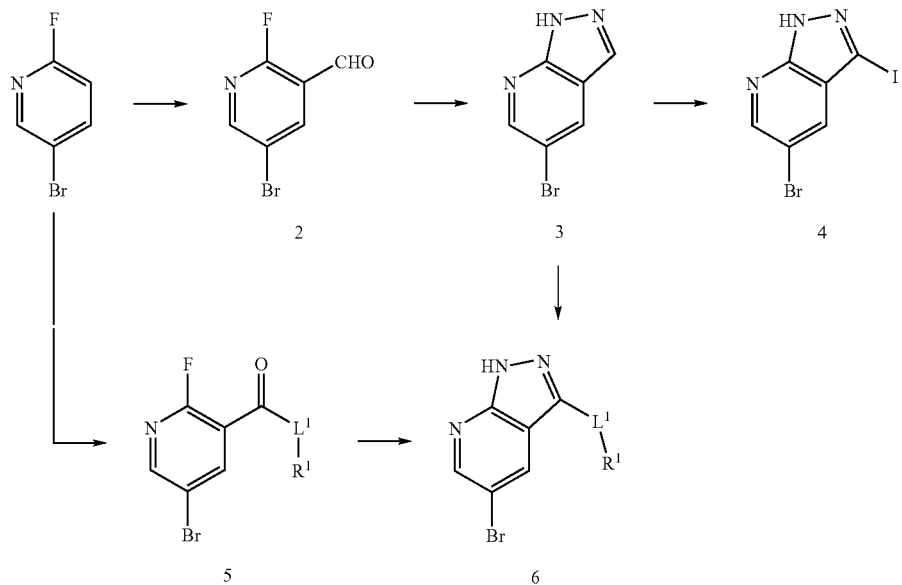

Elaboration of halides 3, 4 or 6 can be readily accomplished by generally well known methods, such as those outlined in Scheme 2 below. For example, metal catalyzed cross coupling reactions may be employed using various known transition metal compounds (e.g. compounds derived from palladium, iron or nickel). Examples of such transformations can be found in the following references: Diederich, F., Stang, P. J.—*Metal-catalyzed Cross-coupling Reactions*, Wiley-VCH, 1998; Beller, M., *Transition Metals for Organic Synthesis*, Wiley-VCH, 1998; Tsuji, J., *Palladium Reagents and Catalysts*, Wiley-VCH, $1^{st}$. & $2^{nd}$ eds., 1995, 2004; Fuerstner, A., et al., *J. Am. Chem. Soc.* (2002) 124, 13856; and Bolm, C., et al., *Chem. Rev.* (2004) 104, 6217. Other useful methods involve the conversion of a bromine or iodine substituent into a metal or metalloid substituent (e.g. organoboron, organolithium, organotin, organosilicon, organozinc, organocopper or organomagnesium compound) using generally well known methods (e.g. metal halogen exchange and, as appropriate or required, subsequent transmetallation using soluble and reactive compounds of boron, magnesium, zinc, tin, silicon or copper; for representative examples of such methodology see: Schlosser, M., *Organometallics in Synthesis*, 2nd. ed., Wiley-VCH, 2002.). Organometallic derivatives obtained in such fashion may itself be of use in transition metal catalyzed coupling reactions with aromatic or olefinic halides or triflates, or, if sufficiently reactive, be reacted directly with suitable electrophiles, such as, for example, certain organic halides, MICHAEL-acceptors, oxiranes, aziridines, aldehydes, acyl halides, or nitrites.

Selective functionalization at either the 3- or 5-position may require different strategies depending on the nature of the transformations utilized to introduce functionalities at either position, especially the sequence of functionalization at either position. Thus, it may be advantageous or necessary to achieve functionalization at the 3-position prior to functionalization of the 5-position in some cases while the opposite approach may be required in other cases, depending on the nature of the specific groups to be introduced, the methods required to accomplish such transformations, or the inherent selectivity of the methods utilized. For example, some reactants, such as for example some boronic acids or their esters that are electron deficient (e.g. contain one or more electron withdrawing substituents or that represent derivatives of certain heterocyclic systems) and/or contain one or more substituents ortho to the boron-carbon bond may require the use of highly active palladium catalysts (such as those mentioned in Vilar, R., Christman, U.—*Angew. Chem.* (2005) 117, 370; Littke, A. F., Fu, G.—*Angew. Chem.* (2002) 114, 4350.) and more forcing conditions, such as higher temperatures and/or longer reaction times. Such conditions may not be conducive to achieving appreciable selectivities in reactions of 5-bromo-3-iodo-1H-pyrazolo[3,4-b]pyridine. Hence, in such cases, it may be advantageous to avoid selectivity issues altogether by sequential substitution of bromine in 5-bromo-1H-pyrazolo[3,4-b]pyridine, iodination at the 3-position and subsequent introduction of the second substituent at position 3 utilizing the methods detailed above. Generally, when substitution of the halogen atom at either position require conditions that involve highly reactive catalysts or reagents under conditions that generally do not favor high levels of selectivity between the two halogen atoms present in 5-bromo-3-iodo-1H-pyrazolo[3,4-b]pyridine, it may be advantageous to resort to this sequential approach.

It will also be appreciated that protection of reactive groups within $L^1$, $L^2$, $R^1$ and/or $R^2$ as well as the pyrazolo[3,4-b]pyridine scaffold, (e.g. the proton at position 1), with a suitable protecting group may be advantageous or required. For example it was found to be advantageous in some cross-coupling reactions to protect the nitrogen at position 1 of the 1H-pyrazolo[3,4-b]pyridine scaffold by introduction of either a (2-trimethylsilylethoxy)-methyl or (2-methoxyethoxy)methyl group at that position. Introduction and removal of these protecting groups could be conveniently accomplished by methods well known in the chemical literature. The compounds obtained by any of the aforementioned methods may contain functional groups, either free or protected, that can be further elaborated by generally well known methods.

A more detailed description of the utilization of cross-coupling procedures in the synthesis of the compounds claimed under this invention is illustrated in Scheme 2: $X^1$ and $X^2$ are selected from, but not limited to, halogen, boronic acid or ester, trifluoroborate salt, organomagnesium, organozinc, or organotin. With respect to the introduction of individual residues -$L^1$-$R^1$ or -$L^2$-$R^2$ such transformations, as outlined above, can be achieved via standard halogen cross-coupling methodologies.

Org. Lett (2003) 5, 4611; Bach, T., et al., J. Org. Chem. (2002) 67, 5789, Adamczyk, M. et. al., Tetrahedron (2003) 59, 8129.

This methodology may be extended to the incorporation of non-carbon based nucleophiles (e.g. alcohols, thiols, primary or secondary amines) that may optionally contain suitable protecting groups of alcohols, thiols or amines. Examples of such groups can be found in Greene, T., et al., Protective Groups in Organic Synthesis, 3rd ed., John Wiley & Sons, 1999. Exemplary methods of protection are described in Ley, Scheme 2

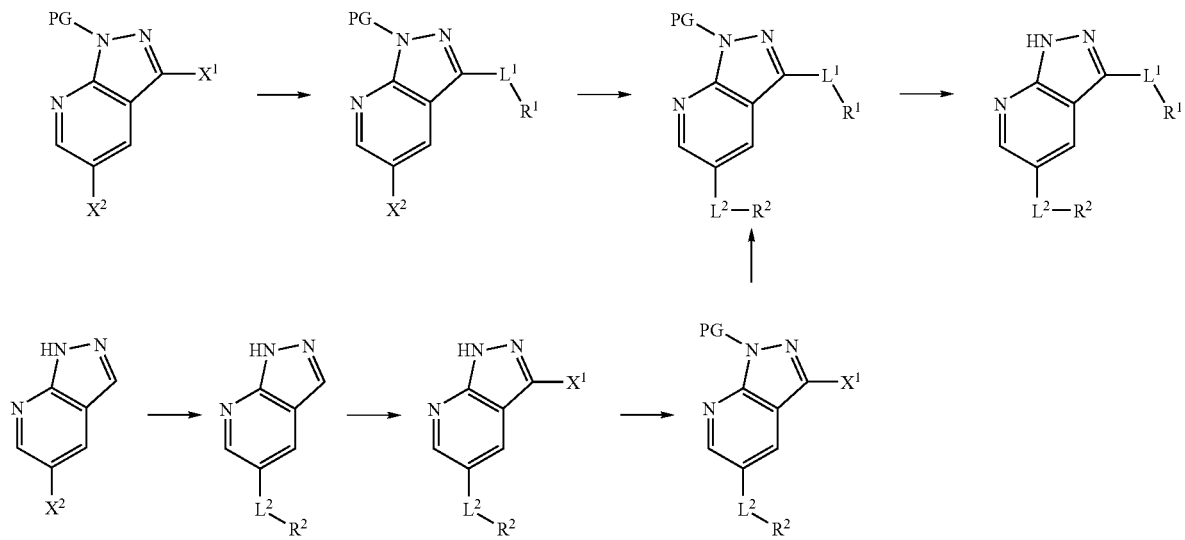

Couplings of the corresponding bromide or iodide ($X^1$, $X^2$=Br, I) with suitable reagents such as boronic acids and boronates, organoboranes, organostannanes, organozinc compounds, organomagnesium compounds, olefins or terminal alkynes (either purchased or obtained via generally well known protocols) can be carried out in the presence of a suitable transition metal catalyst (e.g. palladium compounds). The coupling may optionally be performed in the presence of ligands such as phosphines, diphosphines, Arduengo-type heterocyclic carbenes or arsines. Organic or inorganic bases (e.g. tertiary or secondary amines, alkaline carbonates, bicarbonates or phosphate) and/or other well known additives (e.g. lithium chloride, copper halides or silver salts) may be utilized to assist or accelerate such transformations.

These cross coupling reactions may be carried out in suitable solvents such as THF, dioxane, dimethoxyethane, diglyme, dichloromethane, dichloroethane, acetonitrile, DMF, N-methylpyrrolidone, water, or mixtures of thereof at temperatures ranging from 25° C. to 200° C. using. The temperature may optionally be maintained with heating, conventional heating or microwave irradiation. In the case of the 3-iodo-5-bromo-1H-pyrazolo[3,4-b]pyridine, the selective or preferential substitution of the iodo substituent over the bromo substituent is possible under generally less forcing conditions, such as lower temperature and shorter reaction times using a suitable transition metal catalyst. Selective functionalizations of di- or oligohalogen compounds by means of transition metal catalyzed transformations are well precedented in the chemical literature: see for example Ji, J., et al.

S., et al., Angew. Chem. (2003) 115, 5558; Wolfe, J., et al., Acc. Chem. Res. (1998) 31, 805; Hartwig, Acc. Chem. Res. (1998) 31, 852; Navarro, O., et al., J. Org. Chem. (2004) 69, 3173, Ji, J., et al., Org. Lett (2003) 5, 4611. The compounds obtained by such methods can be further elaborated by well known methods to obtain other compounds of the present invention.

In some cases it may be advantageous to achieve cross-couplings to carbon or non-carbon atoms by first converting the respective halogen derivative into the corresponding organometallic derivative (e.g., a boronic acid or ester, trifluoroborate salt, organomagnesium, organozinc or organotin compound). Such compounds are accessible by means of substituting the halide moiety with an appropriate metal or metalloid. Any functional groups present (e.g. the ring nitrogen in position 1 of the pyrazolo[3,4-b]pyridine), may need to be protected by a suitable protecting group ("PG"). See Greene, et al, 1999.

Introduction of such metals or metalloids can be achieved by generally well-known methods, such as metallation using metals or a metal-halogen exchange reaction. Useful metals for metallation include alkaline or alkaline earth metals or activated forms of such metals. Suitable reagents for use in metal-halogen exchange reactions include organolithium or organomagnesium compounds (e.g. n-butyllithium, tert-butyllithium or iso-propylmagnesium chloride or bromide). Subsequent transmetalation reactions of the organometallic intermediate may be performed as needed with a suitable soluble and reactive metal compound such as magnesium chloride, magnesium bromide, tri-n-butyltin chloride, trimethyltin chloride, trimethyl borate, triethyl borate, tri-isopropyl borate, zinc triflate or zinc chloride. Introduction of a boronic acid pinacol ester can be conveniently achieved by reacting the halogen derivative directly with bis(pinacolato) diboron in the presence of dichloro[1,1'-bis(diphenylphosphino)ferrocene]palladium(II) and suitable bases (e.g. potassium or sodium acetate) in solvents such as DMSO, DMF, DMA or N-methylpyrrolidone at temperatures ranging from 80-160° C. Conventional heating or microwave irradiation may be employed to maintain the appropriate temperature (for literature precedent of similar transformations, see Ishiyama, T., et al., *J. Org. Chem.* (1995) 60, 7508.).

Methods for conversion of the boronic acid pinacol ester obtained by this method into other boronic acid derivatives such as boronic acids, boronates, or trifluoroborate salts are generally well known. As will be apparent to the skilled artisan, such organometallic derivatives may be utilized in cross-coupling reactions similar to those described above in the case of halogen containing derivatives of pyrazolo[3,4-b]pyridine. Such couplings can be effected utilizing suitable coupling partners, such as aromatic, heteroaromatic halides or olefinic reagents under conditions identical or evidently similar and/or related to the methods described above.

Other methods may utilize the reactivity of organometallic derivatives generated from halogen containing derivatives of pyrazolo[3,4-b]pyridine by any of the methods described above. For example, derivatives containing alkaline or alkaline earth metals (e.g. organolithium, organomagnesium or organozinc compounds) may be employed in direct couplings to a range of other electrophilic coupling partners such as, for example, activated olefins (MICHAEL-acceptors), aldehydes, nitrites, aromatic nitro compounds, carboxylic acid derivatives, oxiranes, aziridines, organic disulfides or organic halides. Such transformations are generally well known in the art (for reactions with aromatic nitro compounds, see for example Sapountzis, I., et al., *J. Am. Chem. Soc.* (2002) 124, 9390.).

The synthetic strategies utilized to access 3,5-disubstituted 1H-pyrrolo[2,3-b]pyrazine derivatives are closely related to the strategies described above for 1H-pyrazolo[3,4-b]pyridine derivatives, with the main difference relating to the synthesis of the 1H-pyrrolo[2,3-b]pyrazine scaffold itself. The key intermediates utilized are 3-substituted 5-iodo-1H-pyrrolo[2,3-b]pyrazine derivatives and 5-bromo-1H-pyrrolo[2,3-b]pyrazine itself.

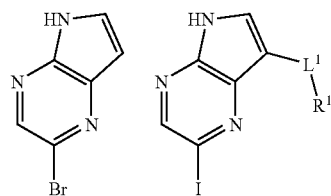

The general synthetic strategies to access 3,5-disubstituted 1H-pyrazolo[3,4-b]pyridine derivatives from 5-bromo-1H-pyrazolo[3,4-b]pyridine outlined above will also pertain to accessing 3,5-disubstituted 1H-pyrrolo[2,3-b]pyrazine derivatives from 5-bromo-1H-pyrrolo[2,3-b]pyrazine and 3-substituted 5-iodo-1H-pyrrolo[2,3-b]pyrazine derivatives. However, the exact conditions for otherwise similar or identical transformations may very well be different for 1H-pyrrolo[2,3-b]pyrazine derivatives and optimization depending on the scaffold utilized may be required.

5-Bromo-1H-pyrrolo[2,3-b]pyrazine is accessible via regioselective SONOGASHIRA-coupling of 3-amino-2,6-dibromo-pyrazine with trimethylsilylacetylene (see Adamczyk, M., et al.—*Tetrahedron* (2003) 59, 8129.), N-acylation, and subsequent cyclization using -n-butylammonium fluoride (for precedent of this reaction please see WO2004/032874A2). Starting from commercially available 3-amino-2,6-dibromo-pyrazine, 5-bromo-3-trimethylsilanylethynyl-pyrazin-2-ylamine can be obtained by reaction with trimethylsilylacetylene in the presence of a palladium catalyst, such as tetrakis(triphenylphosphino)palladium(0) and a catalytic amount of a copper co-catalyst, such as copper(I)-iodide in a mixture of DMF and a basic tertiary organic amine, such as triethylamine at elevated temperatures. Acetylation with acetyl chloride in pyridine at 20-60° C. gives access to N-(5-bromo-3-trimethylsilanylethynyl-pyrazin-2-yl)-acetamide and subsequent cyclization with tetra-n-butylammonium fluoride in THF under reflux affords 5-bromo-1H-pyrrolo[2,3-b]pyrazine.

Introduction of a suitable group at the 3-position for further elaboration can be accomplished via methods generally well known in the art, such as an electrophilic aromatic substitution (e.g. bromination or iodination). Thus, 5-bromo-3-iodo-1H-pyrrolo[2,3-b]pyrazine is accessible from 5-bromo-1H-pyrrolo[2,3-b]pyrazine by treatment with suitable reagents, such as N-iodosuccinimide, iodine monochloride or iodine, under conditions facilitating such transformation.

Other examples of functionalization via electrophilic aromatic substitution are, by means of example and not limitation, FRIEDEL-CRAFTS-acylation using functionalized acyl halides such as, for example, bromoacetyl chloride, acryloyl chloride or trichloroacetyl chloride in the presence of aluminum trichloride in dichloromethane at ambient temperature or below. As will be appreciated by the skilled artisan, the products of such reactions either represent compounds claimed under this invention or may be utilized as starting materials for the synthesis of such compounds, most notably certain heterocyclic compounds.

Further elaboration of halide D ($X^2$=Br, I) as well as selective sequential substitution of both halogen substituents in 5-bromo-3-iodo-1H-pyrrolo[2,3-b]pyrazine can be readily accomplished by generally well known methods, such as, for example, sequential metal catalyzed cross coupling reactions may be employed using various known transition metal compounds (e.g. compounds derived from palladium, iron or nickel). Examples of such transformations can be found in the following references: Diederich, F., Stang, P. J.—*Metal-catalyzed Cross-coupling Reactions*, Wiley-VCH, 1998; Beller, M., *Transition Metals for Organic Synthesis*, Wiley-VCH, 1998; Tsuji, J., *Palladium Reagents and Catalysts*, Wiley-VCH, $1^{st}$. & $2^{nd}$ eds., 1995, 2004; Fuerstner, A., et al., *J. Am. Chem. Soc.* (2002) 124, 13856; and Bolm, C., et al., *Chem. Rev.* (2004) 104, 6217. The general methods known in the chemical literature and familiar to someone with skill in the art are essentially the same methods as those described above for similar or identical transformations utilizing 1H-pyrazolo[3,4-b]pyridine derivatives.

As was discussed for 1H-pyrazolo[3,4-b]pyridines the skilled artisan will appreciate that selective functionalization at either the 3- or 5-position may require different strategies depending on the nature of the transformations utilized to introduce functionalities at either position, especially the sequence of functionalization at either position. Thus, it may be advantageous or necessary to achieve functionalization at the 3-position prior to functionalization of the 5-position in some cases while the opposite approach may be required in other cases, depending on the nature of the specific groups to be introduced, the methods required to accomplish such transformations, or the inherent selectivity of the methods utilized.

In the case of the 3-iodo-5-bromo-1H-pyrrolo[2,3-b]pyrazine, the selective or preferential substitution of the iodo substituent over the bromo substituent is possible under generally less forcing conditions, such as lower temperature and shorter reaction times using a suitable transition metal catalyst. Selective functionalizations of di- or oligohalogen compounds by means of transition metal catalyzed transformations are well precedented in the chemical literature: see for example Ji, J., et al. *Org. Lett* (2003) 5, 4611; Bach, T., et al., *J. Org. Chem* (2002) 67, 5789, Adamczyk, M. et. al., *Tetrahedron* (2003) 59, 8129.

In the case of halide D ($X^2$=Br, I) other useful methods may involve the conversion of a bromine or iodine substituent into a metal or metalloid substituent (e.g. organoboron, organolithium, organotin, organosilicon, organozinc, organocopper or organomagnesium compound) using generally well known methods (e.g. metal halogen exchange and, as appropriate or required, subsequent transmetallation using soluble and reactive compounds of boron, magnesium, zinc, tin, silicon or copper; for representative examples of such methodology see: Schlosser, M., *Organometallics in Synthesis*, 2nd. ed., Wiley-VCH, 2002). Organometallic derivatives obtained in such fashion may itself be of use in transition metal catalyzed coupling reactions with aromatic or olefinic halides or triflates, or, if sufficiently reactive, be reacted directly with suitable electrophiles, such as, for example, certain organic halides, MICHAEL-acceptors, oxiranes, aziridines, aldehydes, acyl halides, or nitriles. Again, the general methods known in the chemical literature are essentially the same as those described above for similar or identical transformations utilizing 1H-pyrazolo[3,4-b]pyridine derivatives.

In certain such transformations, it may be advantageous or required to introduce one or more suitable protecting groups, in order to temporarily substitute acidic protons, such as, for example, the hydrogen atoms attached to nitrogen or oxygen, as needed, and in particular the hydrogen atom in position 1 of the 1H-pyrrolo[2,3-b]pyrazine scaffold, by methods well known in the chemical literature (cf. T. W. Greene, P. G. M. Wuts—*Protective Groups in Organic Synthesis*, 3rd ed., John Wiley & Sons, 1999).

The cross-coupling methodology described above may be extended to the incorporation of non-carbon based nucleophiles (e.g. alcohols, thiols, primary or secondary amines) that may optionally contain suitable protecting groups of alcohols, thiols or amines. Examples of such groups can be found in Greene, T., et al., *Protective Groups in Organic Synthesis*, 3rd ed., John Wiley & Sons, 1999. Exemplary methods of protection are described in Ley, S., et al., *Angew. Chem.* (2003) 115, 5558; Wolfe, J., et al., *Acc. Chem. Res.* (1998) 31, 805; Hartwig, *Acc. Chem. Res.* (1998) 31, 852; Navarro, O., et al., *J. Org. Chem.* (2004) 69, 3173, Ji, J., et al., *Org. Lett* (2003) 5, 4611. The compounds obtained by such methods can be further elaborated by well known methods to obtain other compounds of the present invention. In some cases, direct substitution of the 5-iodo or 5-bromo substituent in 1H-pyrrolo[2,3-b]pyrazine with an amine, alcohol or thiol may be successfully accomplished at ambient or elevated temperatures in the presence of weak acids, such as, for example, acetic acid, or a strong, non-nucleophilic base, such as, for example, sodium hydride either in neat amine, alcohol or thiol, respectively or in a suitable aprotic solvent, such as, for example, DMF, NMP, DMSO, or acetonitrile.

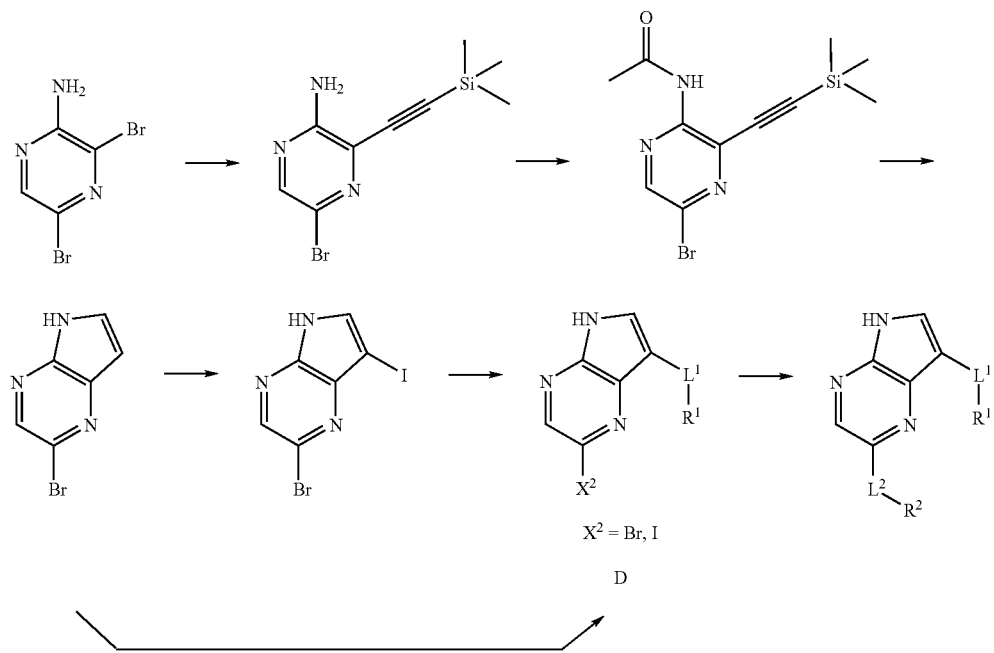

Scheme 3

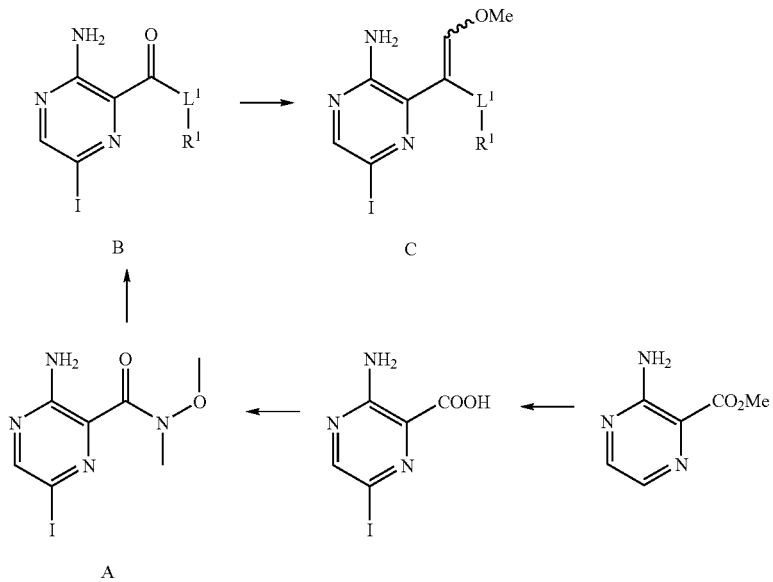

An alternative method for the synthesis of 3,5-disubstituted 1H-pyrrolo[2,3-b]pyrazine derivatives was developed, starting from methyl 2-amino-3-pyrazinecarboxylate, incorporation of an iodine atom on the 5-position to give methyl 2-amino-5-iodo-3-pyrazinecarboxylate can be achieved by various known methods, such as reaction with N-iodosuccinimide in ethanol at reflux. The halogenated ester obtained by such means may then be hydrolized by standard methods. For example, treatment with lithium hydroxide in THF-water mixtures at ambient temperature affords the corresponding acid.

Synthesis of a ketone intermediate B can be achieved by treating the corresponding WEINREB-amide A (3-amino-6-iodo-pyrazine-2-carboxylic acid methoxy-methyl-amide) or its hydrochloride salt with a suitable organometallic species, for example, using an organomagnesium or organolithium compound. (for examples of the use of N-methoxy-N-methylamides (Weinreb Amides) in ketone synthesis, see S. Nam, S. M. Weinreb—*Tetrahedron Lett.* 1981, 22, 3815.) 3-Amino-6-iodo-pyrazine-2-carboxylic acid methoxy-methyl-amide (A) is accessible by condensation of the parent acid with N,O-dimethylhydroxylamine using standard methods for amide-formation, either by prior activation of the acid or in situ or via direct condensation. Methods and reagents for both transformations are described in the chemical literature and well known to someone skilled in the art, such as in the case of direct methods using suitable coupling reagents such as, but not limited to, PyBOP, HBTU or HATU.

The organometallic reagents required for the introduction of a ketone residue $L^1R^1$ in B can be obtained either commercially or synthesized by various methods described in the literature, such as, but not limited to the GRIGNARD-reaction of organic chlorides, bromides, or iodides, with magnesium (cf. J. March—*Advanced Organic Chemistry*, 3rd ed., John Wiley & Sons, 1992), metal-halogen exchange reactions of organic bromides or iodides using suitable organolithium or organomagnesium compounds such as, but not limited to, n-butyllithium, tert-butyllithium or iso-propylmagnesium chloride or bromide (e.g. J. Clayden—*Organolithiums: Selectivity for Synthesis*, Pergamon, 2002; A. Boudier, L. O. Bromm, M. Lotz, P. Knochel—*Angew. Chem. Int. Ed.* (2000) 39, 4414.) or deprotonation of sufficiently acidic compounds, such as for example pyrimidines, pyrazines, 2-chloro- or 2-fluoropyridines using a suitable base, such as for example lithium N,N-diisopropylamide or lithium 2,2,6,6-tetramethylpiperidide (cf. J. Clayden—*Organolithiums: Selectivity for Synthesis*, Pergamon, 2002; A. Turck, N. Plé, F. Mongin, G. Quéguiner—*Tetrahedron* (2001) 57, 4489; F. Mongin, G. Quéguiner—*Tetrahedron* (2001) 57, 4059). In certain such transformations, it may be advantageous or required to introduce one or more suitable protecting groups, in order to temporarily substitute acidic protons (e.g. the hydrogen atoms attached to nitrogen or oxygen) as needed, by methods well known in the chemical literature (cf. T. W. Greene, P. G. M. Wuts—*Protective Groups in Organic Synthesis*, 3rd ed., John Wiley & Sons, 1999).

Conversion of the ketone intermediate B to the methoxyvinyl derivative C can be achieved by several known methods but is most conveniently carried out via a WITTIG-reaction (cf. B. E. Maryanoff, A. B. Reitz—*Chem. Rev.* (1989) 89, 863) using an ylid generated from commercially available methoxymethyltriphenylphosphonium chloride and a suitable base, for example, but not limited to, a strong organometallic base such as, but not limited to, a non-nucleophilic amide such as the lithium, sodium or potassium salt of bis(trimethylsilyl) amine.

Subsequent cyclization of the resulting olefin C, which can be utilized in either the E- or Z-form or a mixture of these both forms, can be achieved under general acid catalysis conditions to afford 3-substituted 1H-5-iodo-pyrrolo[2,3-b]pyrazines. Such methods may utilize strong inorganic or organic acids, such as sulfuric acid, perchloric acid, hydrochloric acid, trifluoromethanesulfonic acid or trifluoroacetic acid in suitable solvents (e.g. THF, dioxane, diethyl ether, dimethoxyethane, diglyme, dichloromethane, dichloroethane or chloroform, water, methanol, or ethanol, or mixtures thereof) at temperatures ranging from 0° C. to 160° C. A similar cyclization has been described by Sakamoto et al., *Heterocycles* (1992), 34(12), 2379-84. There the authors describe the conversion of 2-nitro-3-(2-ethoxyvinyl)pyridine to the parent pyrrolo[2,3-b]pyridine. Formation of the vinyl group was reported to be achieved via a STILLE-coupling of the 3-bromo analog with tributyl-2-ethoxyvinylstannane.

The utility of 3-substituted 1H-5-iodo-pyrrolo[2,3-b]pyrazines in the synthesis of compounds claimed under this invention will be obvious to someone skilled in the art based on the methods described above. One of skill will immediately understand that the synthetic methods described herein, including the Examples section below, may be used and/or elaborated to obtain the compounds of Formulae (I), (II), and/or (III).

A. Protecting Groups

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

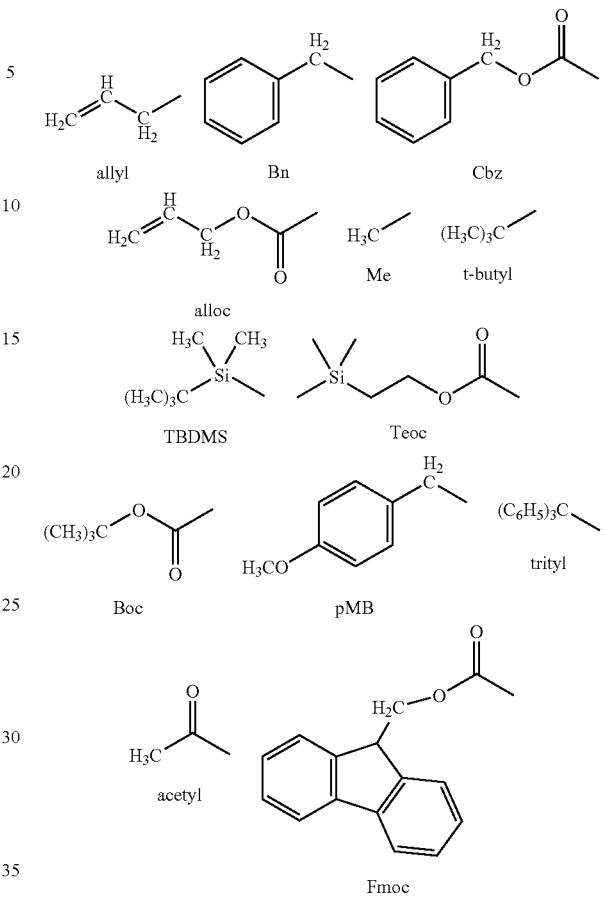

II. Methods of Inhibiting Kinases

In another aspect, the present invention provides methods of modulating protein kinase activity using the fused ring heterocycle kinase modulators of the present invention. The term "modulating kinase activity," as used herein, means that the activity of the protein kinase is increased or decreased when contacted with a fused ring heterocycle kinase modulator of the present invention relative to the activity in the absence of the fused ring heterocycle kinase modulator. Therefore, the present invention provides a method of modulating protein kinase activity by contacting the protein kinase with a fused ring heterocycle kinase modulator of the present invention (e.g. the compounds of any one of Formulae (I)-(III)).

In an exemplary embodiment, the fused ring heterocycle kinase modulator inhibits kinase activity. The term "inhibit," as used herein in reference to kinase activity, means that the kinase activity is decreased when contacted with a fused ring heterocycle kinase modulator relative to the activity in the absence of the fused ring heterocycle kinase modulator. Therefore, the present invention further provides a method of inhibiting protein kinase activity by contacting the protein kinase with a fused ring heterocycle kinase modulator of the present invention.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member.

In some embodiments, the kinase is selected from Abelson tyrosine kinase, Ron receptor tyrosine kinase, Met receptor tyrosine kinase, Fms-like tyrosine kinase-3, Aurora kinases, p21-activated kinase-4, and 3-phosphoinositide-dependent kinase-1.

In another embodiment, the kinase is a mutant kinase, such as a mutant Bcr-Abl kinase, FLT3 kinase or aurora kinases. Useful mutant Bcr-Abl kinases include those having at least one of the following clinically isolated mutations: M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In some embodiments, the mutant Abl kinase has a T315I mutation. The numbering system denoting the position of the amino acid mutation above the well known wild-type ABL numbering according to ABL exon Ia. See Deininger, M., et al., $Blood$ 105(7), 2640 (2005). The numbering system is reproduced in FIG. 1. In some embodiments, the mutant Bcr-Abl kinase includes at least one of the mutations listed above and has at least 80%, 85%, 90%, 95%, 96%, 97%, 98%, 99%, or 100% sequence identity to the sequence of FIG. 1. In some embodiments, the mutant Bcr-Abl kinase includes at least one of the mutations listed above, has a sequence identity to FIG. 1 as discussed above, and includes at least 50, 100, 150, 200, 250, 300, 350, 400, 450, 500, 550, 600, 650, 700, 750, 800, 850, 900, 950, 1000, 1050, or 1100 amino acids.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., $Nuc.$ $Acids$ $Rec.$ 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., $Nucleic$ $Acids$ $Research,$ 28:2919-26, 2000; Gouet, et al., $Bioinformatics,$ 15:305-08 (1999). Homologs may, for example, have a BLAST E-value of $1 \times 10^{-6}$ over at least 100 amino acids (Altschul et al., $Nucleic Acids Res.,$ 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labeled, etc.) in order to utilize them in the investigation of enzyme or polypeptide characterization, structure, and/or function.

In an exemplary embodiment, the fused ring heterocycle kinase modulator of the present invention is a kinase inhibitor. In some embodiments, the kinase inhibitor has an $IC_{50}$ of inhibition constant ($K_i$) of less than 1 micromolar. In another embodiment, the kinase inhibitor has an $IC_{50}$ or inhibition constant ($K_i$) of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 1 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

III. Methods of Treatment

In another aspect, the present invention provides methods of treating a disease mediated by kinase activity (kinase-mediated disease or disorder) in a subject (e.g. mammals, such as humans). By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms. The method includes administering to the subject an effective amount of a fused ring heterocycle kinase modulator of the present invention (e.g. the compounds of any one of Formulae (I)-(III)).

Examples of kinase associated diseases include cancer (e.g. leukemia, tumors, and metastases), allergy, asthma, obesity, inflammation (e.g. inflammatory diseases such as inflammatory airways disease), hematological disorders, obstructive airways disease, asthma, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, such as myeloproliferative disorders.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the invention are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

IV. Assays

The compounds of the present invention may be easily assayed to determine their ability to modulate protein kinases, bind protein kinases, and/or prevent cell growth or proliferation. Some examples of useful assays are presented below.

A. Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, *Science*, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., *J. Comp. Chem.* 13:505-24, 1992).

The screening of compounds of the present invention that bind to and/or modulate kinases (e.g. inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., *J. Med. Chem.* 42: 5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., *Perspectives in Drug Discovery and Design*, 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106: 765-84, 1984) and $C^2$ MMFF (Merck Molecular Force Field; Accelrys, San Diego, Calif.). More automated docking may be accomplished by using programs such as DOCK (Kuntz et al., *J. Mol. Biol.*, 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., *J. Mol. Biol.* 245: 43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

B. Cell Growth Assays

A variety of cell growth assays are known in the art and are useful in identifying fused ring heterocycle compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

V. Pharmaceutical Compositions and Administration

In another aspect, the present invention provides a pharmaceutical composition including a fused ring heterocycle kinase modulator in admixture with a pharmaceutically acceptable excipient. One of skill in the art will recognize that the pharmaceutical compositions include the pharmaceutically acceptable salts of the fused ring heterocycle kinase modulators described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20th ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifica-

EXAMPLES

The following examples are offered to illustrate, but not to limit the claimed invention. The preparation of embodiments of the present invention is described in the following examples. Those of ordinary skill in the art will understand that the chemical reactions and synthesis methods provided may be modified to prepare many of the other compounds of the present invention. Where compounds of the present invention have not been exemplified, those of ordinary skill in the art will recognize that these compounds may be prepared by modifying synthesis methods presented herein, and by using synthesis methods known in the art.

Synthesis of the Compounds:

Method 1:

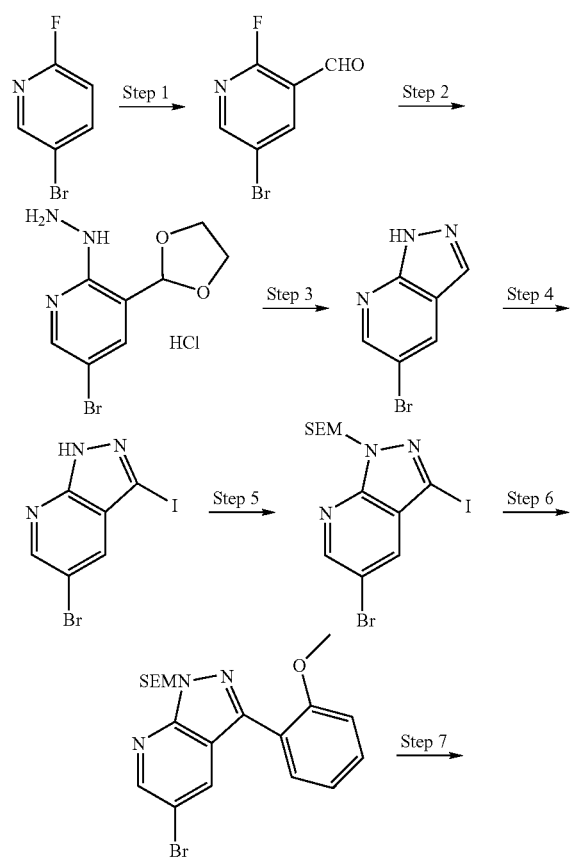

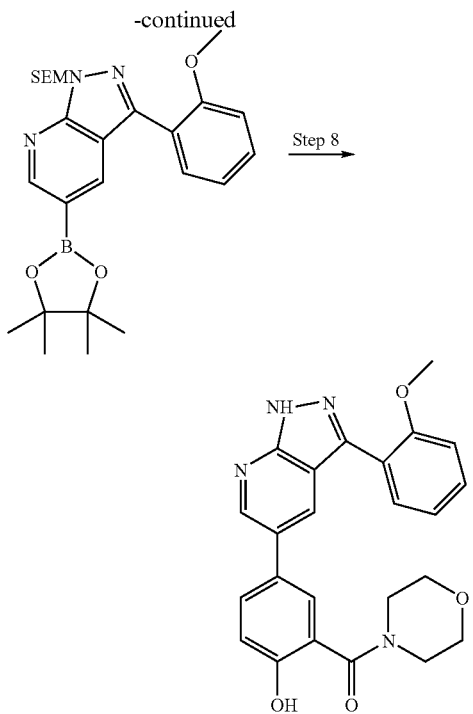

Step 1: Synthesis of 5-bromo-2-fluoro-pyridine-3-carbaldehyde

A solution of lithium di-iso-propylamine (5 mL, 35 mmol) in anhydrous THF (40 mL) was cooled to −78° C. under nitrogen and n-butyl lithium (2.5 M in hexanes, 12 mL, 30 mmol) was added. The mixture was then stirred at −78° C. for 15 min before 5-bromo-2-fluoro-pyridine (5 g, 28 mmol) was added. The resulting mixture was then stirred at −78° C. for 90 min. N-formylpiperidine (4 mL, 36 mmol) was added very rapidly to the suspension at −78° C. and the mixture stirred vigorously for 60 sec. The reaction was immediately quenched by the addition of a 10% (w/v) aqueous solution of citric acid. The mixture was warmed to room temperature and distributed between water and dichloromethane. The aqueous phase was extracted three times with dichloromethane and the organic phases were combined, dried over sodium sulfate, filtered and concentrated. Crystallization of the crude product from cyclohexane afforded 5-bromo-2-fluoro-pyridine-3-carbaldehyde (2.993 g, 52% yield) as pale beige flaky crystals. $^1$H-NMR (500 MHz, $d_6$-DMSO) δ 10.07 (s, 1H), 8.70 (dd, 1H), 8.55 (dd, 1H). MS: m/z 236, 238 [MNa$^+$], 204, 206 [MH$^+$], 176, 178 [MH-CO$^+$].

Steps 2 and 3: Synthesis of 5-bromo-1H-pyrazolo[3,4-b]pyridine 5-bromo-2-fluoro-pyridine-3-carbaldehyde (13.66 g, 66.96 mmol), pinacol (8.75 g, 74.0 mmol) and para-toluene-sulfonic acid monohydrate (1.50 g, 7.89 mmol) were placed in a flask equipped with a DEAN-STARK-condenser and dissolved in anhydrous benzene (400 mL). The mixture was heated to reflux and solvent distilled off until the distillate remains clear and the remaining volume was approximately 200 ml. The mixture was diluted with ethyl acetate (300 mL) and washed with a saturated aqueous solution of sodium bicarbonate and brine, then dried over sodium sulfate, filtered and concentrated. The resulting residue was dissolved in a mixture of ethanol (400 mL) and di-iso-propyl-ethyl-amine (25 mL). Anhydrous hydrazine (15 ml, 0.48 mol) was then added and the resulting mixture was stirred under reflux conditions for 4 h. The mixture was then concentrated to dryness and the resulting residue was distributed between water and toluene. The organic phase was washed with brine twice, dried over sodium sulfate, filtered and concentrated. The residue was dissolved in anhydrous ether (700 mL) and hydrogen chloride in anhydrous ether (2M, 70 mL) was added slowly to the vigorously stirred solution. The precipitate was filtered off, washed with ether and hexane and then dried in vacuum. $^1$H-NMR (500 MHz, $d_6$-DMSO) δ 10.31 (s, br, 1H), 8.86 (s, 1H), 8.37 (d, 1H), 7.88 (d, 1H), 6.08 (s, 1H), 3.56 (s, br), 1.27 (s, 6H), 1.19 (s, 6H). MS: m/z 198, 200 [MH$^+$].

The above solid was dissolved in a mixture of water (500 mL), ethanol (200 mL) and concentrated aqueous hydrochloric acid (50 mL) at 50-65° C. The mixture was then stirred at room temperature for 16 h before being neutralized to pH=8 with sodium bicarbonate. The resulting precipitate was filtered off and the aqueous phase extracted three times with ethyl acetate. The combined organic phases are washed with brine, dried over sodium sulfate, filtered and concentrated. The resulting residue and the precipitate obtained are crystallized from ethanol to afford 5-bromo-1H-pyrazolo[3,4-b]pyridine (6.615 g, 50% yield) as a crystalline beige to pale olive-green solid. $^1$H-NMR (500 MHz, $d_6$-DMSO) δ 13.91 (s, 1H), 8.60 (d, 1H), 8.54 (d, 1H), 8.16 (s, br, 1H). MS: m/z 198, 200 [MH$^+$].

Step 4: Synthesis of 5-bromo-3-iodo-1H-pyrazolo[3,4-b]pyridine 5-bromo-1H-pyrazolo[3,4-b]pyridine (3.00 g, 15.2 mmol) and N-iodosuccinimide (3.60 g, 16.0 mmol) were dissolved in anhydrous dichloroethane (100 mL). The resulting mixture was stirred under reflux conditions for 6 h, cooled to room temperature and diluted with THF (300 mL). The resulting solution was washed with a saturated aqueous solution of sodium thiosulfate (100 mL) and brine, then dried over magnesium sulfate, filtered and concentrated. The residue was titurated with a 1:1 mixture of dichloromethane and ether and then ether before being dried in vacuum to afford 5-bromo-3-iodo-1H-pyrazolo[3,4-b]pyridine (3.795 g, 77% yield) as a beige-brown solid. $^1$H-NMR (500 MHz, $d_6$-DMSO) δ 14.31 (s, 1H), 8.65 (d, 1H), 8.20 (d, 1H). MS: m/z 323, 325 [MH$^+$].

Step 5: Synthesis of 5-bromo-3-iodo-1-(2-trimethylsilanyl-ethoxymethyl)-1H-pyrazolo[3,4-b]pyridine Under nitrogen 5-bromo-3-iodo-1H-pyrazolo[3,4-b]pyridine (2.68 g, 8.27 mmol) was dissolved in anhydrous DMF (40 mL). The solution was cooled to 0-5° C. and an excess of dry sodium hydride added until further addition does not result in hydrogen formation. To the resulting suspension was added 2-trimethylsilanyl-ethoxymethylchloride (2.5 ml, 14 mmol) drop wise at 0-5° C. The resulting mixture was stirred at 0° C. for 1 h and thereafter quenched by addition of methanol and subsequently of a saturated aqueous solution of ammonium chloride. The mixture was then concentrated to dryness at 50° C. under reduced pressure. The resulting residue was distributed between water, brine and dichloromethane. The aqueous phase was then extracted with dichloromethane and the combined organic phases were dried over sodium sulfate, filtered and concentrated. The crude product was purified by flash silica gel chromatography using a gradient of ethyl acetate in hexanes to afford 5-bromo-3-iodo-1-(2-trimethylsilanyl-ethoxymethyl)-1H-pyrazolo[3,4-b]pyridine (2.929 g, 78% yield) as a beige to brown solid. $^1$H-NMR (500 MHz, $d_6$-DMSO) δ 8.85 (d, 1H), 8.40 (d, 1H), 5.85 (s, 2H), 3.69 (t, 2H), 0.92 (t, 2H), 0.11 (s, 9H).

Step 6: Synthesis of 5-bromo-3-(2-methoxy-phenyl)-1-(2-trimethylsilanyl-ethoxymethyl)-1H-pyrazolo[3,4-b]pyridine A mixture of 5-bromo-3-iodo-1-(2-trimethylsilanyl-ethoxymethyl)-1H-pyrazolo[3,4-b]pyridine (1.606 g, 3.537 mmol), 2-methoxy-phenyl-boronic acid (575 mg, 3.78 mmol) and of 1,1'-bis(diphenylphosphino)ferrocenepalladium(II)-dichloride dichlormethane adduct (145 mg, 0.178 mmol) in acetonitrile (8 mL) and aqueous solution of sodium carbonate (2M, 8 mL) was stirred in a closed vial at 85° C. for 100 min. The resulting mixture was then distributed between a saturated aqueous solution of sodium bicarbonate and dichloromethane and the aqueous phase extracted three times with dichloromethane. The combined organic phases were dried over sodium sulfate, filtered and concentrated. The crude product was purified by flash silica gel chromatography using a gradient of ethyl acetate in hexanes to afford 5-bromo-3-(2-methoxy-phenyl)-1-(2-trimethylsilanyl-ethoxymethyl)-1H-pyrazolo[3,4-b]pyridine (1.002 g, 65% yield) as an off-white oil. $^1$H-NMR (500 MHz, $d_6$-DMSO) δ 8.70 (d, 1H), 8.40 (d, 1H), 7.61 (d, 1H), 7.50 (ddd, 1H), 7.23 (dd, 1H), 7.10 (ddd, 1H), 5.81 (s, 2H), 3.85 (s, 3H), 3.66 (t, 2H), 0.84 (t, 2H), −0.10 (s, 9H). MS: m/z 456, 458 [MNa$^+$].

Step 7: Synthesis of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine Bis(pinacolato)diboron (1.20 g, 4.73 mmol), 1,1'-bis(diphenylphosphino)ferrocenepalladium(II)-dichloride dichlormethane adduct (100 mg, 0.122 mmol) and anhydrous sodium acetate (625 mg, 7.62 mmol) were placed in a nitrogen flushed vial. To this was added a solution of 5-bromo-3-(2-methoxy-phenyl)-1-(2-trimethylsilanyl-ethoxymethyl)-1H-pyrazolo[3,4-b]pyridine (1.002 g, 2.307 mmol) in anhydrous DMF (15 mL). The resulting mixture was irradiated in a Personal Chemistry Optimizer at 130° C. for 60 min and then concentrated at 50° C. under reduced pressure. The resulting residue was distributed between ether and brine and the aqueous phase was extracted with ether. The organic phases were combined, dried over sodium sulfate, filtered and concentrated. The crude product was then purified by flash silica gel chromatography using a gradient of ethyl acetate in hexanes to afford 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (1.370 g, 123% yield) as a pale olive-green solid. $^1$H-NMR (500 MHz, $d_6$-DMSO) 68.76 (d, 1H), 8.40 (d, 1H), 7.59 (dd, 1H), 7.51 (ddd, 1H), 7.25 (m, 1H), 7.12 (ddd, 1H), 5.84 (s, 2H), 3.82 (s, 3H), 3.67 (t, 2H), 1.33 (s, 12H), 0.84 (t, 2H), −0.10 (s, 9H).

Step 8: Synthesis of {2-hydroxy-5-[3-(2-methoxy-phenyl)-1H-pyrazolo[3,4-b]pyridin-5-yl]-phenyl}-morpholin-4-yl-methanone A mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (100 mg, 0.21 mmol), (5-bromo-2-hydroxy-phenyl)-morpholin-4-yl-methanone (66 mg (0.23 mmol) and 1,1'-bis(diphenylphosphino)ferrocenepalladium(II)-dichloride dichlormethane adduct (9 mg, 11 µmol) in acetonitrile (2 mL) and aqueous solution of sodium carbonate (2M, 2 mL) was irradiated in a Personal Chemistry Optimizer at 135° C. for 20 min. The crude reaction mixture was distributed between dichloromethane and a saturated aqueous solution of sodium bicarbonate. The aqueous phase was then extracted with dichloromethane and the combined organic phases were dried over sodium sulfate, filtered and concentrated. The crude product was then purified by flash silica gel chromatography using a gradient of ethyl acetate in hexanes to afford {2-hydroxy-5-[3-(2-methoxy-phenyl)-1-(2-trimethylsilanyl-ethoxymethyl)-1H-pyrazolo[3,4-b]pyridin-5-yl]-phenyl}-morpholin-4-yl-methanone (35 mg, 30% yield) as a colorless solid. $^1$H-NMR (500 MHz, d$_6$-DMSO) δ 8.86 (d, 1H), 8.27 (d, 1H), 7.64 (dd, 1H), 7.62 (dd, 1H), 7.54 (d, 1H), 7.49 (ddd, 1H), 7.24 (d, br, 1H), 7.11 (ddd, 1H), 7.00 (d, 1H), 5.84 (s, 2H), 3.84 (s, 3H), 3.69 (t, 2H), 3.7-3.2 (m, 8H), 0.86 (t, 2H), −0.08 (s, 9H). MS: m/z 583 [MNa$^+$], 561 [MH$^+$], 443 [MH$^+$-(Me$_3$Si(CH$_2$)$_2$O)]

A solution of {2-hydroxy-5-[3-(2-methoxy-phenyl)-1-(2-trimethylsilanyl-ethoxymethyl)-1H-pyrazolo[3,4-b]pyridin-5-yl]-phenyl}-morpholin-4-yl-methanone (34 mg, 61 µmol) in dichloromethane (15 mL) was cooled to 0-5° C. and boron trifluoride diethyl etherate (100 µl, 0.8 mmol) was added. The mixture was then stirred at 0-5° C. for 40 min before 10 ml of a 10% (w/v) solution of potassium hydroxide was added. The mixture was further stirred at room temperature for 1 h. The pH was then adjusted to approximately 3-4 by addition of citric acid and the aqueous phase saturated with sodium sulfate. The resulting mixture was extracted dichloromethane (3×). The organic phases were combined, washed with a saturated aqueous solution of sodium bicarbonate, dried over sodium sulfate and evaporated to afford {2-hydroxy-5-[3-(2-methoxy-phenyl)-1H-pyrazolo[3,4-b]pyridin-5-yl]-phenyl}-morpholin-4-yl-methanone (11.5 mg, 44% yield) as a colorless solid. $^1$H-NMR (500 MHz, d$_6$-DMSO) δ 13.76 (s, 1H), 10.06 (s, 1H), 8.78 (d, 1H), 8.23 (d, 1H), 7.64 (dd, 1H), 7.62 (dd, 1H), 7.51 (d, 1H), 7.46 (ddd, 1H), 7.22 (d, 1H), 7.10 (t, 1H), 6.99 (d, 1H), 3.84 (s, 3H), 3.7-3.2 (m, 8H). MS: m/z 431 [MH$^+$].

Other Compounds Prepared by Method 1:

TABLE 1

Structure

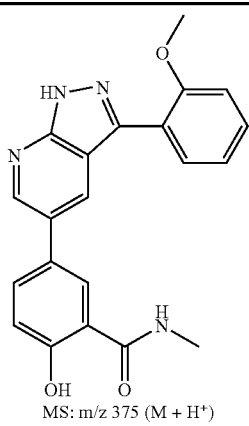

MS: m/z 375 (M + H$^+$)

Method 2:

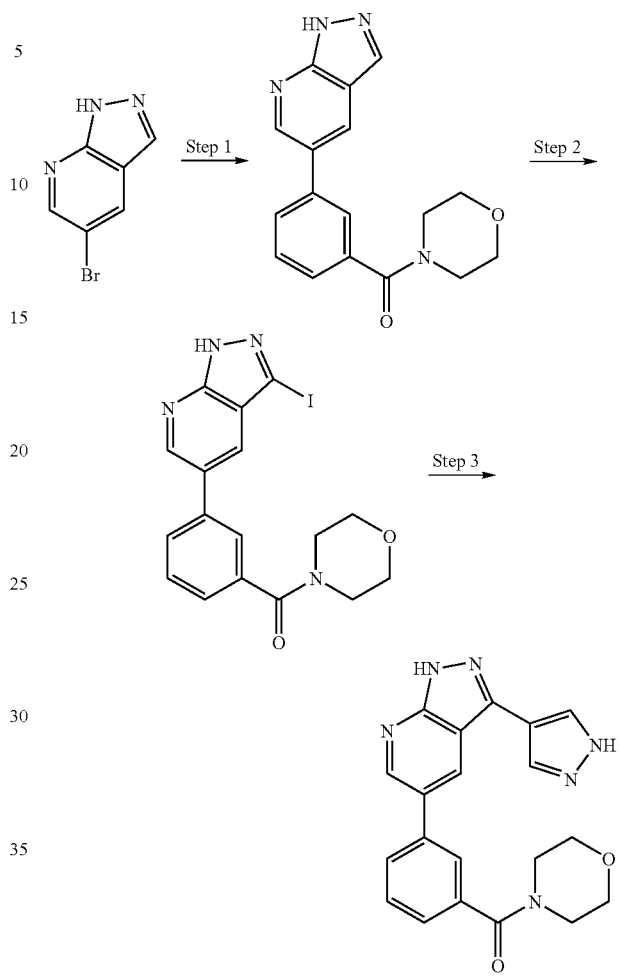

Step 1: Synthesis of morpholin-4-yl-[3-(1H-pyrazolo[3,4-b]pyridin-5-yl)-phenyl]-methanone A mixture of 5-bromo-1H-pyrazolo[3,4-b]pyridine (1.50 g, 7.57 mmol), 3-(morpholin-4-carbonyl)phenylboronic acid (2.136 g, 9.09 mmol) and tetrakis(triphenylphosphine)palladium(0) (435 mL, 0.376 mmol) in dimethoxyethane (8 mL) and saturated aqueous solution of sodium bicarbonate (8 mL) was irradiated in a Personal Chemistry Optimizer at 175° C. for 60 min. The crude reaction mixture was distributed between dichloromethane and a saturated aqueous solution of sodium bicarbonate. The aqueous phase was then extracted with dichloromethane, and then ethyl acetate and the combined organic phases were dried over sodium sulfate, filtered and concentrated to afford a pale green foam containing 80% of morpholin-4-yl-[3-(1H-pyrazolo[3,4-b]pyridin-5-yl)-phenyl]-methanone (2.30 g, 80% yield) and 20% of triphenylphosphine oxide. $^1$H-NMR (500 MHz, d$_6$-DMSO) δ 13.75 (s, 1H), 8.87 (d, 1H), 8.54 (d, 1H), 8.21 (d, 1H), 7.85 (m, 1H), 7.77 (m, 1H), 7.58 (t, 1H), 7.41 (m, 1H).

Step 2: Synthesis of [3-(3-iodo-1H-pyrazolo[3,4-b]pyridin-5-yl)-phenyl]-morpholin-4-yl-methanone Morpholin-4-yl-[3-(1H-pyrazolo[3,4-b]pyridin-5-yl)-phenyl]-methanone (2.30 g, 80% pure, ~6 mmol) and of N-iodosuccinimide (2.50 g, 11.1 mmol) were dissolved in dichloroethane (180 mL). The mixture was stirred under reflux conditions for 5 h, then cooled to room temperature and diluted with dichloromethane. The solution was washed with saturated aqueous solution of sodium thiosulfate (1×) and then with a saturated aqueous solution of sodium bromide (2×), dried over sodium sulfate, filtered and concentrated. The resulting residue was washed with ether (80 mL) and dried to afford [3-(3-iodo-1H-pyrazolo[3,4-b]pyridin-5-yl)-phenyl]-morpholin-4-yl-methanone as a beige powder (2.881 g, 88% yield over two steps). $^1$H-NMR (500 MHz, d$_6$-DMSO) δ 14.19 (s, 1H), 8.92 (d, 1H), 8.14 (d, 1H), 7.91 (m, 1H), 7.83 (m, 1H), 7.59 (ddd, 1H), 7.44 (dt, 1H), 3.75-3.35 (m, 8H).

Step 3: Synthesis of morpholin-4-yl-{3-[3-(1H-pyrazol-4-yl)-1H-pyrazolo[3,4-b]pyridin-5-yl]-phenyl}-methanone A mixture of [3-(3-iodo-1H-pyrazolo[3,4-b]pyridin-5-yl)-phenyl]-morpholin-4-yl-methanone (25 mg, 58 µmol), 1,1'-bis(diphenylphosphino)ferrocenepalladium(II)-dichloride dichlormethane adduct (5 mg, 6 µmol) and 1H-pyrazol-4-ylboronic acid (11 mg, 98 µmol) in acetonitrile (2 mL) and 2 M solution of sodium carbonate (1 mL) was irradiated in a Personal Chemistry Optimizer at 175° C. for 30 min. The crude reaction mixture was diluted with water (1 mL) and ethyl acetate (3 mL) and the organic phase separated, filtered and concentrated. The resulting crude mixture was then purified by mass-triggered reverse phase HPLC using a gradient of acetonitrile in water containing 0.1% of formic acid to afford morpholin-4-yl-{3-[3-(1H-pyrazol-4-yl)-1H-pyrazolo[3,4-b]pyridin-5-yl]-phenyl}-methanone (6.2 mg, 29% yield) of as a colorless powder. $^1$H-NMR (500 MHz, d$_6$-DMSO) δ 13.59 (s, 1H), 13.17 (s, 1H), 8.87 (d, 1H), 8.73 (d, 1H), 8.60 (s, br, 1H), 8.17 (s, br, 1H), 7.95 (ddd, 1H), 7.89 (t, 1H), (t, 1H), 7.59 (t, 1H), 7.43 (ddd, 1H), 3.80-3.35 (m, 8H). MS: m/z 397 [MNa$^+$], 375 [MH$^+$].

Other compounds prepared by Method 2:

TABLE 2

| Structure |
| --- |
| 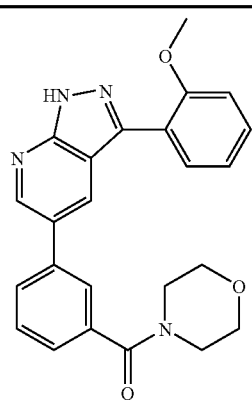 |
| MS: m/z 415 (M + H$^+$) |

TABLE 2-continued

| Structure |
| --- |
| 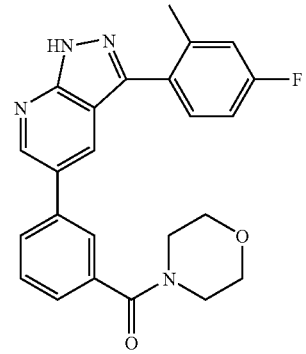 |
| MS: m/z 417 (M + H$^+$) |
| 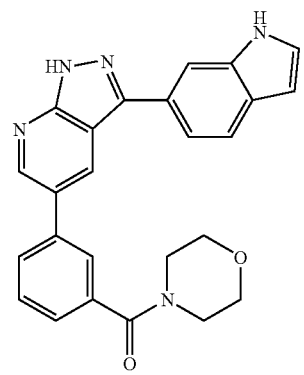 |
| MS: m/z 424 (M + H$^+$ |
| 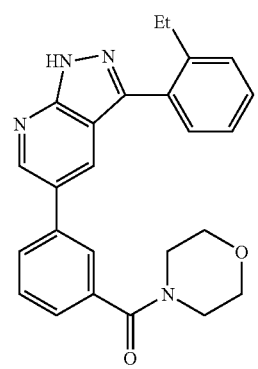 |
| MS: m/z 413 (M + H$^+$ |

TABLE 2-continued
Structure
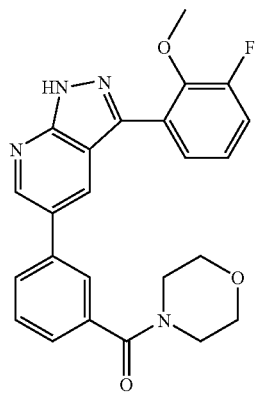
MS: m/z 433 (M + H+)
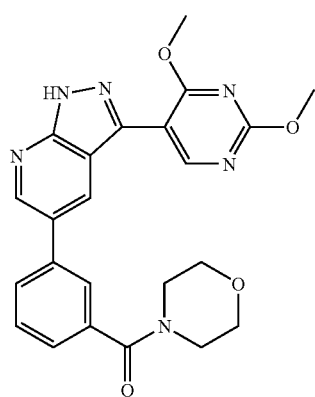
MS: m/z 447 (M + H+)
MS: m/z 429 (M + H+)
TABLE 2-continued
Structure
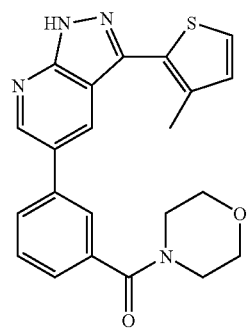
MS: m/z 405 (M + H+)
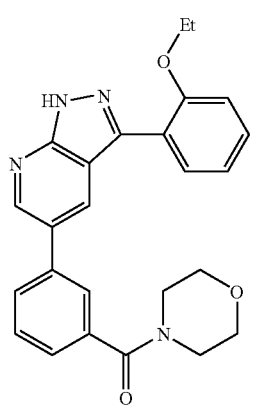
MS: m/z 429 (M + H+)
Method 3:
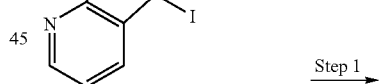
Step 1 →
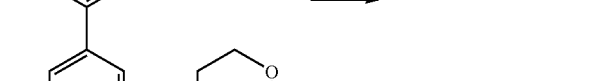
Step 2 →

-continued

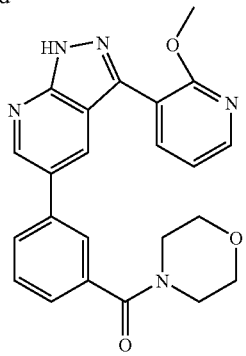

Step 1: Synthesis of {3-[3-Iodo-1-(2-trimethylsilanyl-ethoxymethyl)-1H-pyrazolo[3,4-b]pyridin-5-yl]-phenyl}-morpholin-4-yl-methanone To a solution of [3-(3-iodo-1H-pyrazolo[3,4-b]pyridin-5-yl)-phenyl]-morpholin-4-yl-methanone (2.12 g, 4.88 mmol) in anhydrous DMF (30 mL) was added sodium hydride (60% in mineral oil, 750 mg, 30 mmol) at 0-5° C. The mixture was stirred for a few minutes before trimethylsilylethoxymethyl chloride (2.0 ml, 11 mmol) was added drop wise at the same temperature. The mixture was stirred at 0° C. to room temperature for 4 hours and then cooled to 0-5° C. and quenched by an addition of methanol. The resulting suspension was then distributed between water, saturated aqueous ammonium chloride solution and ether. The aqueous phase was extracted three times with ether and the combined organic phases were dried over sodium sulfate, filtered and concentrated. The crude product was then purified by silica gel chromatography using a gradient of ethyl acetate in hexanes to afford {3-[3-iodo-1-(2-trimethylsilanyl-ethoxymethyl)-1H-pyrazolo[3,4-b]pyridin-5-yl]-phenyl}-morpholin-4-yl-methanone as a beige-brown foam (1.806 g, 66% by $^1$H-NMR, side product identified as morpholin-4-yl-{3-[2-(2-trimethylsilanyl-ethoxymethyl)-2H-pyrazolo[3,4-b]pyridin-5-yl]-phenyl}-methanone). $^1$H-NMR (500 MHz, d$_6$-DMSO) δ 9.08 (d, 1H), 8.29 (d, 1H), 8.01 (m, 1H), 7.95 (t, br, 1H), 7.69 (t, 1H), 7.55 (d, br, 1H), 5.88 (s, 2H), 3.71 (t, 2H), 3.85-3.45 (m, 8H), 0.94 (t, 2H), −0.2 (s, 9H). MS: m/z 565 [MNa$^+$], 537 [MH$^+$], 447 [MH$^+$-(Me$_3$Si(CH$_2$)$_2$O)].

Step 2: Synthesis of {3-[3-(2-methoxy-pyridin-3-yl)-1H-pyrazolo[3,4-b]pyridin-5-yl]-phenyl}-morpholin-4-yl-methanone A mixture of {3-[3-iodo-1-(2-trimethylsilanyl-ethoxymethyl)-1H-pyrazolo[3,4-b]pyridin-5-yl]-phenyl}-morpholin-4-yl-methanone (33 mg, 66% pure, 38 μmol), 1,1'-bis(diphenylphosphino)ferrocenepalladium(II)-dichloride dichlormethane adduct (5 mg, 6 μmol) and 3-trifluoromethylphenylboronic acid (14 mg, 92 μmol) in acetonitrile (2 mL) and 2 M solution of sodium carbonate (1 mL) was irradiated in a Personal Chemistry Optimizer at 175° C. for 20 min. The crude reaction mixture was diluted with saturated aqueous solution of sodium bromide (1 mL) and ethyl acetate (4 mL) and the organic phase separated, adsorbed onto silica and purified by flash silica gel chromatography using a gradient of ethyl acetate in hexanes to afford {3-[3-(2-methoxy-pyridin-3-yl)-1-(2-trimethylsilanyl-ethoxymethyl)-1H-pyrazolo[3,4-b]pyridin-5-yl]-phenyl}-morpholin-4-yl-methanone (24 mg, 116% yield) as an off-white residue. MS: m/z 568 [MNa$^+$], 546 [MH$^+$], 428 [MH$^+$-(Me$_3$Si(CH$_2$)$_2$O)]

This residue was dissolved in THF (2 ml) and activated 4 Å molecular sieves were added to the mixture. Tetra-n-butylammonium fluoride in THF (1 M solution, 0.5 ml, 0.5 mmol) was added and the mixture stirred at 70° C. for 26 h. The mixture was cooled to room temperature and 1 ml of cation exchange resin (Amberlyst, Na$^+$-form) added and the mixture was shaken for 40 min. The resin and sieves were then filtered off, washing with dichloromethane and methanol and the filtrate obtained was concentrated. The residue was dissolved in ethyl acetate and purified by flash chromatography on silica gel using a gradient of ethyl acetate containing 15% (v/v) of methanol in ethyl acetate. The product fractions was combined, concentrated and purified by mass-triggered reverse phase HPLC using a gradient of acetonitrile in water containing 0.1% of formic acid to afford {3-[3-(2-methoxy-pyridin-3-yl)-1H-pyrazolo[3,4-b]pyridin-5-yl]-phenyl}-morpholin-4-yl-methanone (3.2 mg, 20% yield) as a colorless solid. $^1$H-NMR (500 MHz, d$_6$-DMSO) δ 14.01 (s, 1H), 8.91 (d, 1H), 8.51 (d, 1H), 8.31 (dd, 1H), 8.11 (dd, 1H), 7.87 (ddd, 1H), 7.80 (t, 1H), 7.59 (t, 1H), 7.43 (dt, 1H), 7.18 (dd, 1H), 3.97 (s, 3H), 3.70-3.35 (m, 8H). MS: m/z 416 [MH$^+$].

Other compounds prepared by Method 3:

TABLE 3

| Structure |
| --- |
| 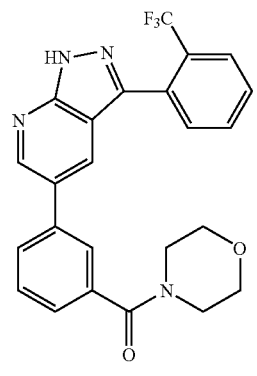<br>MS: m/z 453 (M + H$^+$) |
| 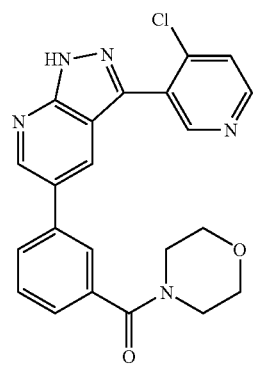<br>MS: m/z 420 (M + H$^+$) |

TABLE 3-continued

Structure

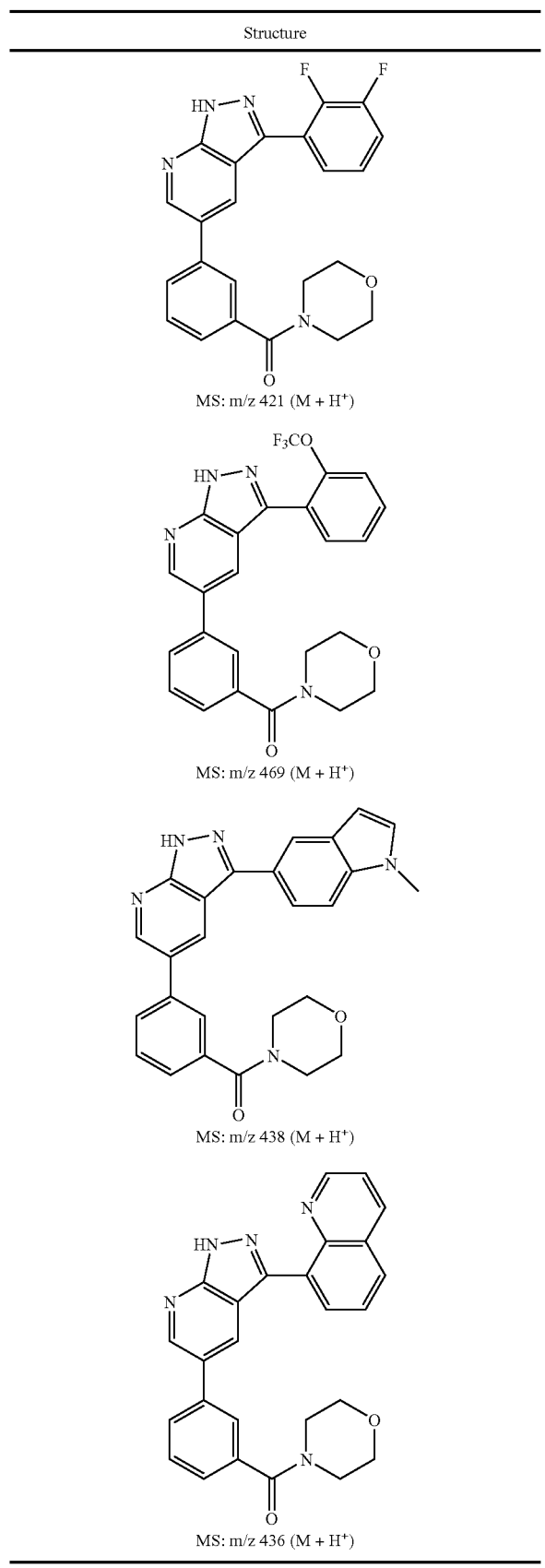

MS: m/z 421 (M + H+)

MS: m/z 469 (M + H+)

MS: m/z 438 (M + H+)

MS: m/z 436 (M + H+)

Method 4:

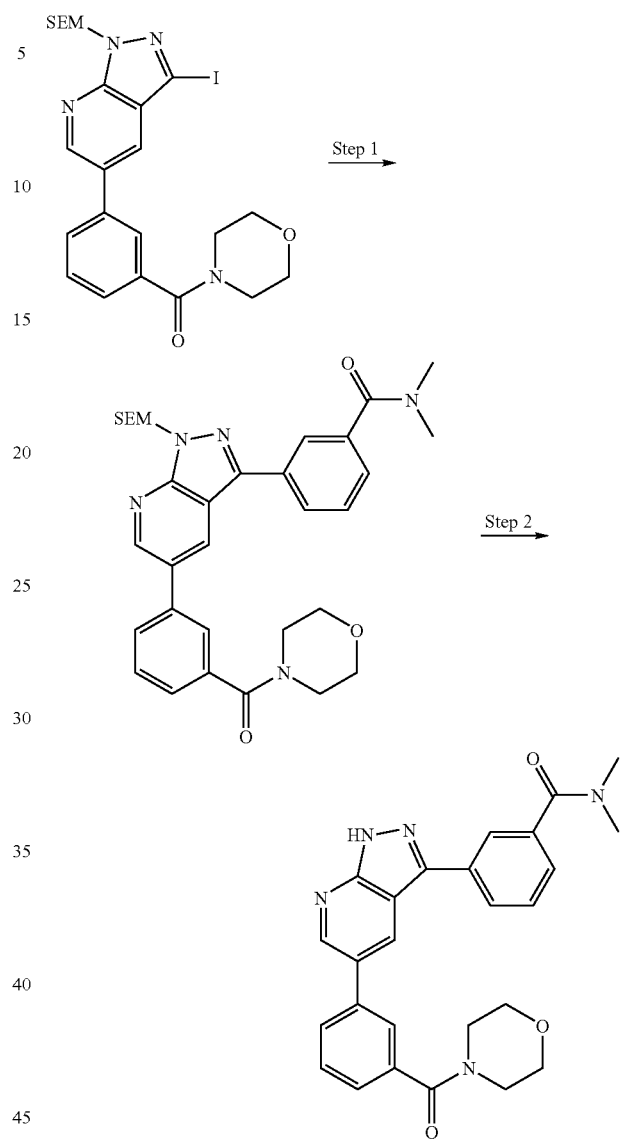

Step 1: Synthesis of N,N-dimethyl-3-(5-(3-(morpholine-4-carbonyl)phenyl)-1-((2-(trimethylsilyl)ethoxy)methyl)-1H-pyrazolo[3,4-b]pyridin-3-yl)benzamide A mixture of (3-(3-iodo-1-((2-(trimethylsilyl)ethoxy)methyl)-1H-pyrazolo[3,4-b]pyridin-5-yl)phenyl)(morpholino)methanone (50 mg, 0.089 mmol), 3-(dimethylcarbamoyl)phenylboronic acid (34 mg, 0.177 mmol), [1,1'-Bis(diphenylphosphino)ferrocene]dichloropalladium(II) complex with dichloromethane (3.6 mg, 0.0045 mmol) and sodium carbonate (2M aqueous solution, 0.134 mL, 0.267 mmol) in acetonitrile (1 mL) was heated in a Personal microwave at 90° C. for 30 min. The resulting mixture was diluted with water and extracted with ethyl acetate. The organic layers were combined, dried over sodium sulfate, filtered and concentrated to dryness. Silica gel chromatography purification of the crude product afford N,N-dimethyl-3-(5-(3-(morpholine-4-carbonyl)phenyl)-1-((2-(trimethylsilyl)ethoxy)

methyl)-1H-pyrazolo[3,4-b]pyridin-3-yl)benzamide as a clear oil. MS: m/z 586.2 [M+H+].

Step 2: Synthesis of N,N-dimethyl-3-(5-(3-(morpholine-4-carbonyl)phenyl)-1H-pyrazolo[3,4-b]pyridin-3-yl)benzamide A solution of N,N-dimethyl-3-(5-(3-(morpholine-4-carbonyl)phenyl)-1-((2-(trimethylsilyl)ethoxy)methyl)-1H-pyrazolo[3,4-b]pyridin-3-yl)benzamide in 5% of perchloric acid in acetic acid (1 mL) was stirred for 1 h at room temperature. Saturated sodium bicarbonate solution was then added to the solution slowly until pH ~8 and the mixture was stirred for 24 hours at room temperature. Ethyl acetate was then used for extraction and the organic layers were combined, dried over sodium sulfate, filtered and concentrated to dryness. Mass triggered reverse phase HPLC purification afforded N,N-dimethyl-3-(5-(3-(morpholine-4-carbonyl)phenyl)-1H-pyrazolo[3,4-b]pyridin-3-yl)benzamide (7.4 mg, 18% yield over two steps) as light yellow solids. $^1$H NMR (500 MHz, CDCl$_3$) δ 2.99 (s, 3H), 3.10 (s, 3H), 3.46 (br, 2H), 3.61 (br, 2H), 3.76 (br, 4H), 7.40 (d, J=7.0 Hz, 1H), 7.47 (d, J=8.0 Hz, 1H), 7.52 (m, 2H), 7.64 (d, J=7.5 Hz, 1H), 7.68 (s, 1H), 7.98 (m, 2H), 8.62 (s, 1H), 8.85 (br, 1H). MS: m/z 456.1 (M+H+).

Other Compounds Prepared by Method 4:

The conditions in step 2 may vary for the compounds in the following table. Sometimes sodium carbonate may be needed instead of sodium bicarbonate and the reaction time varies from 30 minutes to 24 hours.

TABLE 4

Structure

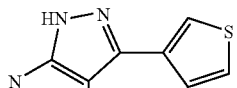

MS: m/z 405.1 (M + H+)

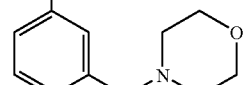

MS: m/z 449.0 (M + H+)

TABLE 4-continued

Structure

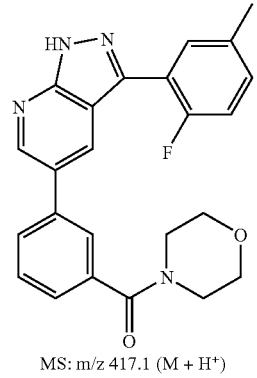

MS: m/z 417.1 (M + H+)

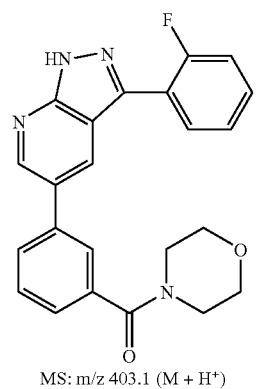

MS: m/z 403.1 (M + H+)

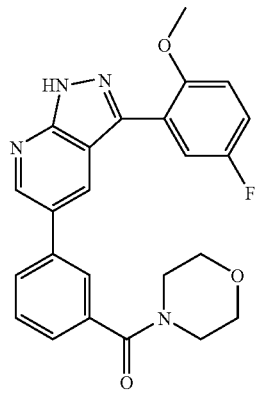

MS: m/z 433.1 (M + H+)

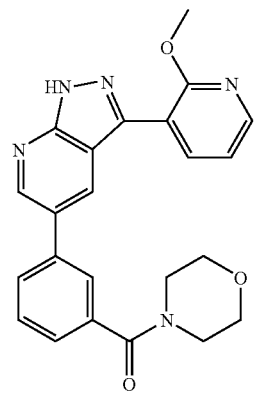

MS: m/z 416 (M + H+)

TABLE 4-continued
| Structure |
|---|
| 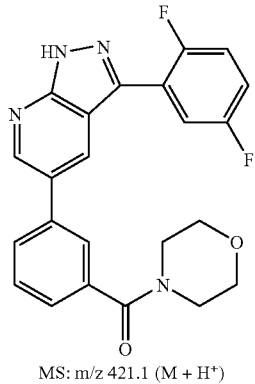 MS: m/z 421.1 (M + H⁺) |
| 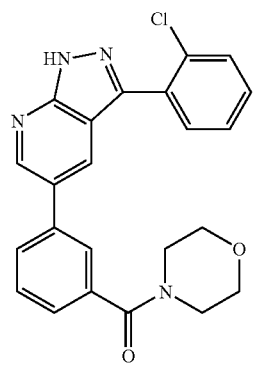 MS: m/z 419.1 (M + H⁺) |
| 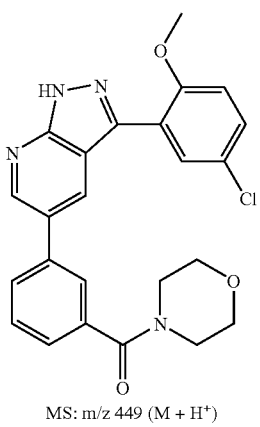 MS: m/z 449 (M + H⁺) |
| 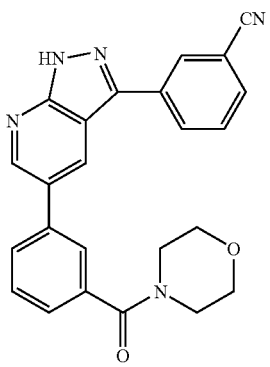 MS: m/z 410.1 (M + H⁺) |
TABLE 4-continued
| Structure |
|---|
| 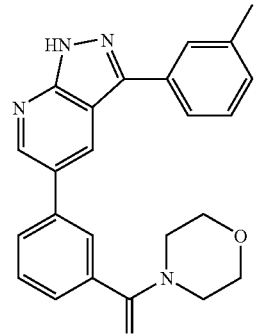 MS: m/z 399.1 (M + H⁺) |
| 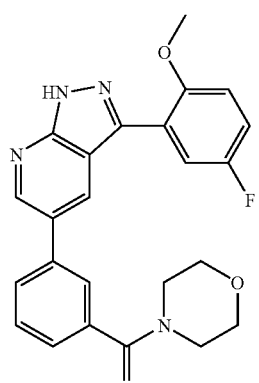 MS: m/z 433 (M + H⁺) |
| 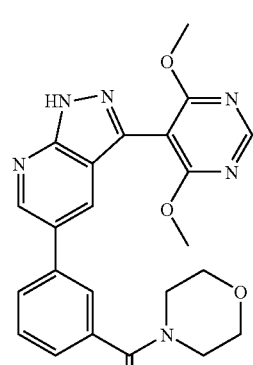 MS: m/z 447.1 (M + H⁺) |
| 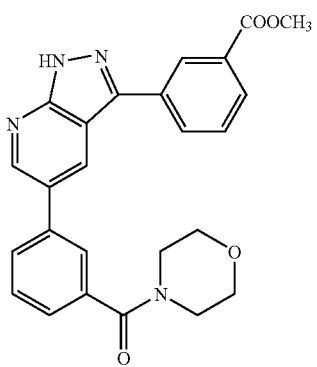 MS: m/z 443.1 (M + H⁺) |

TABLE 4-continued

| Structure |
|---|
| [Structure with pyrazolo[3,4-b]pyridine, methyl benzoate (COOCH₃), methoxy, and morpholine amide substituents]<br>MS: m/z 473.1 (M + H⁺) |
| [Structure with pyrazolo[3,4-b]pyridine, 5-chloro-2-fluorophenyl, and morpholine amide substituents]<br>MS: m/z 437.0 (M + H⁺) |
| [Structure with pyrazolo[3,4-b]pyridine, 3-(hydroxymethyl)phenyl, and morpholine amide substituents]<br>MS: m/z 415.1 (M + H⁺) |
| [Structure with pyrazolo[3,4-b]pyridine, 3-acetylphenyl, and morpholine amide substituents]<br>MS: m/z 427.1 (M + H⁺) |

TABLE 4-continued

| Structure |
|---|
| [Structure with pyrazolo[3,4-b]pyridine, 5-ethoxy-2-fluorophenyl, and morpholine amide substituents]<br>MS: m/z 447.1 (M + H⁺) |
| [Structure with pyrazolo[3,4-b]pyridine, 5-cyano-2-fluorophenyl, and morpholine amide substituents]<br>MS: m/z 428.0 (M + H⁺) |
| [Structure with pyrazolo[3,4-b]pyridine, 5-methoxy-2-fluorophenyl, and morpholine amide substituents]<br>MS: m/z 433.1 (M + H⁺). |
| [Structure with pyrazolo[3,4-b]pyridine, 2,5-dichlorophenyl, and morpholine amide substituents]<br>MS: m/z 453.0 (M + H⁺) |

Method 5:

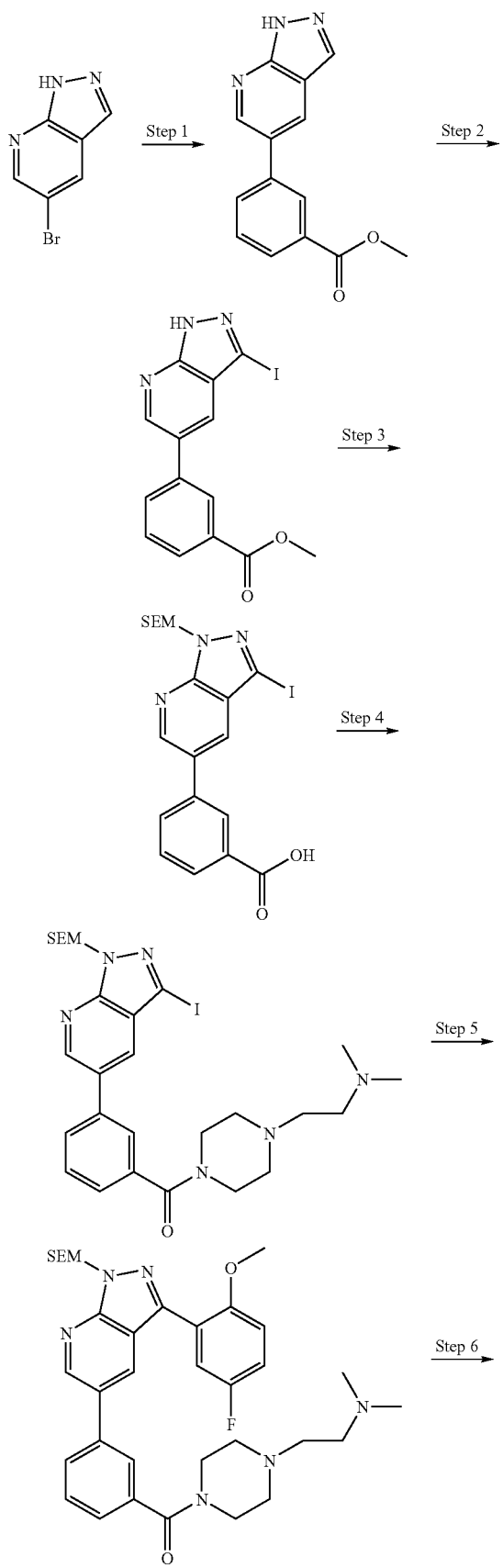

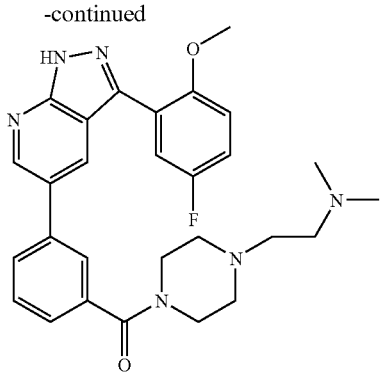

Step 1: Synthesis of methyl
3-(1H-pyrazolo[3,4-b]pyridin-5-yl)benzoate

A mixture of 5-bromo-1H-pyrazolo[3,4-b]pyridine (2.00 g, 10.10 mmol), 3-(methoxycarbonyl)phenylboronic acid (2.20 g, 12.12 mmol), sodium bicarbonate (2.2 g, 6.00 mmol), and tetrakis(triphenylphosphine)palladium(0) (0.250 g, 0.202 mmol) in dioxane/water (40 mL/10 mL) was stirred at 110° C. for 15 hours. The mixture was then poured into ice water and extracted with ethyl acetate (3×). The organic layers were combined, dried over sodium sulfate, filtered and concentrated to dryness. Silica gel chromatography of the crude product afforded methyl 3-(1H-pyrazolo[3,4-b]pyridin-5-yl)benzoate (8) (1.65 g, 65% yield) as yellow solids. MS: m/z 254.0 (M+H$^+$).

Step 2: Synthesis of methyl
3-(3-iodo-1H-pyrazolo[3,4-b]pyridin-5-yl)benzoate

To a solution of methyl 3-(1H-pyrazolo[3,4-b]pyridin-5-yl)benzoate (1.65 g, 6.52 mmol) in dichloroethane (40 mL) was added NIS (1.81 g, 8.04 mmol) and the mixture was stirred at 70° C. for 6 hours. The solvent was removed by reduced pressure and the crude product was purified by silica gel chromatography to afforded methyl 3-(3-iodo-1H-pyrazolo[3,4-b]pyridin-5-yl)benzoate (9) (988 mg, 40% yield). MS: m/z 379.9 (M+H$^+$).

Step 3: Synthesis of 3-(3-iodo-1-((2-(trimethylsilyl)ethoxy)methyl)-1H-pyrazolo[3,4-b]pyridin-5-yl)benzoic acid To a solution of methyl 3-(3-iodo-1H-pyrazolo[3,4-b]pyridin-5-yl)benzoate (988 mg, 2.61 mmol) in DMF was added sodium hydride (60% in mineral oil, 525 mg, 13.03 mmol) at −40° C. The mixture was stirred for 60 minutes before SEMCl (920 μl, 5.22 mmol) was added. The reaction was warmed to room temperature and quenched with methanol and water. Acetic acid was then used to adjust the pH to 4-5. The mixture was then extracted with ethyl acetate (3×) and the organic layers were combined, dried over sodium sulfate, filtered and concentrated to dryness. Silica gel chromatography purification of the resulting crude product afforded 3-(3-iodo-1-((2-(trimethylsilyl)ethoxy)methyl)-1H-pyrazolo[3,4-b]pyridin-5-yl)benzoic acid (200 mg, 15% yield) as solids. MS: m/z 517.9 (M+Na$^+$).

Step 4: Synthesis of (4-(2-(dimethylamino)ethyl) piperazin-1-yl)(3-(3-iodo-1-((2-(trimethylsilyl) ethoxy)methyl)-1H-pyrazolo[3,4-b]pyridin-5-yl) phenyl)methanone A mixture of crude 3-(3-iodo-1-((2-(trimethylsilyl)ethoxy)methyl)-1H-pyrazolo[3,4-b]pyridin-5-yl)benzoic acid (200 mg, 0.404 mmol), N,N-dimethyl-2-(piperazin-1-yl)ethanamine (76 mg, 0.485 mmol), O-(7-azabenzotriazol-1-yl)-N,N,N',N'-tetramethyluronium hexafluorophosphate (185 mg, 0.485 mmol), triethyl amine (0.700 ml, 0.485 mmol) and in DMF (2 ml) was stirred at 90° C. in Personal Microwave for 1 hour. Water was then added to the mixture and extracted with ethyl acetate (3×). The organic layers were combined, dried over sodium sulfate, filtered and concentrated to dryness. Silica gel chromatography of the crude product afforded (4-(2-(dimethylamino)ethyl)piperazin-1-yl)(3-(3-iodo-1-((2-(trimethylsilyl)ethoxy)methyl)-1H-pyrazolo[3,4-b]pyridin-5-yl)phenyl)methanone (110 mg, 43% yield) as off-white solids. MS: m/z 635.1 (M+H$^+$).

Step 5: Synthesis of (4-(2-(dimethylamino)ethyl) piperazin-1-yl)(3-(3-(5-fluoro-2-methoxyphenyl)-1-((2-(trimethylsilyl)ethoxy)methyl)-1H-pyrazolo[3,4-b]pyridin-5-yl)phenyl)methanone A mixture of (4-(2-(dimethylamino)ethyl)piperazin-1-yl)(3-(3-iodo-1-((2-(trimethylsilyl)ethoxy)methyl)-1H-pyrazolo[3,4-b]pyridin-5-yl)phenyl)methanone (50 mg, 0.079 mmol), 5-fluoro-2-methoxyphenylboronic acid (20 mg, 0.118 mmol), [1,1'-Bis(diphenylphosphino)ferrocene]dichloropalladium(II) complex with dichloromethane (7.9 mg, 0.10 mmol) and sodium carbonate (2M aqueous solution, 0.119 mL, 0.237 mmol) in acetonitrile (1 mL) was heated in a Personal microwave at 90° C. for 30 min. The resulting mixture was diluted with water and extracted with ethyl acetate. The organic layers were combined, dried over sodium sulfate, filtered and concentrated to dryness. Silica gel chromatography purification of the crude product afford (4-(2-(dimethylamino)ethyl)piperazin-1-yl)(3-(3-(5-fluoro-2-methoxyphenyl)-1-((2-(trimethylsilyl)ethoxy)methyl)-1H-pyrazolo[3,4-b]pyridin-5-yl)phenyl)methanone as a light yellow oil. MS: m/z 633.3 (M+H$^+$).

Step 6: Synthesis of (4-(2-(dimethylamino)ethyl) piperazin-1-yl)(3-(3-(5-fluoro-2-methoxyphenyl)-1H-pyrazolo[3,4-b]pyridin-5-yl)phenyl)methanone A solution of (4-(2-(dimethylamino)ethyl)piperazin-1-yl)(3-(3-(5-fluoro-2-methoxyphenyl)-1-((2-(trimethylsilyl)ethoxy)methyl)-1H-pyrazolo[3,4-b]pyridin-5-yl)phenyl)methanone from Step 5 in 5% of perchloric acid in methanol (1 mL) was stirred for 45 minutes at room temperature. Sodium hydroxide solution (2M) was then added to the solution slowly until pH ~8. Ethyl acetate was then used for extraction and the organic layers were combined and concentrated to dryness, which was then redissolved in methanol (1 mL) and sodium carbonate (2M, 1 mL). The mixture was stirred at room temperature for 15 hours before being diluted with water and extracted with ethyl acetate (3×). The organic layers were combined, dried over sodium sulfate, filtered and concentrated to dryness. Mass triggered reverse phase HPLC purification afforded (4-(2-(dimethylamino)ethyl)piperazin-1-yl)(3-(3-(5-fluoro-2-methoxyphenyl)-1H-pyrazolo[3,4-b]pyridin-5-yl)phenyl)methanone (25.6 mg, 64% yield from 12) as white solids. $^1$H NMR (500 MHz, CD$_3$O)) δ 2.42 (s, 6H), 2.49 (br, 2H), 2.59 (m, 4H), 2.69 (m, 2H), 3.54 (br, 2H), 3.81 (br, 2H), 3.85 (s, 3H), 7.17 (m, 2H), 7.40 (dd, J=3.0, 9.5 Hz, 1H), 7.44 (d, br, J=7.5 Hz, 1H), 7.59 (t, J=7.5 Hz, 1H), 7.72 (br, 1H), 7.77 (d, J=8.5 Hz, 1H), 8.39 (d, J=1.5 Hz, 1H), 8.80 (d, J=2.5 Hz, 1H). MS: m/z 503.2 (M+H$^+$).

Method 6:

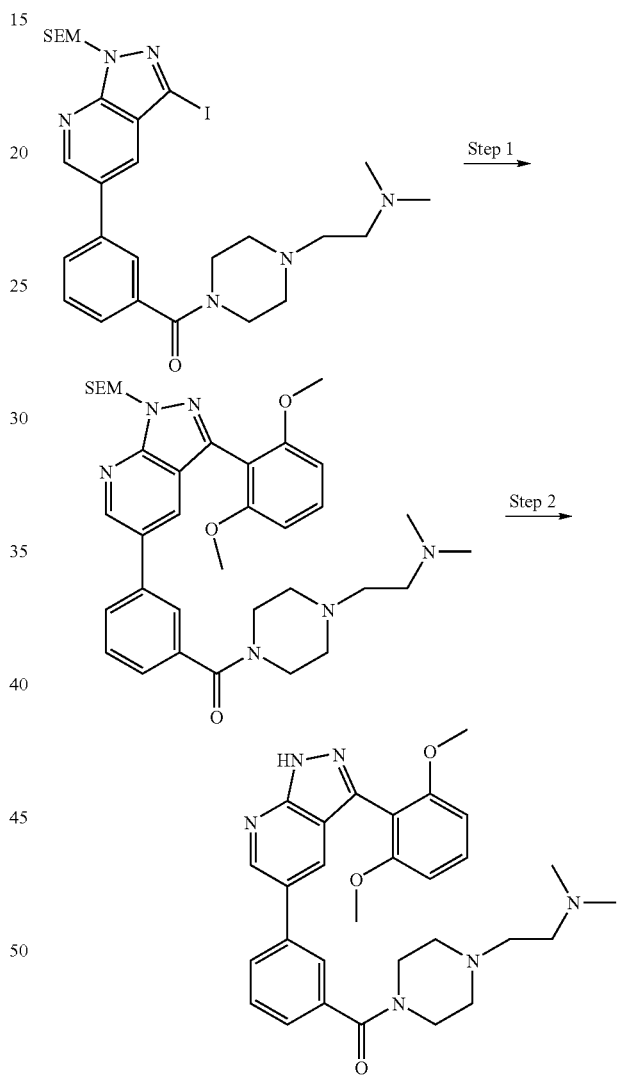

Step 1: Synthesis of (3-(3-(2,6-dimethoxyphenyl)-1-((2-(trimethylsilyl)ethoxy)methyl)-1H-pyrazolo[3,4-b]pyridin-5-yl)phenyl)(4-(2-(dimethylamino)ethyl) piperazin-1-yl)methanone A mixture of (4-(2-(dimethylamino)ethyl)piperazin-1-yl)(3-(3-iodo-1-((2-(trimethylsilyl)ethoxy)methyl)-1H-pyrazolo[3,4-b]pyridin-5-yl)phenyl)methanone (50 mg, 0.079 mmol), 2,6-dimethoxyphenylboronic acid (22 mg, 0.118 mmol), tetrakis(triphenylphosphine)palladium(0) (9.1 mg, 0.10 mmol) and sodium carbonate (2M aqueous solution, 0.119 mL, 0.237 mmol) in acetonitrile (1 mL) was heated in a Personal microwave at 120° C. for 30 min. The resulting mixture was diluted with water and extracted with ethyl acetate. The organic layers were combined, dried over sodium sulfate, filtered and concentrated to dryness. Silica gel chromatography purification of the crude product afford (3-(3-(2,6-dimethoxyphenyl)-1-((2-(trimethylsilyl)ethoxy)methyl)-1H-pyrazolo[3,4-b]pyridin-5-yl)phenyl)(4-(2-(dimethylamino)ethyl)piperazin-1-yl)methanone as a clear oil. MS: m/z 645.3 (M+H$^+$).

Step 2: Synthesis of (3-(3-(2,6-dimethoxyphenyl)-1H-pyrazolo[3,4-b]pyridin-5-yl)phenyl)(4-(2-(dimethylamino)ethyl)piperazin-1-yl)methanone A solution of (3-(3-(2,6-dimethoxyphenyl)-1-((2-(trimethylsilyl)ethoxy)methyl)-1H-pyrazolo[3,4-b]pyridin-5-yl)phenyl)(4-(2-(dimethylamino)ethyl)piperazin-1-yl)methanone in 5% of perchloric acid in acetic acid (1 mL) was stirred for 45 minutes at room temperature. Sodium hydroxide solution (2M) was then added to the solution slowly until pH ~8. Ethyl acetate was then used for extraction and the organic layers were combined and concentrated to dryness, which was then redissolved in methanol (1 mL) and sodium carbonate (2M, 1 mL). The mixture was stirred at room temperature for 15 hours before being diluted with water and extracted with ethyl acetate (3×). The organic layers were combined, dried over sodium sulfate, filtered and concentrated to dryness. Mass triggered reverse phase HPLC purification afforded (3-(3-(2,6-dimethoxyphenyl)-1H-pyrazolo[3,4-b]pyridin-5-yl)phenyl)(4-(2-(dimethylamino)ethyl)piperazin-1-yl)methanone (22.70 mg, 56% yield for two steps) as white solids. $^1$H NMR (500 MHz, CD$_3$OD) δ 2.48 (br, 2H), 2.52 (s, 6H), 2.60 (m, 4H), 2.69 (m, 2H), 3.51 (br, 2H), 3.74 (s, 6H), 3.80 (br, 2H), 6.80 (d, J=8.5 Hz, 2H), 7.43 (m, 2H), 7.56 (t, J=8.0 Hz, 1H), 7.69 (s, 1H), 7.75 (d, J=8.0 Hz, 1H), 8.09 (d, J=2 Hz, 1H), 8.81 (d, J=2 Hz, 1H). MS: m/z 515.2 (M+H$^+$).

Other Compounds Prepared by Method 6:

The conditions in step 2 may vary for the compounds in the following table. Sometimes sodium carbonate may be needed instead of sodium bicarbonate and the reaction time varies from 30 minutes to 24 hours.

TABLE 5

| Structure |
| --- |
| 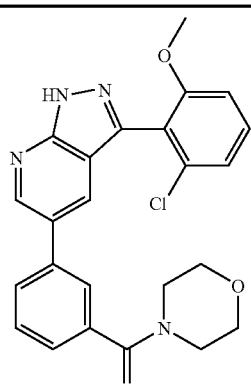<br>MS: m/z 449.1 (M + H$^+$) |

TABLE 5-continued

| Structure |
| --- |
| 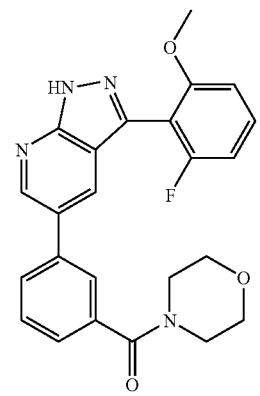<br>MS: m/z 433.1 (M + H$^+$) |
| 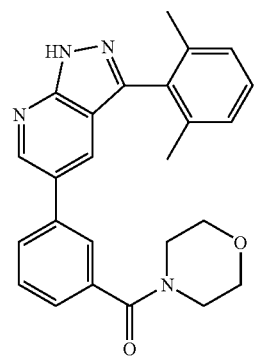<br>*<br>MS: m/z 413.1 (M + H$^+$) |
| 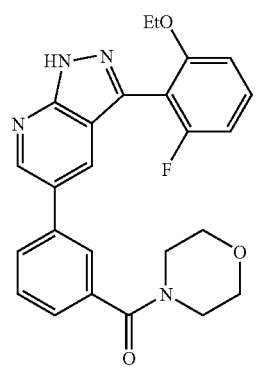<br>**<br>MS: m/z 447.1 (M + H$^+$) |

TABLE 5-continued

| Structure |
|---|
| [Structure with dichlorophenyl pyrazolopyridine and morpholine amide]<br>MS: m/z 453.0 (M + H⁺) *** |

\* Step 1 Suzuki coupling conditions: 150° C., 1 h, μw.
\*\* Step 1 Suzuki coupling conditions: 120° C., 1 h, μw.
\*\*\* Step 1 Suzuki coupling conditions: Pd$_2$(dba)$_3$, K$_3$PO$_4$, and dicyclohexylphenylphosphine, CH$_3$CN, 150° C., 4 h, μw.

Method 7:

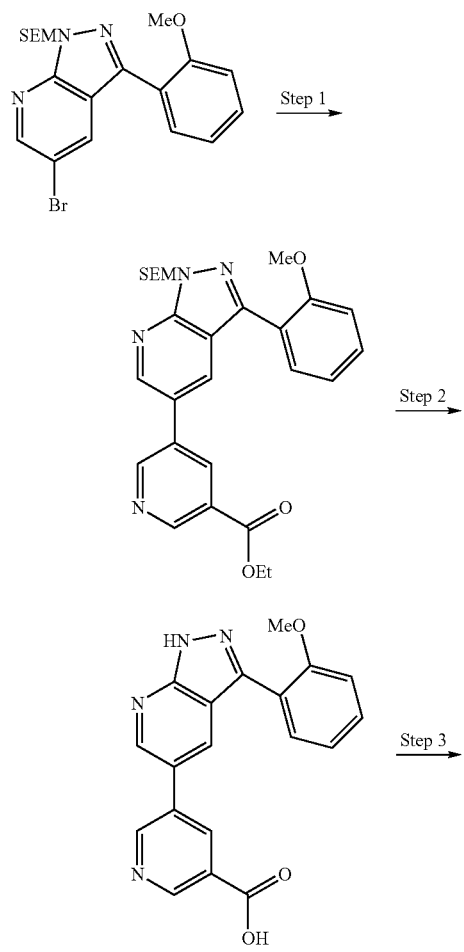

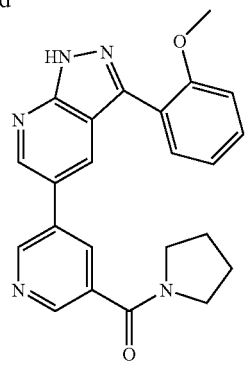

Step 1: Synthesis of 5-[3-(2-methoxy-phenyl)-1-(2-trimethylsilanyl-ethoxymethyl)-1H-pyrazolo[3,4-b]pyridin-5-yl]-nicotinic acid ethyl ester A mixture of 3-ethoxycarbonyl-5-pyridylboronic acid (529 mg, 1.91 mmol), 1,1'-bis(diphenylphosphino)ferrocene-palladium(II)-dichloride dichlormethane adduct (66 mg, 0.09 mmol) and 5-bromo-3-iodo-1-(2-trimethylsilanyl-ethoxymethyl)-1H-pyrazolo[3,4-b]pyridine (780 mg, 1.80 mmol) acetonitrile (5 mL) and 2 M aqueous solution of sodium carbonate (5 mL) were added and the mixture was irradiated in a Personal Chemistry Optimizer to 90° C. for 30 minutes. The crude reaction mixture was distributed between ethyl acetate and water. The aqueous phase was extracted three times with ethyl acetate and the combined organic phases were dried over sodium sulfate, filtered and concentrated. The crude product was purified by flash silica gel chromatography using a gradient of ethyl acetate in hexanes to afford 5-[3-(2-methoxy-phenyl)-1-(2-trimethylsilanyl-ethoxymethyl)-1H-pyrazolo[3,4-b]pyridin-5-yl]-nicotinic acid ethyl ester (552 mg, 61% yield) as a yellow oil. $^1$H-NMR (500 MHz, d$_6$-DMSO) δ 9.24 (d, 1H), 9.12 (d, 1H), 9.03 (d, 1H), 8.60 (t, 1H), 8.56 (d, 1H), 7.66 (dd, 1H), 7.51 (ddd, 1H), 7.25 (dd, 1H), 7.12 (dt, 1H), 5.88 (s, 2H), 4.40 (q, 2H), 3.87 (s, 3H), 3.71 (t, 2H), 1.37 (t, 3H), 0.87 (t, 2H), −0.073 (t, 9H). MS: m/z 505 [MH⁺].

Step 2: Synthesis of 5-[3-(2-methoxy-phenyl)-1H-pyrazolo[3,4-b]pyridin-5-yl]-nicotinic acid To a solution of 5-[3-(2-methoxy-phenyl)-1-(2-trimethyl-silanyl-ethoxymethyl)-1H-pyrazolo[3,4-b]pyridin-5-yl]-nicotinic acid ethyl ester (494 mg, 0.98 mmol) in THF (20 mL) was added tetra-n-butylammonium fluoride in THF (1M, 10 ml, 10 mmol) and activated 4 Å molecular sieves. The resulting mixture was stirred at 70° C. for 7 h. The sieves were filtered off, washing with ethyl acetate and the resulting filtrate concentrated. The residue was distributed between dichloromethane and water. The aqueous phase was extracted three times with dichloromethane and the organic phases combined, dried over sodium sulfate, filtered and concentrated to afford of 5-[3-(2-methoxy-phenyl)-1H-pyrazolo[3,4-b]pyridin-5-yl]-nicotinic acid (654 mg, 62% purity, 405 mg, 119% yield) as a brown solid. $^1$H-NMR (500 MHz, d$_6$-DMSO) δ 13.98 (s, 1H), 8.99 (d, 1H), 8.95 (s, 1H), 8.88 (d, 1H), 8.43 (t, 1H), 8.40 (d, 1H), 7.67 (dd, 1H), 7.47 (ddd, 1H), 7.23 (d, 1H), 7.10 (dt, 1H), 3.86 (s, 3H). MS: m/z 345 (96%) [M−H⁻].

Step 3: Synthesis of {5-[3-(2-methoxy-phenyl)-1H-pyrazolo[3,4-b]pyridin-5-yl]-pyridin-3-yl}-pyrrolidin-1-yl-methanone (5-[3-(2-methoxy-phenyl)-1H-pyrazolo[3,4-b]pyridin-5-yl]-nicotinic acid (350 mg, 62% pure, 0.63 mmol) was dissolved in anhydrous DMF (20 mL) at 50-60° C. and the solution was cooled to room temperature when PS-HOBt resin (Argonaut Technologies) (0.9 mmol·g$^{-1}$ loading, 2.20 g, 1.98 mmol), DMAP (32 mg, 0.26 mmol) and EDCI (375 mg, 1.95 mmol) were added. The mixture was shaken at room temperature for 16 h. The resin was filtered off, washing six times with DMF and subsequently three times with ether and dried. The resin and (5-[3-(2-methoxy-phenyl)-1H-pyrazolo[3,4-b]pyridin-5-yl]-nicotinate) (460 mg, theoretical loading 105 μmol) were suspended in anhydrous DMF (3 mL) containing pyrrolidine (110 μl, 1.3 mmol) and shaken for 22 h. The resin is filtered off, washing with dichloromethane, ether and DMF. The filtrate and washings were combined and concentrated. The resulting residue is purified by mass-triggered reverse phase HPLC using a gradient of acetonitrile in water containing 0.1% of formic acid to afford {5-[3-(2-methoxy-phenyl)-1H-pyrazolo[3,4-b]pyridin-5-yl]-pyridin-3-yl}-pyrrolidin-1-yl-methanone (2.4 mg, 6 μmol, 6% yield) as a light brown solid. $^1$H-NMR (500 MHz, d$_6$-MeOH) δ 68.98 (d, 1H), 8.87 (d, 1H), 8.74 (d, 1H), 8.50 (d, 1H), 8.31 (t, 1H), 7.67 (dd, 1H), 7.48 (ddd, 1H), 7.21 (d, 1H), 7.11 (dt, 1H), 3.89 (s, 3H), 3.65 (t, 2H), 3.58 (t, 2H), 2.02 (m, 2H), 1.96 (m, 2H). MS: m/z 400 [MH$^+$].

Other compounds prepared by Method 7:

TABLE 6

Structure

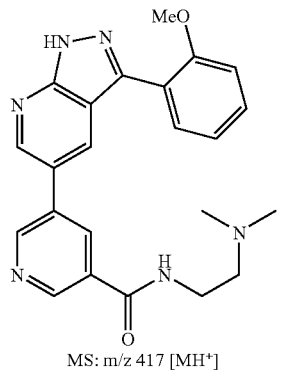

MS: m/z 417 [MH$^+$]

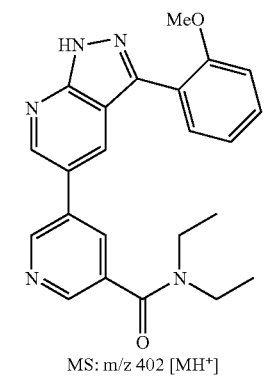

MS: m/z 402 [MH$^+$]

TABLE 6-continued

Structure

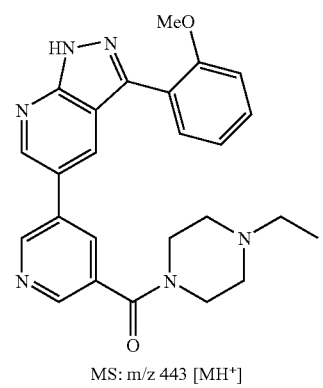

MS: m/z 443 [MH$^+$]

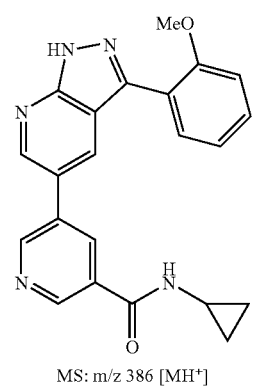

MS: m/z 386 [MH$^+$]

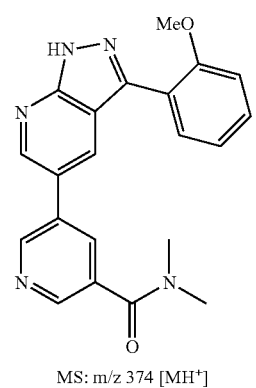

MS: m/z 374 [MH$^+$]

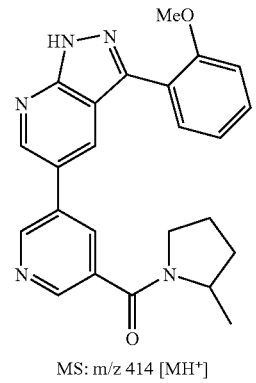

MS: m/z 414 [MH$^+$]

TABLE 6-continued
Structure
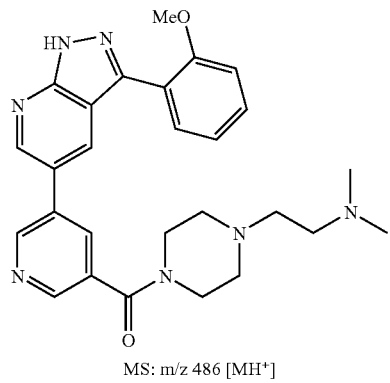
MS: m/z 486 [MH+]
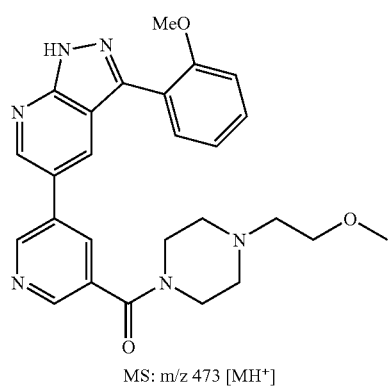
MS: m/z 473 [MH+]
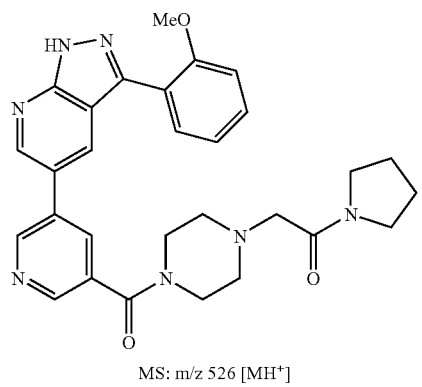
MS: m/z 526 [MH+]
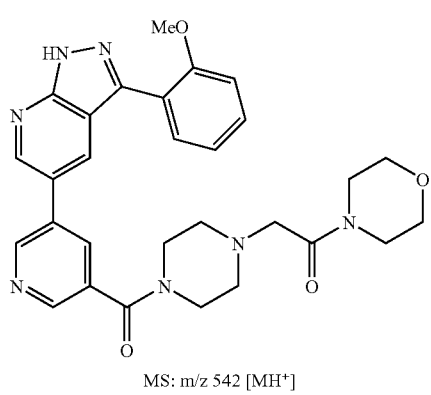
MS: m/z 542 [MH+]
TABLE 6-continued
Structure
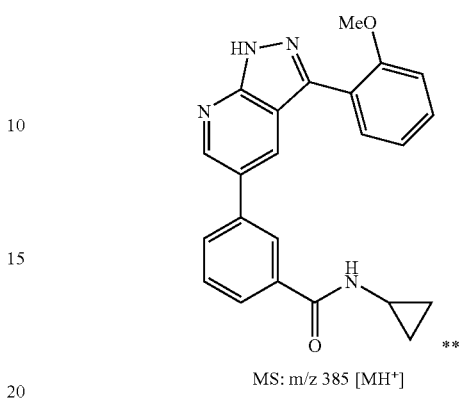
MS: m/z 385 [MH+] **
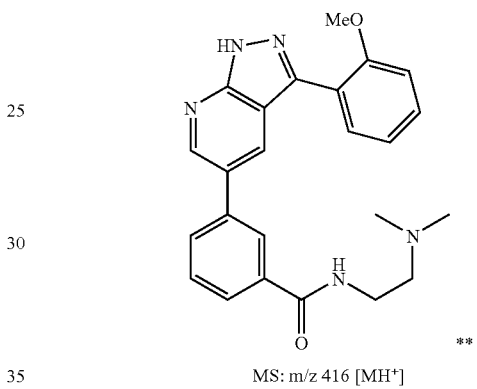
MS: m/z 416 [MH+] **
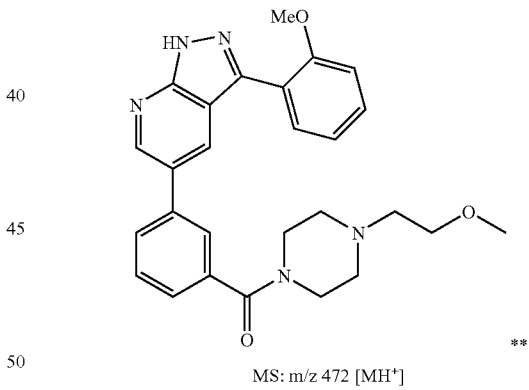
MS: m/z 472 [MH+] **
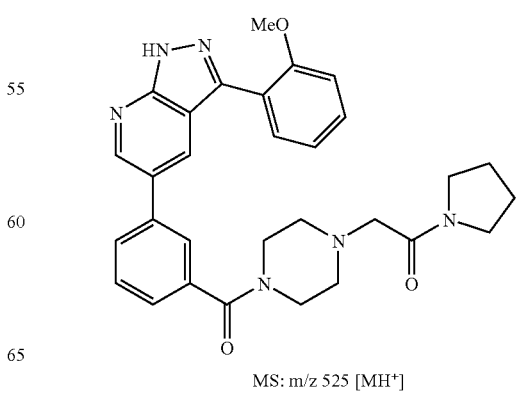
MS: m/z 525 [MH+] **

TABLE 6-continued
Structure
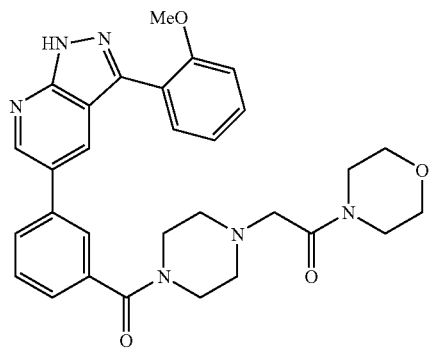
MS: m/z 541 [MH+]
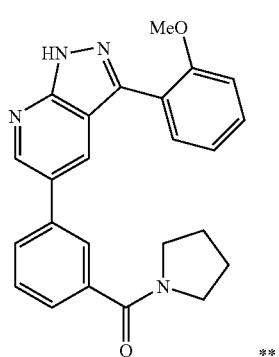
MS: m/z 399 [MH+]
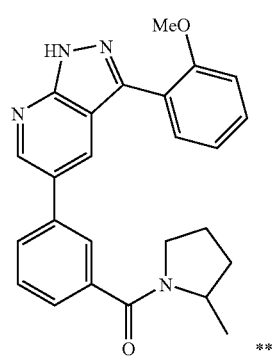
MS: m/z 413 [MH+]
TABLE 6-continued
Structure
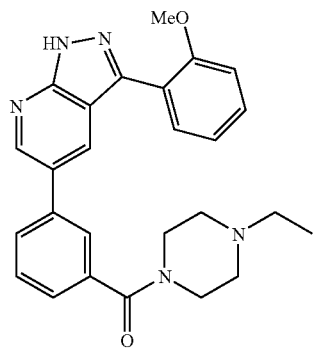
MS: m/z 442 [MH+]
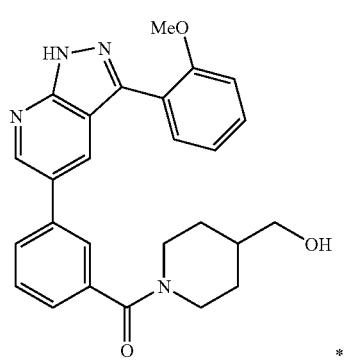
MS: m/z 443 [MH+]
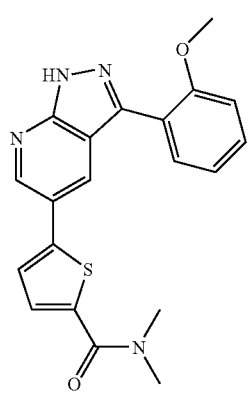
MS: m/z 379 [MH+]

TABLE 6-continued

Structure

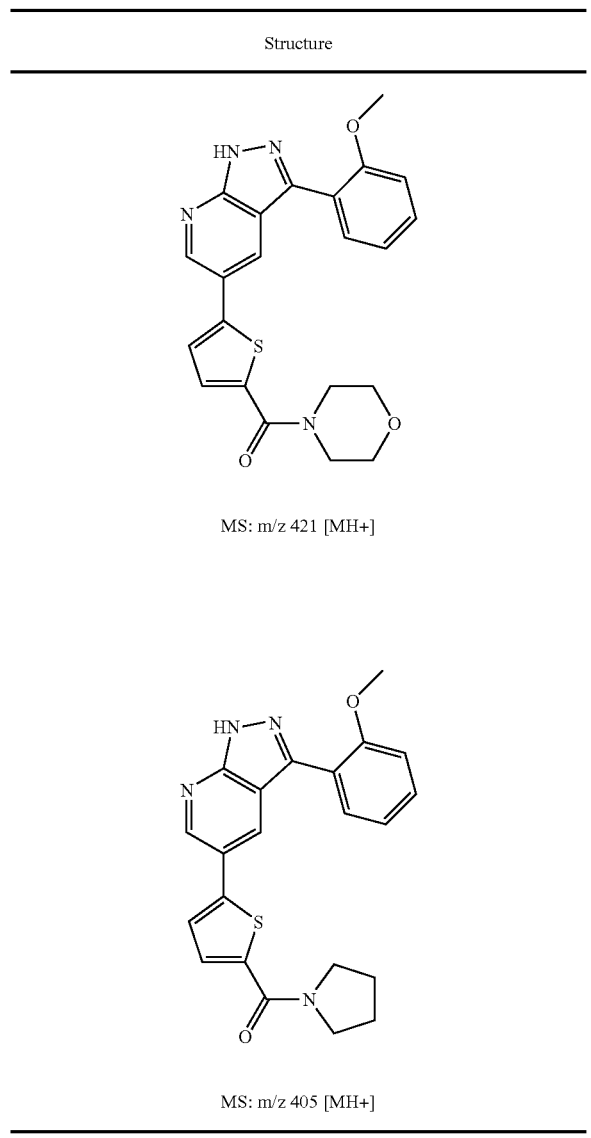

MS: m/z 421 [MH+]

MS: m/z 405 [MH+]

\* synthesized starting from 3-[3-(2-methoxy-phenyl)-1H-pyrazolo[3,4-b]pyridin-5-yl]-benzoic acid and purified by flash chromatography on silica gel using a gradient of 20% v/v methanol in ethyl acetate in hexanes \*\* synthesized starting from 3-[3-(2-methoxy-phenyl)-1H-pyrazolo[3,4-b]pyridin-5-yl]-benzoic acid Method 8:

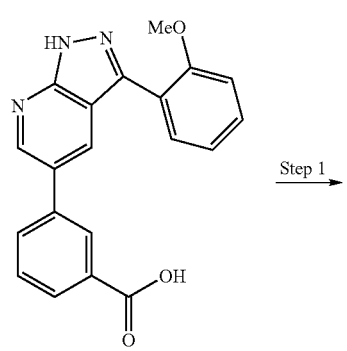

-continued

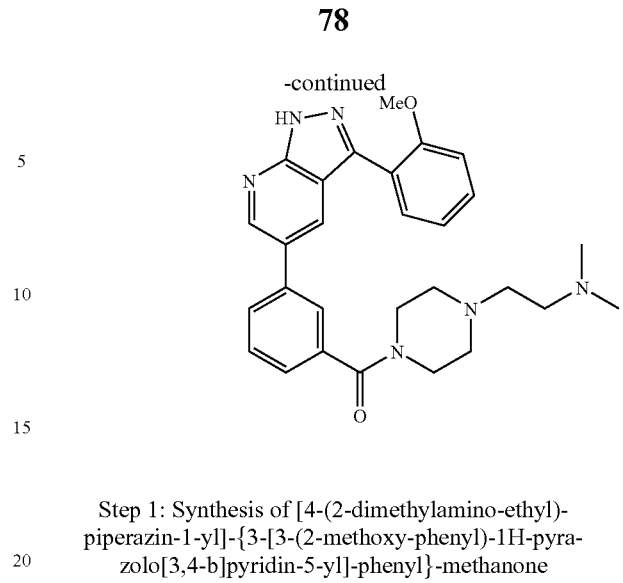

Step 1: Synthesis of [4-(2-dimethylamino-ethyl)-piperazin-1-yl]-{3-[3-(2-methoxy-phenyl)-1H-pyrazolo[3,4-b]pyridin-5-yl]-phenyl}-methanone 3-[3-(2-methoxy-phenyl)-1H-pyrazolo[3,4-b]pyridin-5-yl]-benzoic acid (338 mg, 0.79 mmol) and O-(7-azabenzotriazol-1-yl)-N,N,N',N'-tetramethyluronium hexafluorophosphate (300 mg, 0.79 mmol) were dissolved in a mixture of 20 ml of acetonitrile and 10 ml of methanol. 131 mg (0.83 mmol) of 1-(2-dimethylaminoethyl)-piperazine was added and the mixture stirred at ambient temperature for 6 h. The resulting mixture was distributed between dichloromethane and a 2 M aqueous solution of sodium carbonate. The phases were separated and the aqueous layer extracted three times with dichloromethane. The combined organic layers were combined, washed with a saturated aqueous solution of sodium bromide, dried over sodium sulfate, and evaporated. The crude material was purified by flash chromatography on silica gel using a stepped gradient of ethyl acetate and a 4:4:1 solvent mixture of ethyl acetate, dichloromethane and methanol containing 2% v/v of 35% wt ammonia in water to afford [4-(2-dimethylamino-ethyl)-piperazin-1-yl]-{3-[3-(2-methoxy-phenyl)-1H-pyrazolo[3,4-b]pyridin-5-yl]-phenyl}-methanone (160 mg, 42%) as an oil. $^1$H-NMR (d$_6$-CDCl$_3$) δ 8.87 (d) [1H], 8.36 (d) [1H], 7.75 (dd) [1H], 7.68 (t) [1H], 7.67 (m) [1H], 7.53 (m) [1H], 7.46 (mt) [1H], 7.42 (md) [1H], 7.13 (dt) [1H], 7.10 (d) [1H], 3.89 (s) [3H], 3.81-3.86 (m) [2H], 3.48-3.55 (m) [2H], 2.58-2.64 (m) [2H], 2.56 (m) [2H], 2.50 (m) [2H], 2.44-2.52 (m) [2H]. MS: m/z 485 (M+H$^+$).

Method 9:

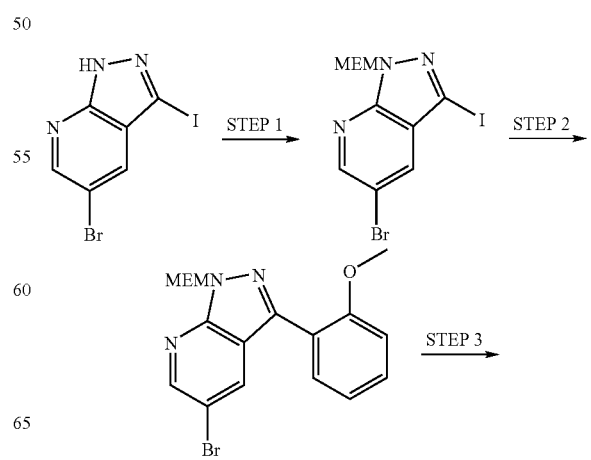

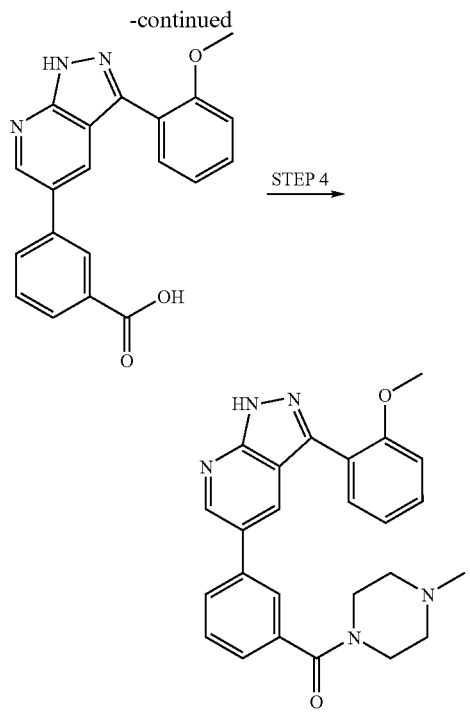

Step 1: Synthesis of 5-bromo-3-iodo-1-(2-methoxy-ethoxymethyl)-1H-pyrazolo[3,4-b]pyridine To a solution of 5-bromo-3-iodo-1H-pyrazolo[3,4-b]pyridine (470 mg, 1.45 mmol), 60% sodium hydride in mineral oil (104 mg, 4.35 mmol) and tetra-n-butylammonium iodide (134 mg, 0.36 mmol) in DMF (10 mL) was added methoxyethoxymethyl chloride (248 µl, 2.18 mmol) at room temperature and the mixture was stirred for 4 h at the same temperature and subsequently quenched by addition of methanol. The mixture was then distributed between ether and brine and the organic layer dried over sodium sulfate, filtered and concentrated. The crude product was purified by flash silica gel chromatography using a gradient of ethyl acetate in hexanes to afford 5-bromo-3-iodo-1-(2-methoxy-ethoxymethyl)-1H-pyrazolo[3,4-b]pyridine (254 mg, 0.69 mmol, 74% yield) as a colorless solid (1:1 mixture with regioisomer 5-bromo-3-iodo-2-(2-methoxy-ethoxymethyl)-1H-pyrazolo[3,4-b]pyridine). $^1$H-NMR (500 MHz, d$_6$-DMSO) isomer A (50%) δ 8.75 (d, 1H), 8.29 (d, 1H), 5.78 (s, 1H), 3.61-3.63 (m, 2H), 3.37-3.39 (m, 2H), 3.17 (s, 3H); isomer B (50%) δ 8.74 (d, 1H), 8.28 (d, 1H), 5.77 (s, 1H), 3.61-3.63 (m, 2H), 3.37-3.39 (m, 2H), 3.16 (s, 3H).

Step 2: Synthesis of 5-bromo-1-(2-methoxy-ethoxymethyl)-3-(2-methoxy-phenyl)-1H-pyrazolo[3,4-b]pyridine A mixture of 5-bromo-3-iodo-1-(2-methoxy-ethoxymethyl)-1H-pyrazolo[3,4-b]pyridine (180 mg, 0.44 mmol), 1,1'-bis(diphenylphosphino)ferrocenepalladium(II)-dichloride dichlormethane adduct (18 mg, 25 µmol) and 2-methoxyphenylboronic acid (82 mg, 0.51 mmol) in acetonitrile (3 mL) and 2 M aqueous solution of sodium carbonate (3 ml) in a sealed vial was stirred at 60° C. for 2 h. The crude mixture was distributed between ethyl acetate and brine. The aqueous phase was extracted with ethyl acetate (3×) and the combined organic phases were dried over sodium sulfate, filtered and concentrated. The crude was then purified by flash silica gel chromatography using a gradient of ethyl acetate in hexanes to afford 5-bromo-1-(2-methoxy-ethoxymethyl)-3-(2-methoxy-phenyl)-1H-pyrazolo[3,4-b]pyridine (80 mg, 0.2 mmol, 46% yield) as a yellow oil. $^1$H-NMR (500 MHz, d$_6$-DMSO) δ 8.70 (d, 1H), 8.40 (d, 1H), 7.62 (dd, 1H), 7.49 (ddd, 1H), 7.22 (d, 1H), 7.09 (dt, 1H), 5.85 (s, 2H), 3.85 (s, 3H), 3.68-3.70 (m, 2H), 3.39-3.41 (m, 2H), 3.18 (s, 3H). MS: m/z 316, 318 [MH$^+$].

Step 3: Synthesis of 3-[3-(2-methoxy-phenyl)-1H-pyrazolo[3,4-b]pyridin-5-yl]-benzoic acid A mixture of 5-bromo-3-iodo-1/2-(2-methoxy-ethoxymethyl)-1H-pyrazolo[3,4-b]pyridine (560 mg, 1.36 mmol, mixture of regioisomers), 2-methoxyphenylboronic acid (217 mg, 1.4 mmol) and 1,1'-bis(diphenylphosphino)ferrocenepalladium(II)-dichloride dichlormethane adduct (50 mg, 68 µmol) in acetonitrile (4 mL) and 2 M aqueous solution of sodium carbonate (2 mL) was stirred in a sealed vial at 70° C. for 105 min. The crude product was then distributed between ethyl acetate and water. The aqueous phase was extracted ethyl acetate (3×) and the combined organic phases were washed with brine, dried over sodium sulfate, filtered and concentrated to afford 5-bromo-1-(2-methoxy-ethoxymethyl)-3-(2-methoxy-phenyl)-1H-pyrazolo[3,4-b]pyridine (780 mg, 75% pure, 1.12 mmol, 82% yield) as a crude dark oil. $^1$H-NMR (500 MHz, d$_6$-DMSO) δ 8.70 (d, 1H), 8.40 (d, 1H), 7.62 (dd, 1H), 7.49 (ddd, 1H), 7.22 (d, 1H), 7.09 (dt, 1H), 5.85 (s, 2H), 3.85 (s, 3H), 3.68-3.70 (m, 2H), 3.39-3.41 (m, 2H), 3.18 (s, 3H). MS: m/z 316, 318 [MH$^+$].

A mixture of the above crude oil (1.12 mmol), 3-carboxyphenylboronic acid (259 mg (1.56 mmol) and 1,1'-bis(diphenylphosphino)ferrocenepalladium(II)-dichloride dichlormethane adduct (54 mg, 75 µmol) in acetonitrile (5 mL) and 2 M aqueous solution of sodium carbonate (5 mL) was irradiated in a Personal Chemistry Optimizer at 165° C. for 20 min. The crude product was diluted with acetonitrile and the organic phase was separated and concentrated. The residue was dissolved in potassium hydroxide in water (10% w/v, 15 mL), washed with ethyl acetate (3×) and filtered through celite. The filtrate was then acidified to pH 3-4 by addition of concentrated aqueous hydrochloric acid and the precipitate was collected. Dichloromethane was then added to the precipitate, the insoluble material filtered off and the filtrate concentrated to afford 3-[1-(2-methoxy-ethoxymethyl)-3-(2-methoxy-phenyl)-1H-pyrazolo[3,4-b]pyridin-5-yl]-benzoic acid (369 mg, 0.85 mmol, 57% yield) as a dark solid. $^1$H-NMR (500 MHz, d$_6$-DMSO) δ 8.95 (d, 1H), 8.42 (d, 1H), 8.26 (t, 1H), 8.02 (dt, 1H), 7.98 (dt, 1H), 7.68 (dd, 1H), 7.64 (t, 1H), 7.51 (ddd, 1H), 7.25 (d, 1H), 7.12 (dt, 1H), 5.91 (s, 2H), 3.87 (s, 3H), 3.73-3.75 (m, 2H), 3.43-3.45 (m, 2H), 3.21 (s, 3H). MS: m/z 432 [M−H$^-$].

The resulting solid was dissolved in dichloromethane and PS-thiophenol (Argonaut Technologies) (1.4 mmol·g$^{-1}$, 1.2 g, 1.7 mmol,) and trifluoroacetic acid (6 ml) were added. The resulting mixture was gently stirred at 50° C. for 8.5 h. The resin was filtered off and washed with dichloromethane and ether. The combined filtrates were concentrated and distributed between a saturated solution of sodium bicarbonate and dichloromethane. The aqueous phase was washed three times with dichloromethane and then acidified to pH 3-4 by addition of concentrated hydrochloric acid. The resulting aqueous phase was extracted three times with ethyl acetate. The combined ethyl acetate phases were washed with brine, dried over sodium sulfate, filtered and concentrated to afford 3-[3-(2- methoxy-phenyl)-1H-pyrazolo[3,4-b]pyridin-5-yl]-benzoic acid (117 mg, 0.34 mmol, 40% yield, 25% over three steps) as a yellow solid. $^1$H-NMR (500 MHz, d$_6$-DMSO) δ 8.87 (d, 1H), 8.37 (d, 1H), 8.24 (t, 1H), 8.02 (dt, 1H), 7.98 (dt, 1H), 7.68 (dd, 1H), 7.64 (t, 1H), 7.47 (ddd, 1H), 7.23 (d, 1H), 7.11 (dt, 1H), 3.86 (s, 3H). MS: m/z 346 [MH$^+$].

Step 4: Synthesis of {3-[3-(2-methoxy-phenyl)-1H-pyrazolo[3,4-b]pyridin-5-yl]-phenyl}-(4-methyl-piperazin-1-yl)-methanone To a solution of 3-[3-(2-methoxy-phenyl)-1H-pyrazolo[3,4-b]pyridin-5-yl]-benzoic acid (25 mg, 72 μmol) in anhydrous DMF (1.5 mL) was added PS-DCC resin (Argonaut Technologies) (180 mg, 0.22 mmol, 1.21 mmol·g$^{-1}$) and N-methylpiperazine (9.6 μl, 86 μmol). The resulting mixture was stirred at 60° C. for 16 h. The resin was filtered off, washing with dichloromethane and ether and the filtrate concentrated. The residue was dissolved in dichloromethane and treated with a PS-trisamine resin (Argonaut Technologies) (20 mg). The resin was again removed by filtration and washed with dichloromethane and ether. The filtrate was concentrated and the resulting crude product was purified by reverse phase mass-triggered HPLC using a gradient of acetonitrile in water containing 0.1% of formic acid to afford {3-[3-(2-methoxy-phenyl)-1H-pyrazolo[3,4-b]pyridin-5-yl]-phenyl}-(4-methyl-piperazin-1-yl)-methanone (1.7 mg, 4.0 μmol, 6% yield). $^1$H-NMR (500 MHz, d$_6$-DMSO) δ 8.87 (d, 1H), 8.37 (d, 1H), 8.24 (t, 1H), 8.02 (dt, 1H), 7.98 (dt, 1H), 7.68 (dd, 1H), 7.64 (t, 1H), 7.47 (ddd, 1H), 7.23 (d, 1H), 7.11 (dt, 1H), 3.86 (s, 3H). MS: m/z 346 [MH$^+$].

Other Compounds Prepared by Method 9:

TABLE 7

| Structure |
|---|
| 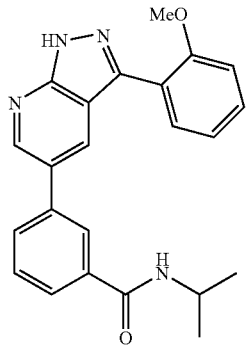<br>MS: m/z 387 [MH$^+$] |

Method 10:

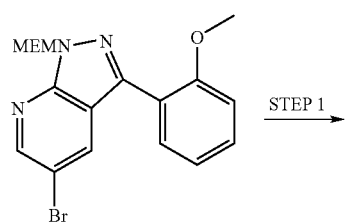

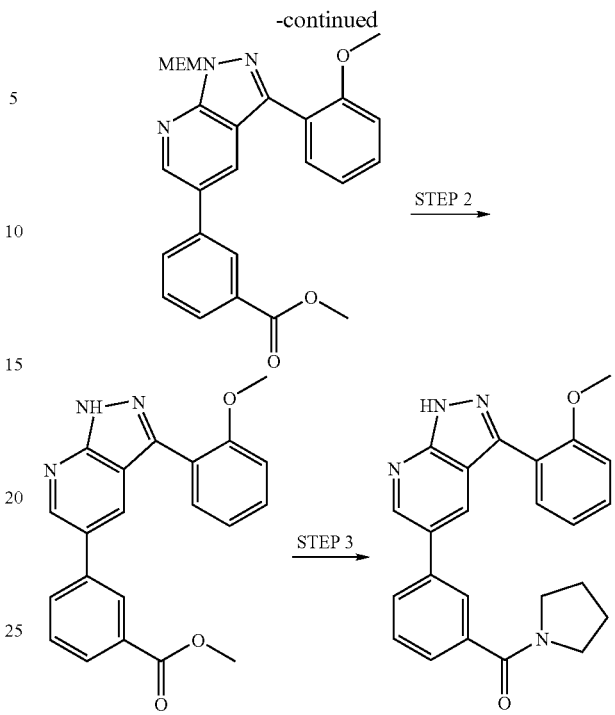

Step 1: Synthesis of 3-[1-(2-methoxy-ethoxymethyl)-3-(2-methoxy-phenyl)-1H-pyrazolo[3,4-b]pyridin-5-yl]-benzoic acid methyl ester A mixture of 5-bromo-1-(2-methoxy-ethoxymethyl)-3-(2-methoxy-phenyl)-1H-pyrazolo[3,4-b]pyridine (535 mg, 1.36 mmol), 3-methoxycarbonylphenylboronic acid (258 mg, 1.43 mmol) and 1,1'-bis(diphenylphosphino)ferrocenepalladium(II)-dichloride dichlormethane adduct (50 mg, 68 μmol) in acetonitrile (7 mL) and 2 M aqueous solution of sodium carbonate (7 mL) was irradiated in a Personal Chemistry Optimizer at 90° C. for 10 minutes. The resulting mixture was distributed between ethyl acetate and water. The aqueous phase was extracted twice with ethyl acetate and the combined organic phases were washed with brine, dried over sodium sulfate, filtered and concentrated. The crude was purified by flash silica gel chromatography using a gradient of ethyl acetate and hexanes to afford 3-[1-(2-methoxy-ethoxymethyl)-3-(2-methoxy-phenyl)-1H-pyrazolo[3,4-b]pyridin-5-yl]-benzoic acid methyl ester (612 mg, 1.36 mmol, 100% yield) as a yellow oil. $^1$H-NMR (500 MHz, d$_6$-DMSO) δ 8.96 (d, 1H), 8.43 (d, 1H), 8.28 (t, 1H), 8.07 (td, 1H), 7.99 (td, 1H), 7.67-7.69 (m, 2H), 7.51 (ddd, 1H), 7.25 (d, 1H), 7.12 (dt, 1H), 5.92 (s, 2H), 3.90 (s, 3H), 3.87 (s, 3H), 3.73-3.75 (m, 2H), 3.43-3.45 (m, 2H), 3.21 (s, 3H). MS: m/z 372 [MH$^+$].

Step 2: Synthesis of 3-[3-(2-methoxy-phenyl)-1H-pyrazolo[3,4-b]pyridin-5-yl]-benzoic acid methyl ester A solution of 3-[1-(2-methoxy-ethoxymethyl)-3-(2-methoxy-phenyl)-1H-pyrazolo[3,4-b]pyridin-5-yl]-benzoic acid methyl ester (573 mg, 1.28 mmol) in dichloromethane (25 mL) was cooled down to 0-5° C. and boron trifluoride etherate (0.8 ml, 6.4 mmol) was added. The mixture was slowly warmed to room temperature and stirred for 16 h. A yellow precipitate was formed was filtered off to afford 3-[3-(2-methoxy-phenyl)-1H-pyrazolo[3,4-b]pyridin-5-yl]-benzoic acid methyl ester (110 mg (0.29 mmol; 23% yield). $^1$H-NMR (500 MHz, $d_6$-DMSO) δ 8.88 (d, 1H), 8.39 (d, 1H), 8.27 (t, 1H), 8.06 (td, 1H), 7.99 (td, 1H), 7.65-7.68 (m, 2H), 7.48 (ddd, 1H), 7.23 (d, 1H), 7.11 (dt, 1H), 3.90 (s, 3H), 3.87 (s, 3H). MS: m/z 360 [MH$^+$].

Step 3: Synthesis of {3-[3-(2-methoxy-phenyl)-1H-pyrazolo[3,4-b]pyridin-5-yl]-phenyl}-pyrrolidin-1-yl-methanone 3-[3-(2-methoxy-phenyl)-1H-pyrazolo[3,4-b]pyridin-5-yl]-benzoic acid methyl ester (30 mg, 83 μmol) was dissolved in pyrrolidine (0.35 ml, 4.15 mmol) and the mixture was stirred at 90° C. for 16 h. The mixture was then concentrated and the crude product purified by flash silica gel chromatography using a gradient of 10% v/v of methanol in ethyl acetate to afford {3-[3-(2-methoxy-phenyl)-1H-pyrazolo[3,4-b]pyridin-5-yl]-phenyl}-pyrrolidin-1-yl-methanone as a yellow solid (22 mg, 55 μmol, 67% yield). $^1$H-NMR (500 MHz, $d_6$-MeOH) δ 8.82 (d, 1H), 8.39 (d, 1H), 7.83 (t, 1H), 7.79 (td, 1H), 7.66 (dd, 1H), 7.55-7.59 (m, 2H), 7.48 (ddd, 1H), 7.20 (d, 1H), 7.11 (dt, 1H), 3.88 (s, 3H), 3.63 (t, 2H), 3.52 (t, 2H), 2.02 (m, 2H), 1.92 (m, 2H). MS: m/z 399 [MH$^+$].

Method 11:

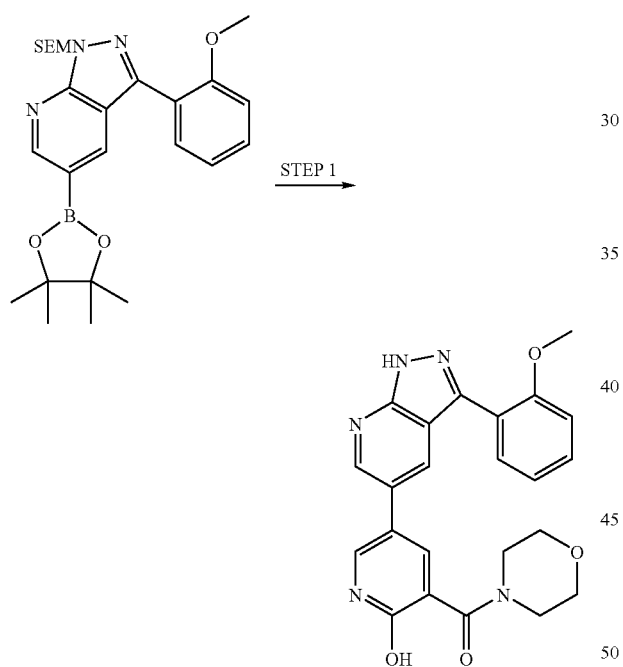

dichloromethane and a saturated aqueous solution of sodium bicarbonate. The phases were separated and the aqueous phase was extracted twice with dichloromethane. The organic phases were combined, dried over sodium sulfate, filtered and concentrated. The crude product was then purified by flash silica gel chromatography using a gradient of ethyl acetate containing 15% v/v of methanol and hexanes to afford 137 mg of a beige oil.

The oil was dissolved in 24 mL of a 1:1 mixture of dimethoxyethane and concentrated aqueous hydrochloric acid. The mixture was heated to 55° C. for 1 h and then neutralized by addition of sodium bicarbonate. The resulting mixture was distributed between ethyl acetate and water and the aqueous phase was extracted three times with ethyl acetate. The combined organic phases were washed with brine, dried over sodium sulfate and evaporated. The crude material was purified by reverse phase mass-triggered HPLC using a gradient of acetonitrile in water containing 0.1% of formic acid to afford 12.3 mg (28 μmol, 11% yield) of {2-hydroxy-5-[3-(2-methoxy-phenyl)-1H-pyrazolo[3,4-b]pyridin-5-yl]-pyridin-3-yl}-morpholin-4-yl-methanone as an off-white solid upon lyophilization. $^1$H-NMR (500 MHz, $d_6$-DMSO) δ 13.79 (s, 1H), 12.25 (s, 1H), 8.77 (d, 1H), 8.26 (d, 1H), 8.00 (d, 1H), 7.94 (d, 1H), 7.62 (dd, 1H), 7.46 (ddd, 1H), 7.22 (d, 1H), 7.09 (ddd, 1H), 3.83 (s, 3H), 3.7-3.2 (m, 8H). MS: m/z 432 [MH$^+$].

Method 12:

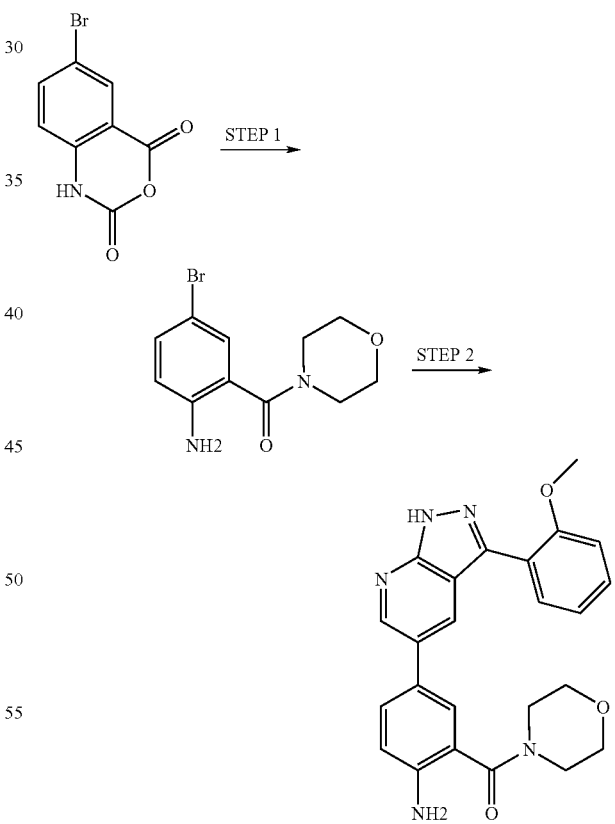

Step 1: Synthesis of {2-hydroxy-5-[3-(2-methoxy-phenyl)-1H-pyrazolo[3,4-b]pyridin-5-yl]-pyridin-3-yl}-morpholin-4-yl-methanone 122 mg (0.25 mmol) of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine, 150 mg (0.52 mmol) of (5-bromo-2-fluoro-pyridin-3-yl)-morpholin-4-yl-methanone, and 15 mg (18 μmol) of 1,1'-bis(diphenylphosphino)ferrocenepalladium(II)-dichloride dichlormethane adduct were placed in a Smith vial. 2 mL of acetonitrile, 1 ml of water and 1 ml of a saturated aqueous solution of sodium bicarbonate were added and the resulting mixture irradiated in a Personal Chemistry Optimizer at 100° C. for 30 min. The resulting residue was distributed between Step 1: Synthesis of (2-Amino-5-bromo-phenyl)-morpholin-4-yl-methanone Into an 8 mL screw cap vial were added 5-bromoisatoic anhydride (0.200 g, 0.826 mmol), anhydrous THF (5 mL), and morpholine (101 mg, 1.16 mmol). The vial was sealed and placed in a heat block at 60° C. for 1.5 h after which it was concentrated under vacuum. The crude product was triturated with Et₂O/hexanes to afford 111 mg (94%) of (2-Amino-5-bromo-phenyl)-morpholin-4-yl-methanone as a tan solid. m/z 285/287 [MH⁺].

Step 2: Synthesis of {2-Amino-5-[3-(2-methoxy-phenyl)-1H-pyrazolo[3,4-b]pyridin-5-yl]-phenyl}-morpholin-4-yl-methanone Into a 5 mL Personal Chemistry microwave reaction vial were added 3-(2-methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (0.0498 g, 0.103 mmol), (2-Amino-5-bromo-phenyl)-morpholin-4-yl-methanone (0.0378 g, 0.132 mmol), 1,1'-bis(diphenylphosphino)ferrocenepalladium(II)-dichloride dichloromethane adduct (13.4 mg, 0.017 mmol), acetonitrile (1 mL) and saturated aqueous NaHCO₃ (1 mL). The vial was sealed, purged with N₂, and irradiated in a Personal Chemistry Optimizer at 90° C. for 5 min. The layers were separated, and the aqueous phase was extracted 3× with EtOAc. The combined organic phase was treated with brine, dried (Na₂SO₄), filtered and concentrated. The crude product was dissolved in 5 mL of a solution consisting of 1 part HClO₄ (70%, ACS) and 20 parts glacial acetic acid, and the solution was stirred at rt for 8 h. The reaction mixture was concentrated under vacuum, and neutralized to pH 7 with saturated NaHCO₃ followed by solid NaHCO₃. The quenched reaction mixture was partitioned between EtOAc and water, the layers were separated, and the aqueous phase was extracted 2× with EtOAc. The combined organic phase was treated with brine, dried (Na₂SO₄), filtered and concentrated. Purification by mass-triggered LC (positive mode, ESI) through a C-18 reverse-phase column (Thomson Instrument Co. ODS-A 100A, 5μ, 50×21.3 mm, eluting at 20 mL/min with acetonitrile (containing 0.1% formic acid) and water (containing 0.1% formic acid) in a 5-95% gradient afforded the title compound, which upon lysophilization appeared as a brown viscous oil (12.9 mg, 29%). ¹H-NMR (500 MHz, d₆-DMSO) δ 13.71 (br. s, 1H), 8.74 (d, J=2.0 Hz, 1H), 8.16 (d, J=2.0 Hz, 1H), 7.62 (d, J=7.5 Hz, 1H), 7.49 (dd, J=2.5, 8.0 Hz, 1H), 7.45 (m, 1H), 7.37 (d, J=2.0 Hz, 1H), 7.20 (d, J=8.0 Hz, 1H), 7.08 (t, J=8.5 Hz, 1H), 6.81 (d, J=8.0 Hz, 1H), 5.37 (s, 2H), 3.83 (s, 3H), 3.60 (m, 4H), 3.49 (m, 4H); MS: m/z 430.1 [MH⁺].

Other Examples Prepared by Method 12:

TABLE 8

| Structure |
| --- |
| 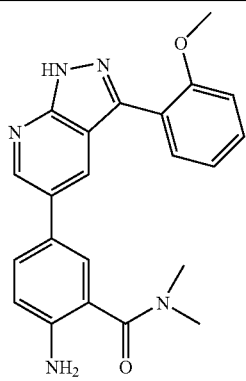<br>MS: m/z 388 [MH⁺] |

TABLE 8-continued

| Structure |
| --- |
| 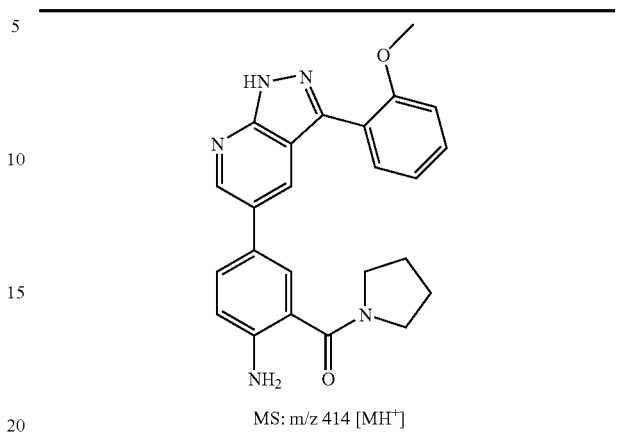<br>MS: m/z 414 [MH⁺] |

Method 13:

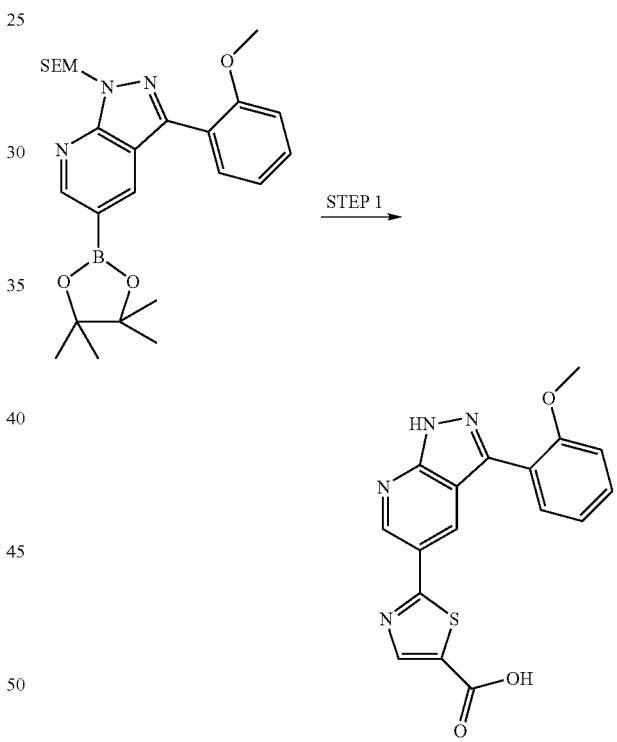

STEP 1

Step 1: Synthesis of 2-[3-(2-Methoxy-phenyl)-1H-pyrazolo[3,4-b]pyridin-5-yl]-thiazole-5-carboxylic acid Into a 20 mL Personal Chemistry microwave reaction vial were added 3-(2-Methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (0.4992 g, 1.038 mmol), 2-Bromo-thiazole-5-carboxylic acid methyl ester (0.2592 g, 1.167 mmol), 1,1'-bis(diphenylphosphino)ferrocenepalladium(II)-dichloride dichloromethane adduct (95.4 mg, 0.117 mmol), acetonitrile (5 mL) and 2M aqueous Na₂CO₃ (5 mL). The vial was sealed, purged with N₂, and irradiated in a Personal Chemistry Optimizer at 130° C. for 30 min. The reaction mixture was diluted with EtOAc and acidified with acetic acid to pH 5. The layers were separated, and the aqueous phase was extracted 5× with EtOAc. The combined organic phase was treated with brine, dried (Na$_2$SO$_4$), filtered and concentrated. The crude product was dissolved in 10 mL of a solution consisting of 1 part HClO$_4$ (70%, ACS) and 20 parts glacial acetic acid, and the solution was stirred at rt for 4 h. The reaction mixture was concentrated under vacuum, and neutralized to pH 7 with saturated NaHCO$_3$ followed by solid NaHCO$_3$. The quenched reaction mixture was partitioned between EtOAc and water, the layers were separated, and the aqueous phase was extracted 2× with EtOAc. The aqueous phase was then acidified to pH 4 with acetic acid and extracted 5× with EtOAc. The combined organic extracts was treated with brine, dried (Na$_2$SO$_4$), filtered and concentrated. Trituration with Et$_2$O afforded the title compound as a greenish-brown powder (0.296 g, 81% yield). $^1$H-NMR (500 MHz, d$_6$-DMSO) δ 13.73 (br. s, 1H), 9.16 (s, 1H), 8.71 (s, 1H), 8.40 (s, 1H), 7.68 (d, J=8.0 Hz, 1H), 7.48 (t, J=8.0 Hz, 2H), 7.24 (d, J=8.0 Hz, 1H), 7.10 (t, J=7.5 Hz 1H), 3.87 (s, 3H); MS: m/z 353.1 [MH$^+$].

Other examples prepared by Method 13:

TABLE 9

| Structure |
|---|
| 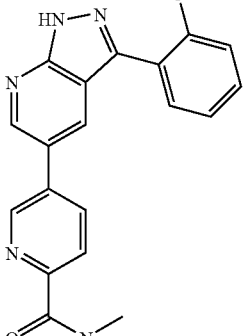<br>MS: m/z 374 [MH$^+$] |
| 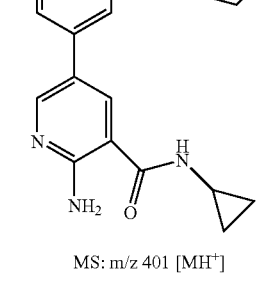<br>MS: m/z 362.1 [MH$^+$]. |

TABLE 9-continued

| Structure |
|---|
| 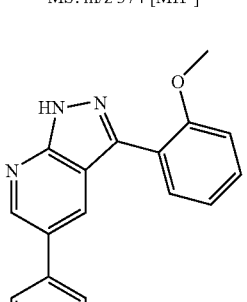<br>MS: m/z 392 [MH$^+$] |
| 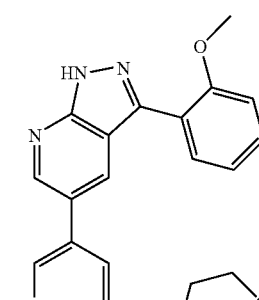<br>MS: m/z 401 [MH$^+$] |
| 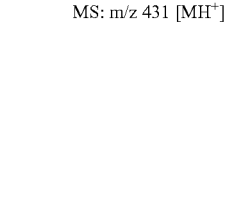<br>MS: m/z 431 [MH$^+$] |

TABLE 9-continued
| Structure |
|---|
| 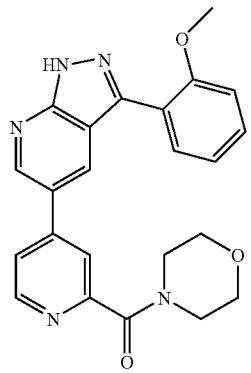 MS: m/z 416 [MH+] |
| 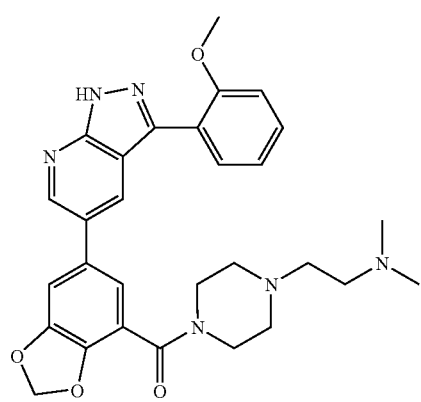 MS: m/z 529.2 (M + H+) |
| 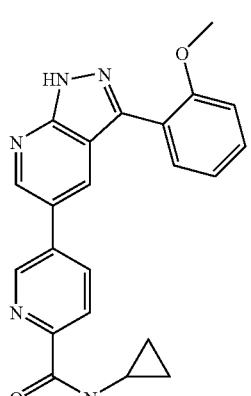 MS: m/z 386 [MH+] |
TABLE 9-continued
| Structure |
|---|
| 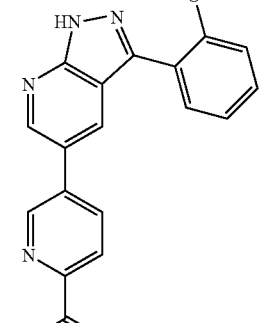 MS: m/z 347.1 (M + H+). |
| 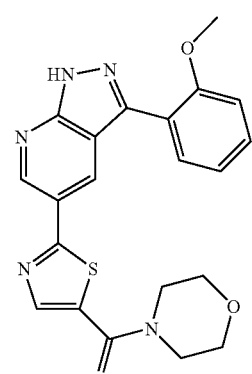 MS: m/z 422 [MH+] |
| 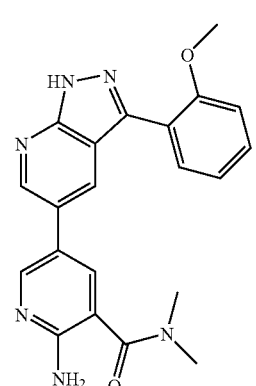 MS: m/z 389 [MH+] |

TABLE 9-continued
Structure
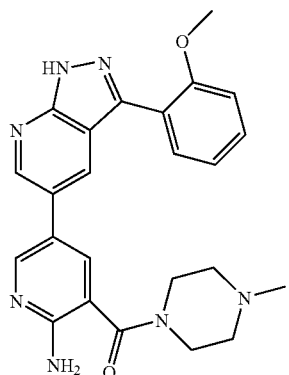
MS: m/z 444 [MH+]
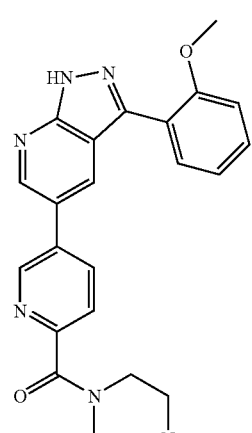
MS: m/z 429 [MH+]
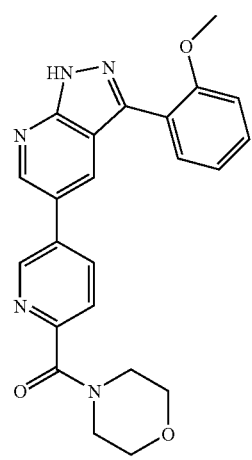
MS: m/z 416 [MH+]
TABLE 9-continued
Structure
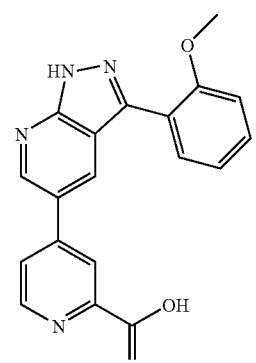
MS: m/z 347 [MH+]
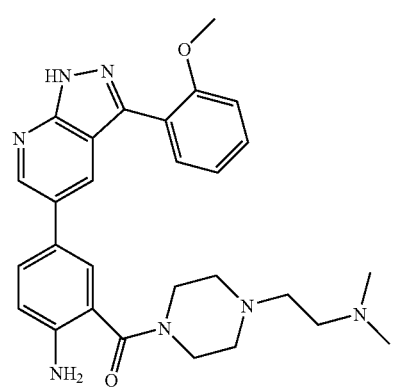
MS: m/z 501 [MH+]
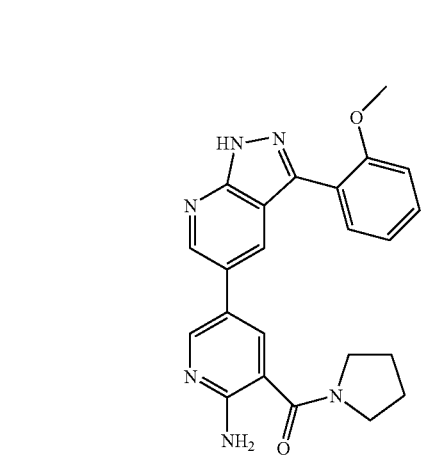
MS: m/z 415 [MH+]

TABLE 9-continued

| Structure |
|---|
| 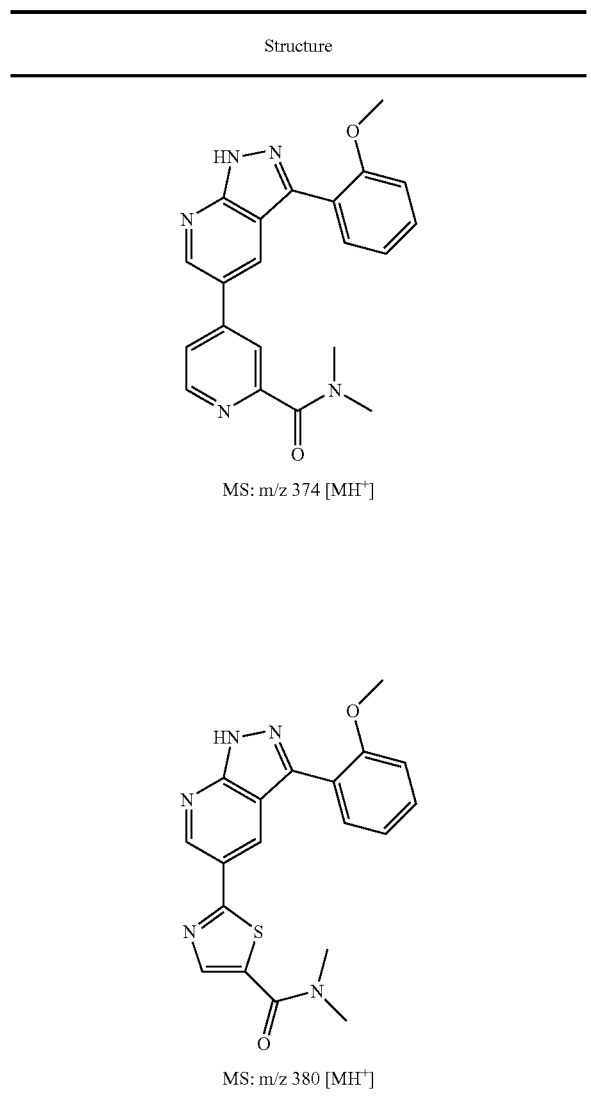
MS: m/z 374 [MH+]

MS: m/z 380 [MH+] |

Method 14:

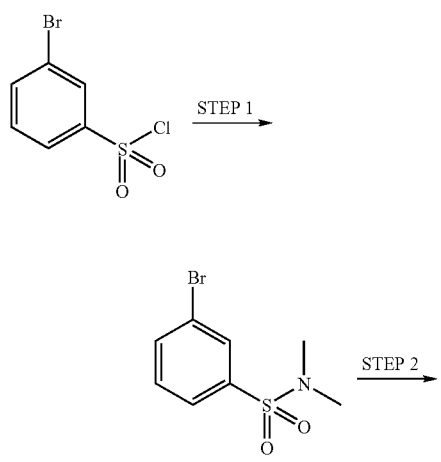

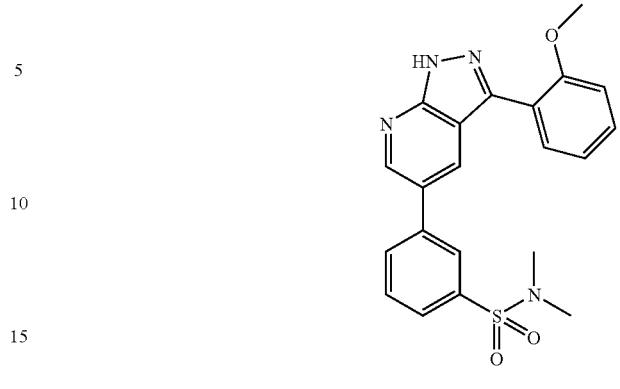

Step 1: Synthesis of 3-Bromo-N,N-dimethyl-benzenesulfonamide

Into a 20 mL scintillation vial were added 3-Bromobenzenesulfonyl chloride (0.301 g, 1.179 mmol) and anhydrous pyridine (5 mL). A 2M solution of dimethylamine in THF (1.0 mL, 2.0 mmol) was added dropwise, and the reaction mixture was stirred at rt under $N_2$ for 5 h after which it was concentrated under vacuum. The crude residue was partitioned between EtOAc and 1M citric acid. The layers were separated, and the organic phase was washed 3× with 1M citric acid, then treated with brine, dried ($Na_2SO_4$), filtered and concentrated. Trituration with $Et_2O$ provided 3-Bromo-N,N-dimethyl-benzenesulfonamide as a white powder (0.297 g, 96%). MS: m/z 263.9/265.9 [MH+].

Step 2: Synthesis of 3-[3-(2-Methoxy-phenyl)-1H-pyrazolo[3,4-b]pyridin-5-yl]-N,N-dimethyl-benzenesulfonamide Into a 5 mL Personal Chemistry microwave reaction vial were added 3-(2-Methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (0.0496 g, 0.103 mmol), 3-Bromo-N,N-dimethyl-benzenesulfonamide (0.0417 g, 0.143 mmol), 1,1'-bis(diphenylphosphino)ferrocenepalladium(II)-dichloride dichloromethane adduct (13.9 mg, 0.017 mmol), acetonitrile (1 mL) and saturated aqueous $NaHCO_3$ (1 mL). The vial was sealed, purged with $N_2$, and irradiated in a Personal Chemistry Optimizer at 90° C. for 15 min. The layers were separated, and the aqueous phase was extracted 3× with EtOAc. The combined organic phase was treated with brine, dried ($Na_2SO_4$), filtered and concentrated. The crude product was dissolved in 5 mL of a solution consisting of 1 part $HClO_4$ (70%, ACS) and 20 parts glacial acetic acid, and the solution was stirred at rt for 1 h. The reaction mixture was concentrated under vacuum, and neutralized to pH 7 with saturated $NaHCO_3$ followed by solid $NaHCO_3$. The quenched reaction mixture was partitioned between EtOAc and water, the layers were separated, and the aqueous phase was extracted 2× with EtOAc. The combined organic phase was treated with brine, dried ($Na_2SO_4$), filtered and concentrated. Purification by mass-triggered LC (positive mode, ESI) through a C-18 reverse-phase column (Thomson Instrument Co. ODS-A 10A, 5μ, 50×21.3 mm, eluting at 20 mL/min with acetonitrile (containing 0.1% formic acid) and water (containing 0.1% formic acid) in a 5-95% gradient afforded the title compound, which upon lysophilization appeared as a light yellow powder (10.4 mg, 25%). $^1$H-NMR (500 MHz, d$_6$-DMSO) δ=13.91 (br. s, 1H), 8.92 (d, J=2.0 Hz, 1H), 8.44 (d, J=2.0 Hz, 1H), 8.12 (m, 1H), 8.01 (br.s, 1H), 7.76 (m, 2H), 7.67 (dd, J=2.0, 7.5 Hz, 1H), 7.45 (m, 1H), 7.22 (d, J=8.0 Hz, 1H), 7.09 (t, J=8.0 Hz, 1H), 3.85 (s, 3H), 2.66 (s, 6H); MS: m/z 409.1 [MH$^+$].
Other compounds prepared by Method 14:
TABLE 10
| Structure |
| --- |
| 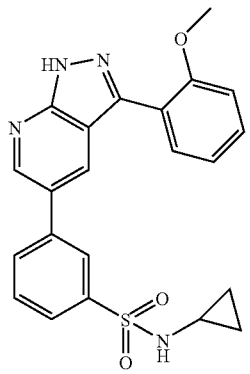<br>MS: m/z 421 [MH$^+$] |
| 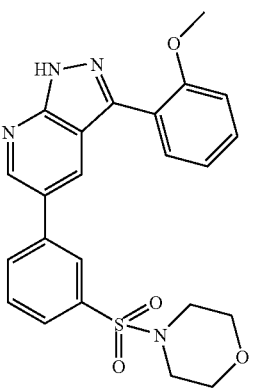<br>MS: m/z 451 [MH$^+$] |
| 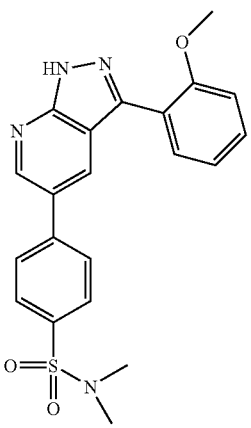<br>MS: m/z 409 [MH$^+$] |
TABLE 10-continued
| Structure |
| --- |
| 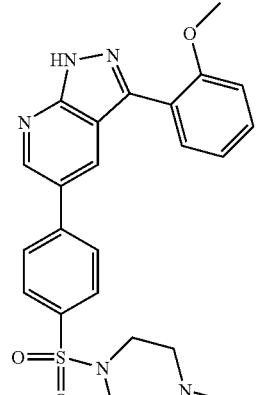<br>MS: m/z 464 [MH$^+$] |
| 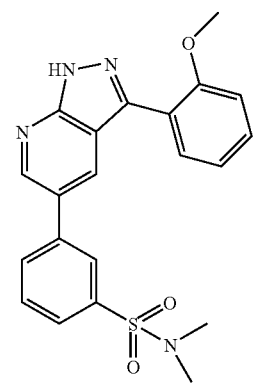<br>MS: m/z 409 [MH$^+$] |
| 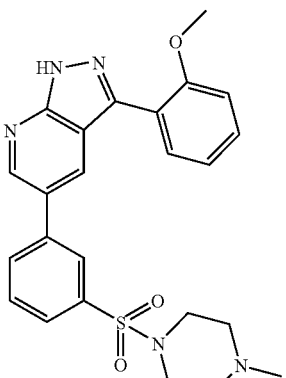<br>MS: m/z 464 [MH$^+$] |

TABLE 10-continued
Structure
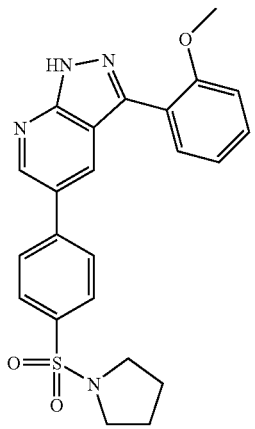
MS: m/z 435 [MH+]
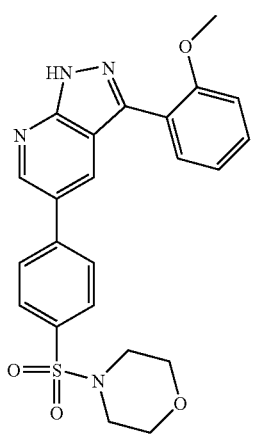
MS: m/z 451 [MH+]
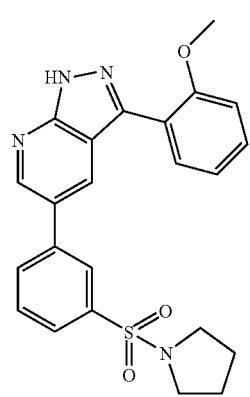
MS: m/z 435 [MH+]
TABLE 10-continued
Structure
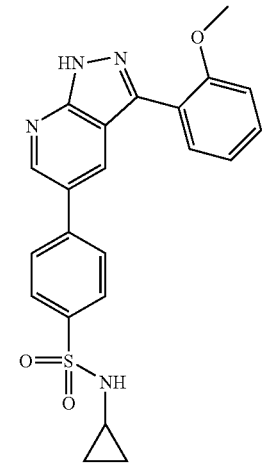
MS: m/z 421 [MH+]
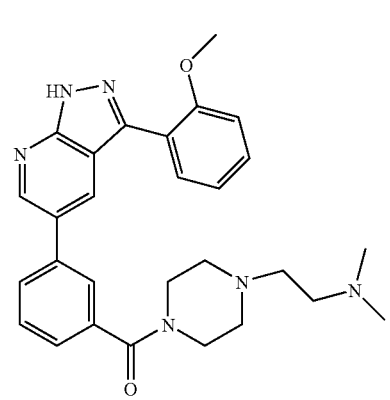
MS: m/z 485 [MH+]
Method 15:
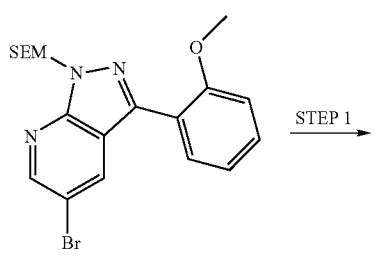
STEP 1

-continued

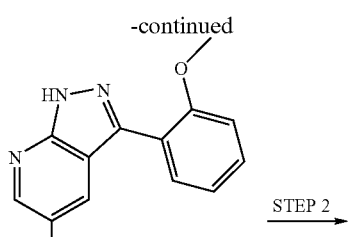

STEP 2 →

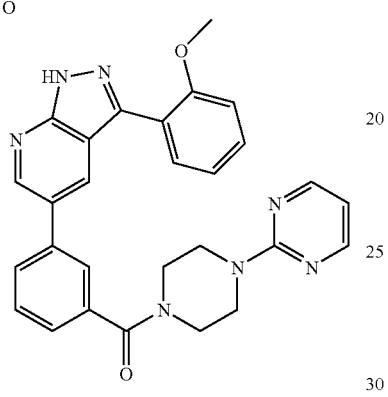

Step 1: Synthesis of 3-[3-(2-Methoxy-phenyl)-1H-pyrazolo[3,4-b]pyridin-5-yl]-benzoic acid To a solution of 5-bromo-3-(2-methoxy-phenyl)-1-(2-trimethylsilanyl-ethoxymethyl)-1H-pyrazolo[3,4-b]pyridine (997 mg, 2.30 mmol) in acetonitrile (15 mL) and saturated aqueous NaHCO$_3$ (10 mL) in a microwave vial was added 3-carboxyphenylboronic acid, pinacol ester (625 mg, 2.52 mmol) and [1,1'-bis(diphenylphosphino)ferrocene]dichloropalladium (II), complex with dichloromethane (1:1) (94 mg, 0.12 mmol). The vial was capped, flushed with N$_2$, evacuated under vacuum, and heated in a microwave at 90° C. for 1500 seconds. The acetonitrile was removed via rotary evaporation. Ethyl acetate was added and then separated from the aqueous layer. The organic layer was dark brown and LC/MS showed that the product remained in this layer. Concentrated down to a dark brown oil and redissolved in a 5% perchloric acid in acetic acid solution (10 mL). The reaction solution was stirred 4.5 hours at ambient temperature. The perchloric acid was removed via rotary evaporation and then ethyl acetate and H$_2$O were added. Sodium bicarbonate powder was added until pH=3. The organic layer was separated, dried over Na$_2$SO$_4$, and concentrated under vacuum to afford a brown powder (580 mg, 62% yield). $^1$H NMR (500 MHz, d$_6$-DMSO) δ 13.81 (br s, 1H), 8.81 (d, J=2.5 Hz, 1H), 8.31 (d, J=2.5 Hz, 1H), 8.18 (s, 1H), 7.95 (d, J=7.5 Hz, 1H), 7.90 (d, J=7.5 Hz, 1H), 7.59 (m, 2H), 7.41 (t, J=7.0 Hz, 1H), 7.17 (d, J=8.0 Hz, 1H), 7.04 (t, J=7.5 Hz, 1H), 3.80 (s, 3H). MS: m/e 346.1 (M+H$^+$).

Step 2: Synthesis of {3-[3-(2-Methoxy-phenyl)-1H-pyrazolo[3,4-b]pyridin-5-yl]-phenyl}-(4-pyrimidin-2-yl-piperazin-1-yl)-methanone To a solution of 3-[3-(2-methoxy-phenyl)-1H-pyrazolo[3,4-b]pyridin-5-yl]-benzoic acid (18 mg, 0.05 mmol) in DMF (1 mL) was added HATU (20 mg, 0.05 mmol) and 1-(2-pyrimidyl)piperazine (11 uL, 0.08 mmol). The reaction solution was stirred for 16 hours at ambient temperature. The crude product was extracted into ethyl acetate and washed with H$_2$O. The organic layer was dried over Na$_2$SO$_4$, filtered, and adsorbed onto silica gel. Purification by flash chromatography with a gradient of ethyl acetate (containing 10% MeOH) and hexanes afforded the title compound as a white powder (7.2 mg, 28% yield). $^1$H NMR (500 MHz, CD$_3$OD) δ 8.85 (d, J=2 Hz, 1H), 8.42 (d, J=2 Hz, 1H), 8.35 (d, J=4.5 Hz, 2H), 7.83 (d, J=8 Hz, 1H), 7.79 (s, 1H), 7.64 (m, 2H), 7.50 (m, 2H), 7.20 (d, J=8.5 Hz, 1H), 7.11 (t, J=8 Hz, 1H), 6.64 (t, J=4.5 Hz, 1H), 3.96 (br s, 2H), 3.89 (s, 3H), 3.86 (br s, 4H), 3.60 (br s, 2H). MS: m/z 492.1 (M+H$^+$).

Other compounds made by Method 15:

TABLE 11

Structure

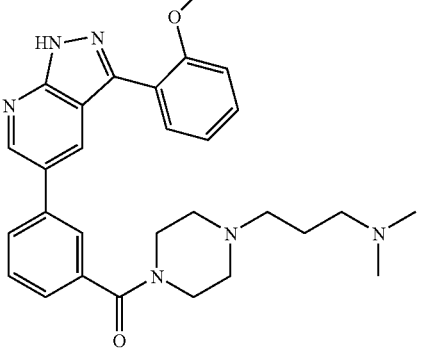

MS: m/z 499 [MH$^+$].

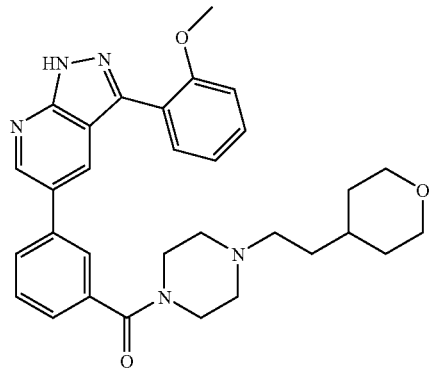

MS: m/z 527 [MH$^+$].

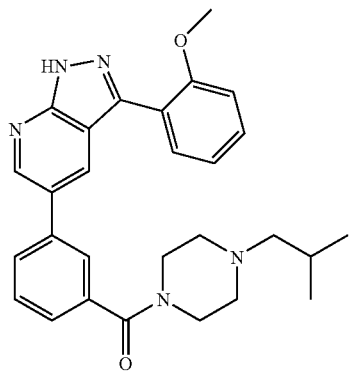

MS: m/z 470 [MH$^+$].

TABLE 11-continued
| Structure |
|---|
| 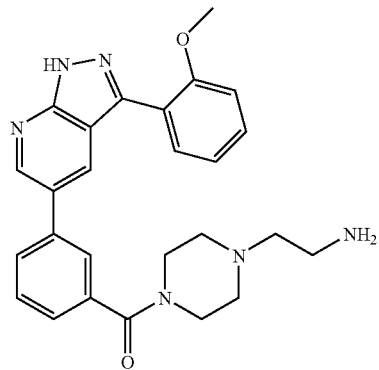<br>MS: m/z 457 [MH+]. |
| 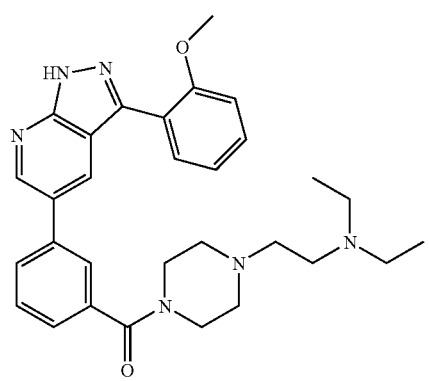<br>MS: m/z 513 [MH+]. |
| 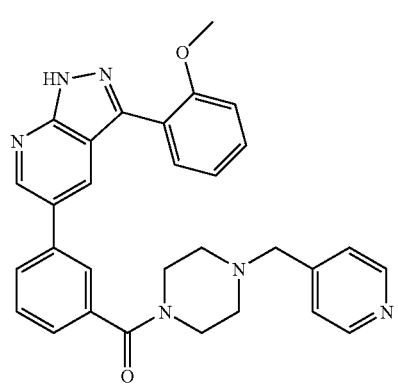<br>MS: m/z 505 [MH+]. |
TABLE 11-continued
| Structure |
|---|
| 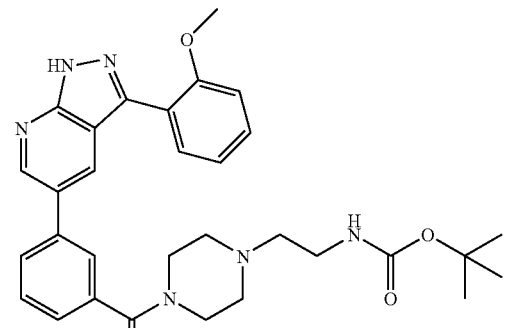<br>MS: m/z 457 [MH+ - 100], 557 [MH+]. |
| 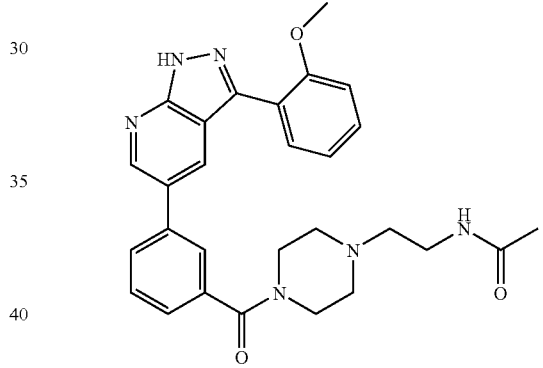<br>MS: m/z 499 [MH+]. |
| 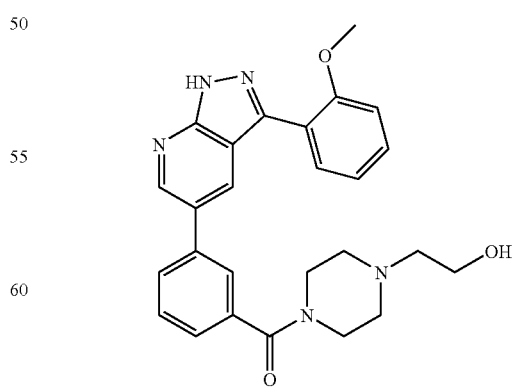<br>MS: m/z 458 [MH+]. |

TABLE 11-continued

| Structure |
|---|
| 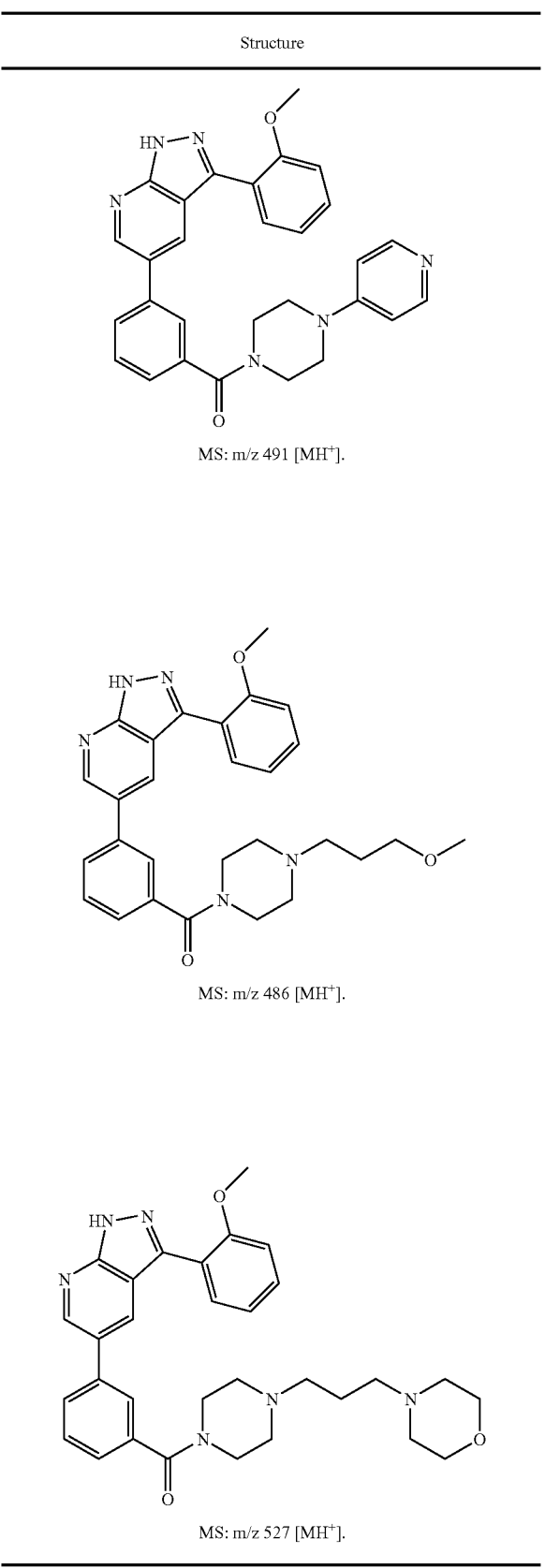<br>MS: m/z 491 [MH+].<br><br>MS: m/z 486 [MH+].<br><br>MS: m/z 527 [MH+]. |

Method 16:

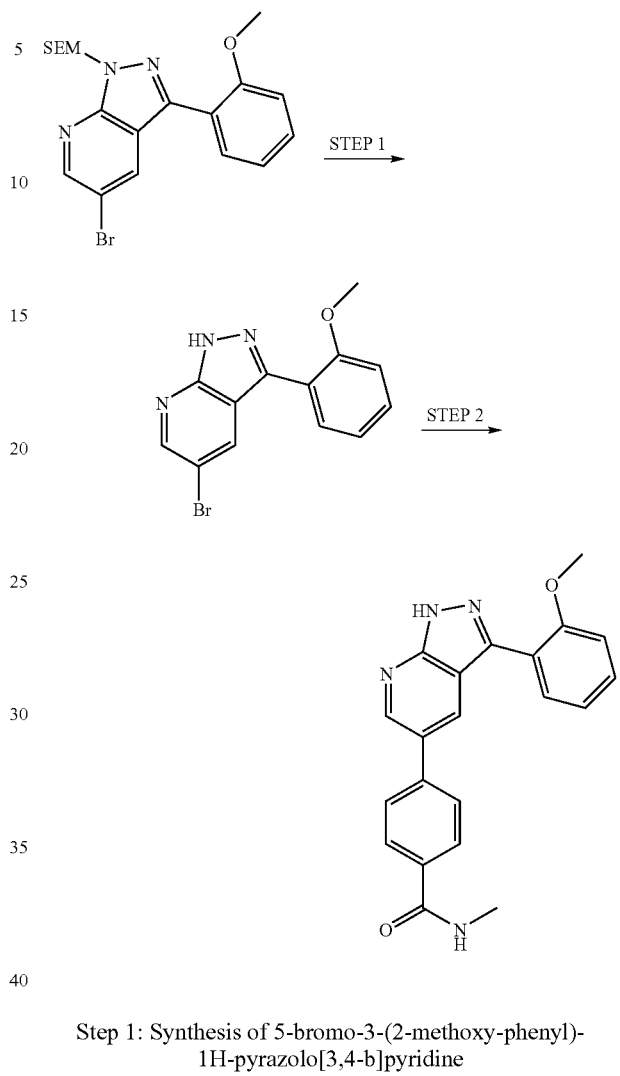

Step 1: Synthesis of 5-bromo-3-(2-methoxy-phenyl)-1H-pyrazolo[3,4-b]pyridine To a solution of 5-bromo-3-(2-methoxy-phenyl)-1-(2-trimethylsilanyl-ethoxymethyl)-1H-pyrazolo[3,4-b]pyridine (260 mg, 0.60 mmol) in THF (3 mL) was added tetrabutylammonium fluoride (6 mL of 1 M in THF solution, 6.00 mmol) and molecular sieves. The solution was heated under reflux (70° C.) for 4 hours without stirring. The solution was cooled to ambient temperature and acidified to pH=5 by adding dropwise a dilute solution of acetic acid in MeOH. The solution was filtered and the filtrate was concentrated via rotary evaporation. The material was extracted into EtOAc and washed 3×H$_2$O. The organic layer was dried over Na$_2$SO$_4$ and concentrated down to afford 5-bromo-3-(2-methoxy-phenyl)-1H-pyrazolo[3,4-b]pyridine as an orange solid (177 mg, 97% yield). MS: m/z 303.9, 305.9 [M+H+]. The material was used directly in step 2 without further purification.

Step 2: Synthesis of 4-[3-(2-Methoxy-phenyl)-1H-pyrazolo[3,4-b]pyridin-5-yl]-N-methyl-benzamide To a solution of 5-bromo-3-(2-methoxy-phenyl)-1H-pyrazolo[3,4-b]pyridine (26 mg, 0.085 mmol) in acetonitrile (1 mL) and saturated aqueous NaHCO$_3$ (1 mL) in a microwave vial was added 4-(N-methylaminocarbonyl)phenylboronic acid (17 mg, 0.094 mmol) and [1,1'-bis(diphenylphosphino)ferrocene]dichloropalladium (II), complex with dichloromethane (1:1) (3.5 mg, 0.004 mmol). The vial was capped, flushed with $N_2$, evacuated under vacuum, and heated in a microwave at 130° C. for 1800 seconds. The material was extracted into EtOAc and the organic layer was dried over $Na_2SO_4$. The material was adsorbed onto $SiO_2$ and purified by flash chromatography in a EtOAc (containing 10% MeOH) and hexane gradient. The clean fractions were concentrated via rotary evaporation to afford the title compound as a white powder (5.9 mg, 20% yield). $^1$H NMR (500 MHz, $CD_3OD$) δ 8.85 (s, 1H), 8.41 (s, 1H), 7.94 (d, J=8.5 Hz, 2H), 7.78 (d, J=8.5 Hz, 2H), 7.67 (d, J=7.5 Hz, 1H), 7.48 (t, 7.0 Hz, 1H), 7.21 (d, J=8.5 Hz, 1H), 7.11 (t, J=7.0 Hz, 1H), 3.89 (s, 3H), 2.95 (s, 3H). MS: m/z 359.1 [M+H$^+$].

Other compounds prepared by Method 16:

TABLE 12

Structure

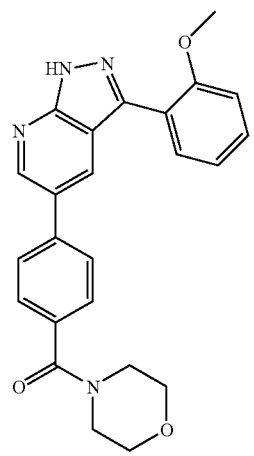

MS: m/z 415 [MH$^+$].

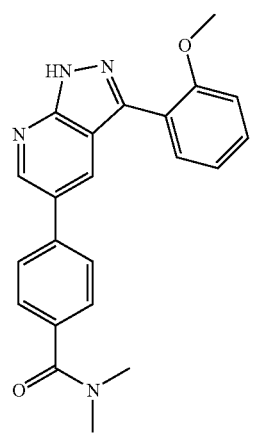

MS: m/z 373 [MH$^+$].

TABLE 12-continued

Structure

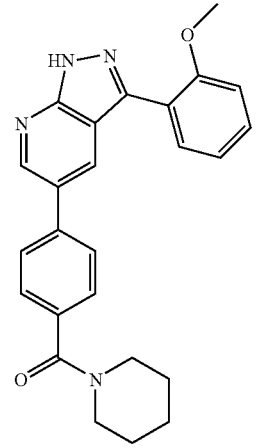

MS: m/z 413 [MH$^+$].

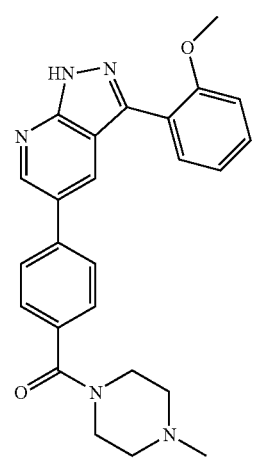

MS: m/z 428 [MH$^+$].

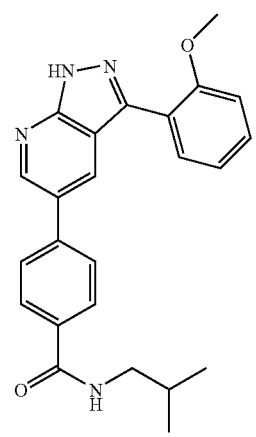

MS: m/z 401 [MH$^+$].

TABLE 12-continued
Structure
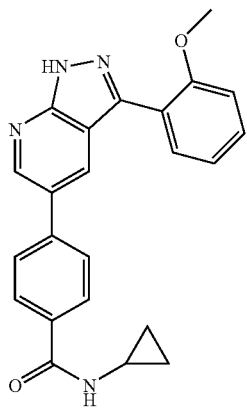
MS: m/z 385 [MH+].
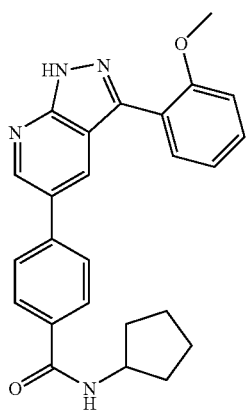
MS: m/z 413 [MH+].
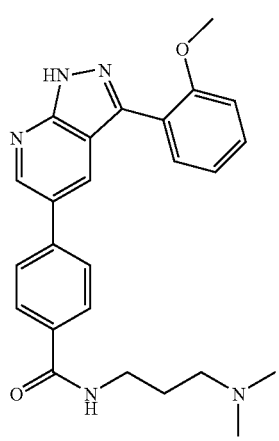
MS: m/z 430 [MH+].
TABLE 12-continued
Structure
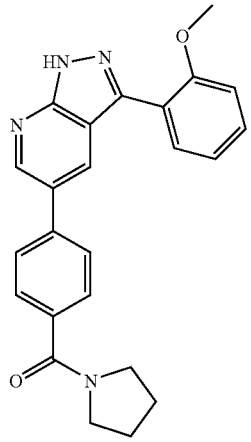
MS: m/z 399 [MH+].
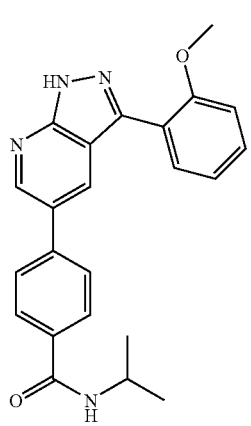
MS: m/z 387 [MH+].
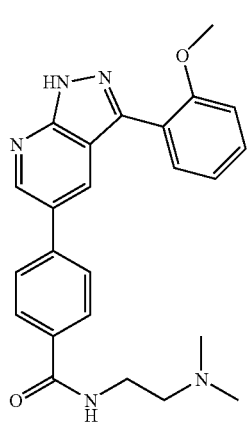
MS: m/z 416 [MH+].

Method 17:

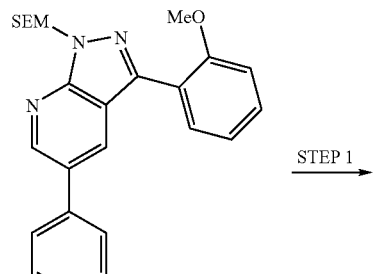

STEP 1

Step 1: Synthesis of 3-(2-Methoxy-phenyl)-5-(3-pyrrolidin-1-ylmethyl-phenyl)-1H-pyrazolo[3,4-b]pyridine To a solution of 3-[3-(2-Methoxy-phenyl)-1-(2-trimethyl-silanyl-ethoxymethyl)-1H-pyrazolo[3,4-b]pyridin-5-yl]-benzaldehyde (23 mg, 0.050 mmol) and Pyrrolidine (5 ul, 0.082 mmol) in 1.5 ml dichloethane was added 3 ul of AcOH. The mixture was stirred at room temperature for 30 mins, and then to the mixture was added sodium trioxyacetylborohydride (22 mg, 0.10 mmol) in one portion. The reaction was continued at room temperature for another 2 hrs the mixture was then concentrated to yield the SEM product which was treated with a solution of 5% perchlorate in acetic acid (2 mL) at room temperature for 1 hr. Solvents were evaporated, the residue was neutralized with sodium bicarbonate powder and then purified by flash silica gel chromatography using ethyl acetate then a mixture of EtOAc/DCM/MeOH/NH4OH (4/4/1/0.05) to afford 3-(2-Methoxy-phenyl)-5-(3-pyrrolidin-1-ylmethyl-phenyl)-1H-pyrazolo[3,4-b]pyridine (8.50 mg, 44% yield) as a white solid. $^1$H NMR (500 MHz, CD$_3$OD) δ 1.89 (d, J=3 Hz, 4H), 2.76 (d, J=1.5 Hz, 4H), 3.89 (s, 2H), 3.9 (s, 2H), 7.11 (t, J=1 Hz, 1H), 7.22 (d, J=8 Hz, 1H), 7.42 (t, J=7 Hz, 1H), 7.47 (d, J=1.5 Hz, 1H), 7.48 (d, J=2 Hz, 1H), 7.51 (d, J=2.5 Hz, 1H), 7.65 (t, J=6.75 Hz, 1H), 7.72 (s, 1H), 8.39 (d, J=2.5 Hz, 1H), 8.83 (d, J=2 Hz, 1H). MS: m/z 385 [MH$^+$].

Other Compounds Prepared by Method 17:

TABLE 13

| Structure |
| --- |
| MS: m/z 489 [MH$^+$]. |
| MS: m/z 386 [MH$^+$]. |
| MS: m/z 403 [MH$^+$]. |
| MS: m/z 471 [MH$^+$]. |

TABLE 13-continued

Structure

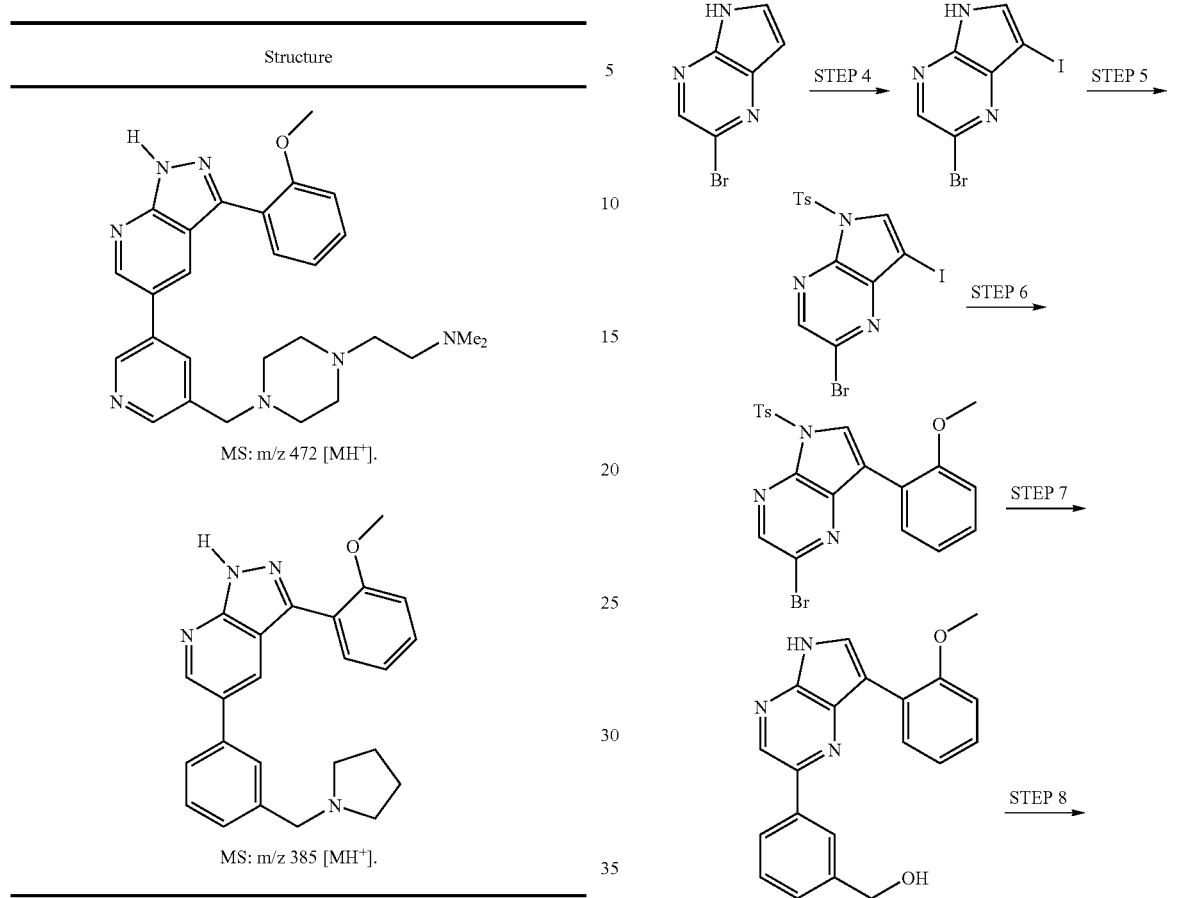

MS: m/z 472 [MH+].

MS: m/z 385 [MH+].

Method 18:

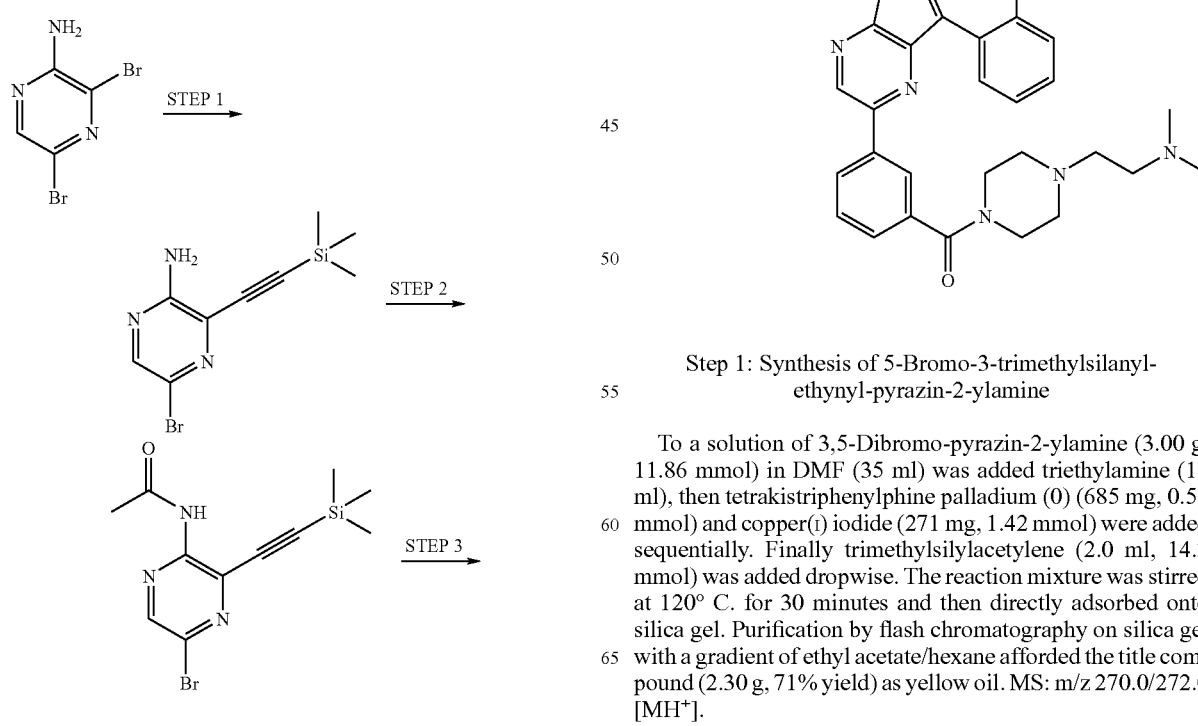

Step 1: Synthesis of 5-Bromo-3-trimethylsilanyl-ethynyl-pyrazin-2-ylamine

To a solution of 3,5-Dibromo-pyrazin-2-ylamine (3.00 g, 11.86 mmol) in DMF (35 ml) was added triethylamine (16 ml), then tetrakistriphenylphine palladium (0) (685 mg, 0.59 mmol) and copper(I) iodide (271 mg, 1.42 mmol) were added sequentially. Finally trimethylsilylacetylene (2.0 ml, 14.3 mmol) was added dropwise. The reaction mixture was stirred at 120° C. for 30 minutes and then directly adsorbed onto silica gel. Purification by flash chromatography on silica gel with a gradient of ethyl acetate/hexane afforded the title compound (2.30 g, 71% yield) as yellow oil. MS: m/z 270.0/272.0 [MH+].

Step 2: Synthesis of N-(5-Bromo-3-trimethylsilanyl-ethynyl-pyrazin-2-yl)-acetamide To a solution of 5-Bromo-3-trimethylsilanylethynyl-pyrazin-2-ylamine (2.30 g, 8 mmol) in anhydrous THF (35 ml) and pyridine (1.62 ml, 20.0 mmol) was added acetyl chloride (682 µl, 9.6 mmol). The mixture was stirred at room temperature overnight, and then stirred at 60° C. for 5 hours. Solvents were removed in vacuum and the resulting brown residue was purified by silica gel chromatogrpahy with a gradient of ethyl acetate/hexane to afford the title compound (474 mg, 1.52 mmol) as light yellow as off white solid. MS: m/z 311.9/313.9 [MH$^+$].

Step 3: Synthesis of 2-Bromo-5H-pyrrolo[2,3-b]pyrazine

To a solution of N-(5-Bromo-3-trimethylsilanylethynyl-pyrazin-2-yl)-acetamide (474 mg, 1.52 mmol) in THF (4 ml) was added dropwise a 1 M solution of tetra-n-butyl ammonium fluoride in THF (3.3 ml, 3.3 mmol). After stirring at reflux for 15 hours, the reaction mixture was concentrated in vacuum and water added. The aqueous layer was extracted three times with dichloromethane and the combined extracts were directly adsorbed on silica gel. Purification by silica gel chromatography with a gradient of ethyl acetate/hexanes afforded the title compound (130 mg, 43% yield) as a yellow solid. $^1$H-NMR (500 MHz, d$_6$-DMSO) δ 12.38 (s br, 1H), 8.38 (s, 1H), 7.95 (d, 3.5 Hz, 1H), 6.61 (d, 3.5 Hz, 1H). MS: m/z 197.9/199.9 [MH$^+$].

Step 4: Synthesis of 2-Bromo-7-iodo-5H-pyrrolo[2,3-b]pyrazine

To a solution of 2-Bromo-5H-pyrrolo[2,3-b]pyrazine (258 mg, 1.3 mmol) in acetone (5 ml) was added N-iodosuccinimide (324 mg, 1.44 mmol) in one portion. The reaction mixture was stirred at room temperature for 45 minutes. The resulting precipitate was filtered off, washed with a minimal amount of acetone, and dried in vacuum to give the title compound as a light brown solid $^1$H-NMR (500 MHz, d$_6$-DMSO) δ 12.81 (s br, 1H), 8.40 (s, 1H), 8.19 (d, 3.0 Hz, 1H). MS: m/z 323.8/325.8 [MH$^+$].

Step 5: Synthesis of 2-Bromo-7-iodo-5-(toluene-4-sulfonyl)-5H-pyrrolo[2,3-b]pyrazine To a suspension of 2-Bromo-7-iodo-5H-pyrrolo[2,3-b]pyrazine (290 mg, 0.895 mmol) in THF (5 ml) was added NaH (60%, 43 mg, 1.08 mmol) in one portion at 0° C. The resulting mixture was stirred for 20 minutes before a solution of para-toluenesulfonyl chloride (188 mg, 0.98 mmol) in THF (2 mL) was added. The reaction mixture was then stirred at room temperature for 3 hours. Solvents were removed and the resulting dark brown residue washed with aqueous KOH, water and dried to afford the title compound (423 mg, 99% yield) as a light brown solid. $^1$H-NMR (500 MHz, d$_6$-DMSO) δ 8.60 (d, 11.5 Hz, 1H), 7.99 (d, 11.5 Hz, 2H), 7.44 (d, 7.5 Hz, 2H), 2.34 (s, 3H). MS: m/z 477.8/479.8 [MH$^+$].

Step 6: Synthesis of 2-Bromo-7-(2-methoxy-phenyl)-5-(toluene-4-sulfonyl)-5H-pyrrolo[2,3-b]pyrazine A 50-ml round bottom flask was charged with 2-Bromo-7-iodo-5-(toluene-4-sulfonyl)-5H-pyrrolo[2,3-b]pyrazine (423 mg, 0.885 mmol), 2-methoxyphenylboronic acid (148 mg (0.973 mmol) and dichlorobis(triphenylphosphino)palladium(II) (31 mg, 0.04 mmol). To this mixture was added acetonitrile (10 mL) and a 2 M aqueous solution of sodium bicarbonate (5 mL). The reaction mixture was stirred at 40° C. for 1 hour, then 55° C. for another hour. The crude reaction mixture was distributed between ethyl acetate and a saturated aqueous solution of sodium bicarbonate. The aqueous phase was then extracted with ethyl acetate and the combined organic phases were dried over sodium sulfate, filtered and concentrated. The crude product was then purified by flash silica gel chromatography using a gradient of ethyl acetate in hexanes to afford 2-Bromo-7-(2-methoxy-phenyl)-5-(toluene-4-sulfonyl)-5H-pyrrolo[2,3-b]pyrazine (139 mg, 34% yield) as a light yellow solid; the bis-addition product 2,7-Bis-(2-methoxy-phenyl)-5-(toluene-4-sulfonyl)-5H-pyrrolo[2,3-b]pyrazine (213 mg, 50% yield) was also obtained. MS: m/z 457.9/460.0 [MH$^+$]; MS: m/z 486.1 [MH$^+$] (bis-addition product).

Step 7: Synthesis of 3-[7-(2-Methoxy-phenyl)-5H-pyrrolo[2,3-b]pyrazin-2-yl]-benzoic acid A mixture of 2-Bromo-7-(2-methoxy-phenyl)-5-(toluene-4-sulfonyl)-5H-pyrrolo[2,3-b]pyrazine (70 mg, 0.15 mmol), 3-(4,4,5,5-Tetramethyl-[1,3,2]dioxaborolan-2-yl)-benzoic acid (57 mg, 0.23 mmol) and dichlorobis(triphenylphosphino)palladium(II) (5.4 mg, 0.008 mmol) in acetonitrile (2 mL) and aqueous solution of sodium carbonate (2M, 2 mL) was irradiated in a Personal Chemistry Optimizer at 95° C. for 20 minutes. The crude reaction mixture was distributed between dichloromethane and a saturated aqueous solution of sodium bicarbonate. The aqueous phase was then extracted with dichloromethane and the combined organic phases were dried over sodium sulfate, filtered and concentrated.

The crude brown residue was then dissolved in MeOH (2 mL) and 5N KOH (150 µL) was added. The mixture was then stirred at 40° C. for 2 hours before the solvents were removed. The resulting yellow residue was washed with diluted HCl (2 ml), water, and then dried to afford the crude acid 3-[7-(2-Methoxy-phenyl)-5H-pyrrolo[2,3-b]pyrazin-2-yl]-benzoic acid, which was used directly in Step 8. MS: m/z 346.0 [MH$^+$].

Step 8: Synthesis of [4-(2-Dimethylamino-ethyl)-piperazin-1-yl]-{3-[7-(2-methoxy-phenyl)-5H-pyrrolo[2,3-b]pyrazin-2-yl]-phenyl}-methanone To a mixture of 3-[7-(2-Methoxy-phenyl)-5H-pyrrolo[2,3-b]pyrazin-2-yl]-benzoic acid (35 mg, 0.1 mmol), EDCI (77 mg, 0.40 mmol), HBTU (3.8 mg, 0.01 mmol) and diisopropylethylamine (175 µl, 1.0 mmol) in DMF (1 mL) was added 2-(dimethylamino)ethylpiperazine (55 µl, 0.3 mmol). The mixture was stirred at 70° C. for 5 hours before the solvents were removed. The resulting yellow oil was washed with water, dissolved in DMSO and purified on reverse phase HPLC to afford the title compound (8.6 mg, 12% over 2 steps) as yellow solid. MS: m/z 485.2 [MH$^+$].

Other compounds prepared by method 18:

TABLE 14

Structure

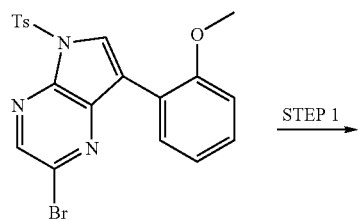

MS: m/z 442.2 [MH+].

Method 19:

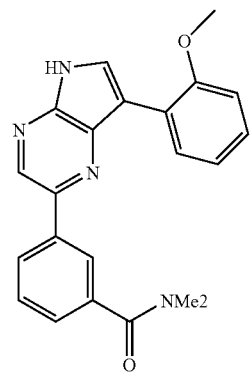

STEP 1

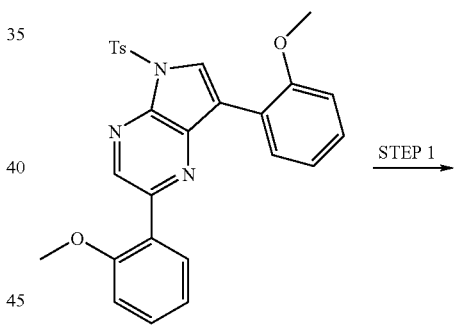

Step 1: Synthesis of 3-[7-(2-Methoxy-phenyl)-5H-pyrrolo[2,3-b]pyrazin-2-yl]-N,N-dimethyl-benzamide A mixture of 2-Bromo-7-(2-methoxy-phenyl)-5-(toluene-4-sulfonyl)-5H-pyrrolo[2,3-b]pyrazine (30 mg, 0.065 mmol), 3-dimethylaminocarbonylphenyl boronic acid (25.3 mg, 0.130 mmol) and dichlorobis(triphenylphosphino)palladium(II) (2.5 mg, 0.003 mmol) in acetonitrile (1 mL) and aqueous solution of sodium bicarbonate (2M, 1 mL) was irradiated in a Personal Chemistry Optimizer at 90° C. for 15 minutes. The crude reaction mixture was distributed between dichloromethane and a saturated aqueous solution of sodium bicarbonate. The aqueous phase was then extracted with dichloromethane and the combined organic phases were dried over sodium sulfate, filtered and concentrated. The crude brown residue was then dissolved in MeOH (5 mL), 5N KOH (50 μL) and the mixture was stirred at room temperature for 75 minutes. Removal of the solvents resulted in a yellow residue, which was then purified by flash silica gel chromatography using a gradient of ethyl acetate in hexanes, then 10% MeOH in EtOAc to afford 3-[7-(2-Methoxy-phenyl)-5H-pyrrolo[2,3-b]pyrazin-2-yl]-N,N-dimethyl-benzamide (13.0 mg, 54% yield) as a pale yellow solid. $^1$H-NMR (500 MHz, CD3OD) δ 8.89 (m, 1H), 8.80 (m, 1H), 8.40 (m, 1H), 8.25 (m, 2H), 7.62 (m, 1H), 7.50 (m, 1H), 7.25 (m, 1H), 7.10 (m, 2H), 3.97 (m, 3H), 3.17 (m, 3H), 3.10 (m, 3H). MS: m/z 373.1 [MH+].

Other Compounds Prepared by Method 19:

TABLE 15

Structure

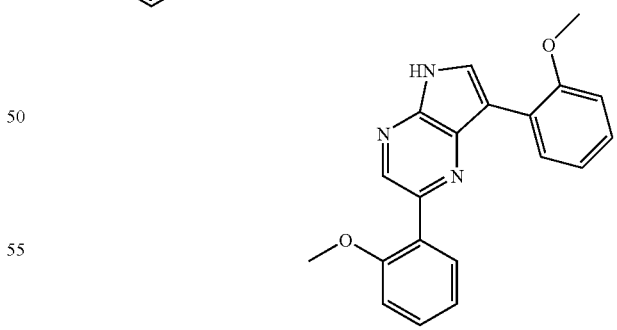

MS: m/z 399.1 [MH+].

Method 20:

Step 1: Synthesis of 2,7-Bis-(2-methoxy-phenyl)-5H-pyrrolo[2,3-b]pyrazine

To a solution of 2,7-Bis-(2-methoxy-phenyl)-5-(toluene-4-sulfonyl)-5H-pyrrolo[2,3-b]pyrazine (200 mg, 0.412 mmol) in MeOH (5 mL) was added a solution of NaOH (66 mg, 1.65 mmol) in water (200 μL). The mixture was stirred at room temperature for 3.5 hours before the solvents were removed. The resulting yellow residue was then purified by flash silica gel chromatography using a gradient of ethyl acetate in hexanes to afford 2,7-Bis-(2-methoxy-phenyl)-5H-pyrrolo[2,3-b]pyrazine (43 mg, 32% yield) as a pale yellow solid. $^1$H-NMR (500 MHz, CD3OD) δ 12.21 (s br, 1H), 8.80 (dd, 6.0 Hz, 1.75 Hz, 1H), 8.69 (s, 1H), 7.76 (dd, 6.0 Hz, 1.75 Hz, 1H), 7.43 (dt, 7.5 Hz, 1.75 Hz, 1H), 7.20 (m, 2H), 7.13 (m, 2H), 7.04 (t, 7.3 Hz, 1H), 3.92 (s, 3H), 3.85 (s, 3H). MS: m/z 332.1 [MH$^+$].

Method 21:

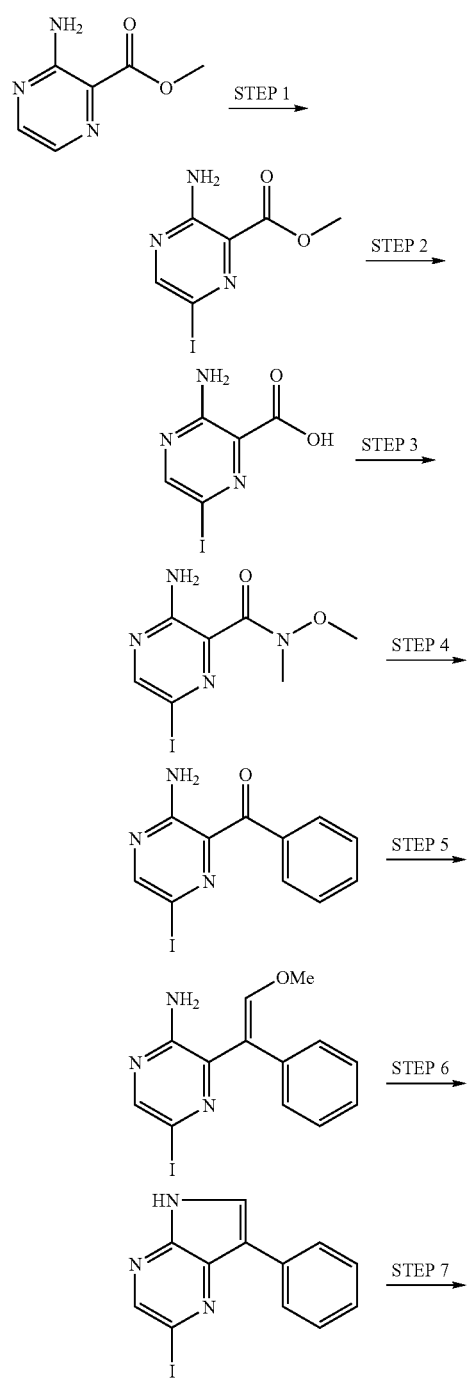

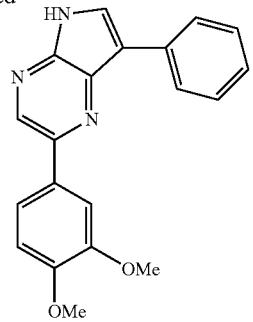

Step 1: Synthesis of 3-amino-6-iodo-pyrazine-2-carboxylic acid methyl ester

Methyl 3-amino-2-pyrazinecarboxylate (10 g, 65.3 mmol) and N-iodosuccinimide (24 g, 106.7 mmol) were dissolved in anhydrous DMF (150 mL) and the mixture was stirred at 70° C. for 15 hours under a nitrogen atmosphere. The mixture was then cooled to room temperature and a saturated aqueous solution of sodium thiosulfate (400 mL) was added. The suspension was sonicated for 15 minutes, concentrated under vacuum and dispersed in water. The crude product was filtered off and washed with cold ethanol. The residue was crystallized from ethanol, using decolorizing charcoal to afford 3-amino-6-iodo-pyrazine-2-carboxylic acid methyl ester (11.2 g, 61% yield) as orange needles. 1H-NMR (d6-DMSO) δ: 8.57 [1H] s, 7.59 [2H] s, br, 3.93 [3H] s. MS: m/z 280 [MH$^+$].

Step 2: Synthesis of 3-amino-6-iodo-pyrazine-2-carboxylic acid 3-amino-6-iodo-pyrazine-2-carboxylic acid methyl ester (45 g, 161 mmol) was dissolved in 750 ml of THF. 90 ml of water and 40 ml of a 4 M solution of lithium hydroxide in water was added. The mixture was stirred at room temperature for 2 hours or until TLC analysis showed only baseline material. A solution of 10% citric acid in water was added to adjust the pH to about 3-4. The mixture was diluted with dichloromethane and the organic phase was separated. The aqueous layer was extracted three times with dichloromethane and the combined organic phases were dried over sodium sulfate and evaporated. The residue was dried in vacuo to afford 37.0 g (140 mmol; 87% yield) of 3-amino-6-iodo-pyrazine-2-carboxylic acid as a yellow powder. $^1$H-NMR (d6-DMSO) δ: 11.70 s, weak, 8.44 [1H] s, 7.50 [2H] s, br. MS: m/z 266 [MH$^+$].

Step 3: Synthesis of 3-amino-6-iodo-pyrazine-2-carboxylic acid methoxy-methyl-amide 27.50 g (0.104 mol) of 3-amino-6-iodo-pyrazine-2-carboxylic acid, 63.0 g (0.125 mol) of PyBOP (1-benzotriazolyloxy-tris(pyrrolidino)phosphonium hexafluorophosphate) and 18.70 g (0.193 mol) of N,O-dimethylhydroxylamine hydrochloride were placed in a nitrogen flushed flask and then dissolved in a mixture of 100 ml of anhydrous DMF and 27 ml of N,N-di-iso-propylethylamine. The mixture was heated to 80° C. for 16 hours. The solvent was evaporated at 50-60° C. under reduced pressure to afford a dark oil. The oil was extracted three to four times with 300 ml of toluene. The toluene phases were combined and evaporated. The resulting oil was purified via chromatography on silica gel using a gradient of ethyl acetate in hexanes to afford 18.40 g (59.72 mmol; 58%) of 3-amino-6-iodo-pyrazine-2-carboxylic acid methoxy-methyl-amide as a yellow solid. $^1$H-NMR (d6-DMSO) δ: 8.28 [1H] s, 6.78 [2H] s, 3.66 [3H] s, 3.25 [3H] s. MS: m/z 309 [MH$^+$].

Step 4: Synthesis of (3-amino-6-iodo-pyrazin-2-yl)-phenyl-methanone 8.00 g (25.97 mmol) of 3-amino-6-iodo-pyrazine-2-carboxylic acid methoxy-methyl-amide was dissolved in 100 ml of anhydrous THF under nitrogen. The solution was cooled to 55° C. and 27 ml of a 3 M solution of phenylmagnesium bromide in ether was added. The mixture was allowed to warm to 10° C. and a solution of 10% citric acid in water was added. The mixture was diluted with dichloromethane and the phases were separated. The aqueous phase was extracted three times with dichloromethane and the combined organic phases were dried over sodium sulfate and evaporated. The resulting solid was crystallized from ethanol to afford 5.74 g (17.66 mmol; 68%) of (3-amino-6-iodo-pyrazin-2-yl)-phenyl-methanone as yellow-orange crystals. $^1$H-NMR (d6-DMSO) δ: 8.52 [1H] s, 7.94 [2H] s, br, 7.85 [2H] d, 7.62 [1H] t, 7.52 [2H] t. MS: m/z 326 [MH$^+$].

Step 5: Synthesis of 5-iodo-3-(2-methoxy-1-phenyl-vinyl)-pyrazin-2-ylamine 2.52 g (12.6 mmol) of potassium bis(trimethylsilyl)amide was dissolved in 150 ml of anhydrous THF under nitrogen. 3.80 g (11.1 mmol) of methoxymethyltriphenylphosphonium chloride was added and the mixture stirred at room temperature for 1 hour. To the resulting mixture was added 2.50 g (7.69 mmol) of (3-amino-6-iodo-pyrazin-2-yl)-phenyl-methanone and the reaction mixture was stirred at room temperature for 1 hour. The resulting reaction mixture was heated to reflux for 20 hours. After cooling the mixture was diluted with dichloromethane and washed with a saturated aqueous solution of ammonium chloride in water and dried over sodium sulfate. The solvent was evaporated and the residue purified by chromatography on silica gel using a gradient of ethyl acetate in hexanes to afford 1.942 g (5.50 mmol; 72%) of partially resolved E- and Z-5-iodo-3-(2-methoxy-1-phenyl-vinyl)-pyrazin-2-ylamine as a pale yellow solid. $^1$H-NMR (d6-DMSO) δ: isomer A 8.12 [1H] s, 7.33-7.26 [4H] m, 7.20 [1H] m, 6.66 [1H] s, 6.00 [2H] s, br, 3.81 [3H] s; isomer B 8.09 [1H] s, 7.27 [2H] t, 7.17 [1H] t, 7.11 [2H] d, 6.98 [1H] s, 6.24 [2H] s, br, 3.76 [3H] s. MS: m/z 354 [MH$^+$].

Step 6: Synthesis of 5-iodo-3-phenyl-1H-pyrrolo[2,3-b]pyrazine 780 mg of 5-iodo-3-(2-methoxy-1-phenyl-vinyl)-pyrazin-2-ylamine (E-, Z-form or mixture) was dispersed in 40 ml of a 1:1 mixture of dilute hydrochloric acid in water (approx. 1-2 N) and ethanol. The mixture was heated to reflux for 2 hours. Ice was added to the resulting suspension and the precipitate filtered off to afford 480 mg of 5-iodo-3-phenyl-1H-pyrrolo[2,3-b]pyrazine as a pale yellow powder. The filtrate was made basic by addition of sodium bicarbonate and extracted three times with dichloromethane. The combined extracts were dried over sodium sulfate and evaporated. The residue was crystallized from ethanol to afford 76 mg of 5-iodo-3-phenyl-1H-pyrrolo[2,3-b]pyrazine as green-brown crystalline needles for a combined yield of 556 mg (78%). $^1$H-NMR (d6-DMSO) δ: 12.56 [1H] s, br, 8.53 [1H] s, 8.46 [1H] d, 8.14 [2H] d, 7.45 [2H] dd, 7.25 [1H] dd. MS: m/z 322 [MH$^+$].

Step 7: Synthesis of 5-(3,4-dimethoxy-phenyl)-3-phenyl-1H-pyrrolo[2,3-b]pyrazine 50 mg (0.16 mmol) of 5-iodo-3-phenyl-1H-pyrrolo[2,3-b]pyrazine, 38 mg (0.20 mmol) of 3,4-dimethoxyphenylboronic acid and 6 mg (5 mol %) of dichlorobis(triphenylphosphino)palladium(II) were placed in a vial and 1 ml of acetonitrile and 1 ml of a 2 M aqueous solution of sodium carbonate were added and the mixture irradiated in a Personal Chemistry® microwave reactor to 165° C. for 1200 sec. The resulting mixture was distributed between 15 ml of a saturated aqueous solution of sodium bicarbonate and 75 ml of dichloromethane. The organic phase was dried over sodium sulfate and evaporated. The crude was purified via flash chromatography on silica gel using a gradient of methanol in dichloromethane. The product isolated was crystallized from hot ethanol to afford 14 mg (43 μmol, 27% yield) of 5-(3,4-dimethoxy-phenyl)-3-phenyl-1H-pyrrolo[2,3-b]pyrazine as an orange powder. $^1$H-NMR (d6-DMSO) δ: 12.30 [1H] s, 8.92 [1H] s, 8.43 [1H] s, 8.35 [2H] d, 7.80 [1H] (m), 7.79 [1H] d (m), 7.46 [2H] dd, 7.25 [1H] dd (d), 7.13 [1H] d, 3.92 [3H] s, 3.84 [3H] s. MS: m/z 332 [MH$^+$].

Other Compounds Prepared by Method 21:

TABLE 16

Structure

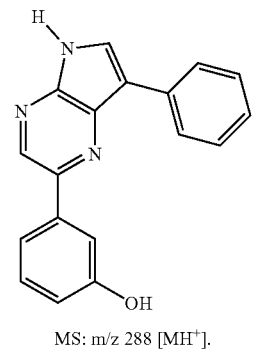

MS: m/z 288 [MH$^+$].

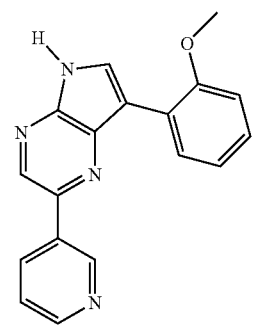

MS: m/z 303 [MH$^+$].

TABLE 16-continued

| Structure |
|---|
| 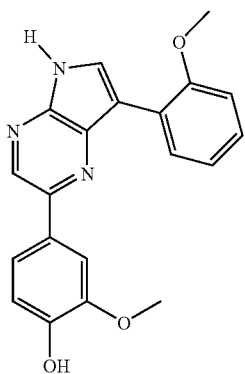 MS: m/z 318 [MH+]. |
| 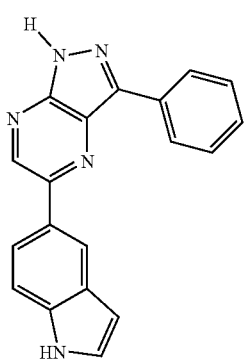 MS: m/z 311 [MH+]. |
| 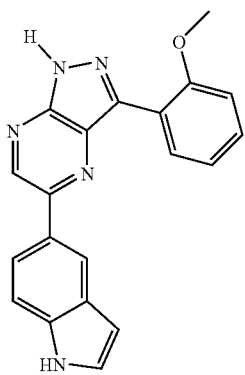 MS: m/z 341 [MH+]. |
| 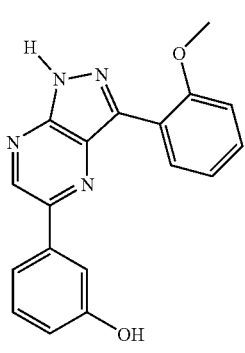 MS: m/z 318 [MH+]. |

TABLE 16-continued

| Structure |
|---|
| 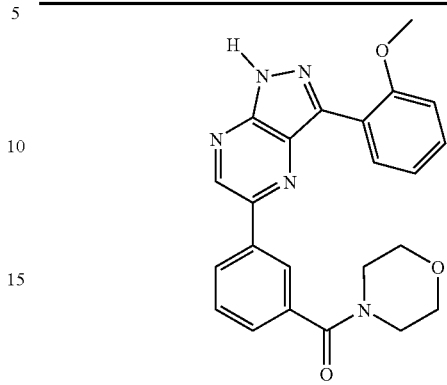 MS: m/z 415 [MH+]. |

Method 22:

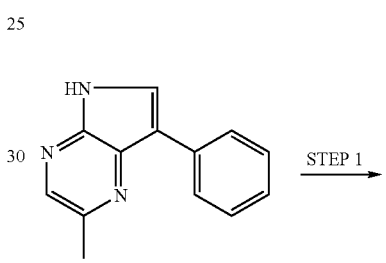

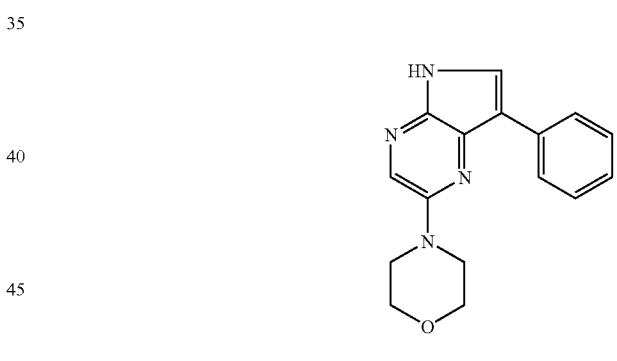

Step 1: Synthesis of 5-(morpholin-4-yl)-3-phenyl-1H-pyrrolo[2,3-b]pyrazine 25 mg (80 μmol) of 5-iodo-3-phenyl-1H-pyrrolo[2,3-b]pyrazine was dissolved in 1 ml of morpholine. 200 μl of glacial acetic acid was added and the mixture heated in a Personal Chemistry® microwave reactor to 250° C. for 2400-4800 sec. The crude was purified by flash chromatography on silica gel without prior workup using a gradient of ethyl acetate in hexanes to afford 13 mg (46 μmol, 58% yield) of 2-morpholin-4-yl-7-phenyl-1H-pyrrolo[2,3-b]pyrazine as a beige solid. $^1$H-NMR (d6-DMSO) δ: 11.89 [1H] s, 8.19 [1H] s, 8.18 [2H] d, 7.39 [2H] dd, 7.17 [1H] dd, 3.80 [4H] t, 3.52 [4H] t. MS, m/z: 281 [MH+].

TABLE 17

| Structure |
|---|
| 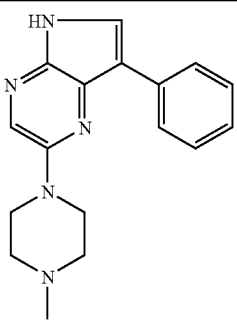<br>MS: m/z 294 [MH+] |
| 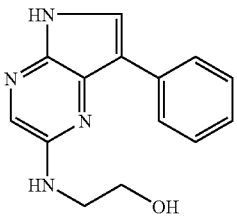<br>MS: m/z 269 [MH+] |

Method 23:

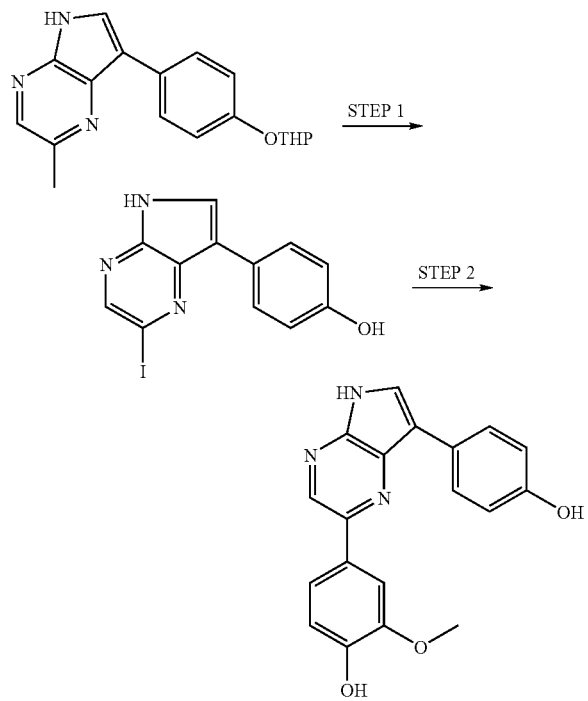

Step 1: Synthesis of
4-(5-iodo-1H-pyrrolo[2,3-b]pyrazin-3-yl)-phenol 80 mg of 5-iodo-3-{2-methoxy-1-[4-(tetrahydro-pyran-2-yloxy)-phenyl]-vinyl}-pyrazin-2-ylamine was dispersed in 70 ml of dilute (1-2 N) aqueous hydrochloric acid. Methanol was added to dissolve the starting material (10-20% v/v) to afford a clear solution. 0.5 ml of concentrated hydrochloric acid was added and the mixture was heated to reflux for 7 hours. The mixture was cooled to room temperature and allowed to stir for 16 hours. The mixture was neutralized by addition of sodium bicarbonate and water added as needed to keep salts in solution. The resulting mixture was extracted four times with dichloromethane and the combined organic phases were, dried over sodium sulfate and evaporated to afford 428 mg (1.27 mmol, 85% yield) of 4-(5-iodo-1H-pyrrolo[2,3-b]pyrazin-3-yl)-phenol as an orange solid of sufficient purity (>85%), which could be recrystallized from dichloromethane-ethyl acetate to afford 195 mg (578 μmol, 39% yield) of pure 4-(5-iodo-1H-pyrrolo[2,3-b]pyrazin-3-yl)-phenol as yellow-orange crystals. $^1$H-NMR (d6-DMSO) δ: 12.37 [1H] (d), 9.43 [1H] s, 8.49 [1H] s, 8.26 [1H] d, 7.92 [2H] d, 8.85 [2H] d. MS: m/z 338 [MH+].

Step 2: Synthesis of 4-{5-[3-methoxy-4-hydroxyphenyl]-1H 1-pyrrolo[2,3-b]pyrazin-3-yl}-phenol 84 mg (0.25 mmol) of 4-(5-iodo-1H-pyrrolo[2,3-b]pyrazin-3-yl)-phenol, 120 mg (0.33 mmol) of 2-[3-methoxy-4-(4-methoxy-benzyloxy)-phenyl]-4,4,5,5-tetramethyl-[1,3,2]dioxaborolane and 15 mg (8 mol %) of dichlorobis (triphenylphosphino)palladium(II) were placed in a vial and 1.5 ml of acetonitrile and 1.5 ml of a 2 M aqueous solution of sodium carbonate were added. The mixture was irradiated in a Personal Chemistry® microwave reactor to 165° C. for 1200 sec. The resulting mixture was distributed between dichloromethane and a saturated aqueous solution of sodium bicarbonate. The aqueous layer was extracted twice with dichloromethane and the combined organic phases were dried over sodium sulfate and evaporated. The crude was purified by flash chromatography on silica gel using a gradient of ethyl acetate in hexanes. The resulting intermediate was dissolved in 120 ml of dichloromethane and 1.5 g (2.12 mmol) of PS-thiophenol (Argonaut Technologies) was added. To this was added 2 ml of trifluoroacetic acid and the mixture stirred at room temperature for 1 hour. The resin was filtered off and washed with dichloromethane. The filtrate was washed with a saturated aqueous solution of sodium bicarbonate. The phases were separated and the aqueous layer extracted twice with ethyl acetate. All organic phases were combined, dried over sodium sulfate and evaporated. The residue was heated up with acetonitrile, cooled down to room temperature and the supernatant was removed. The residue was dried in vacuo to afford 15 mg (45 μmol, 18% yield) of 4-{5-[3-methoxy-4hydroxyphenyl]-1H-pyrrolo[2,3-b] pyrazin-3-yl}-phenol as a beige powder. $^1$H-NMR (d6-DMSO) δ: 12.06 [1H] d, 9.35 [1H] s, 9.30 [1H] s, 8.83 [1H] s, 8.20 [1H] d, 8.12 [2H] d (m), 7.75 [1H] d, 7.65 [1H] dd, 6.93 [1H] d, 6.85 [2H] d (m), 3.91 [3H] s. MS, m/z: 334 [MH+].

Method 24

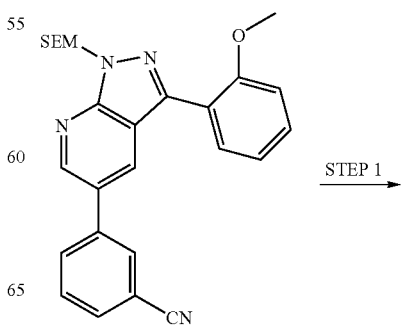

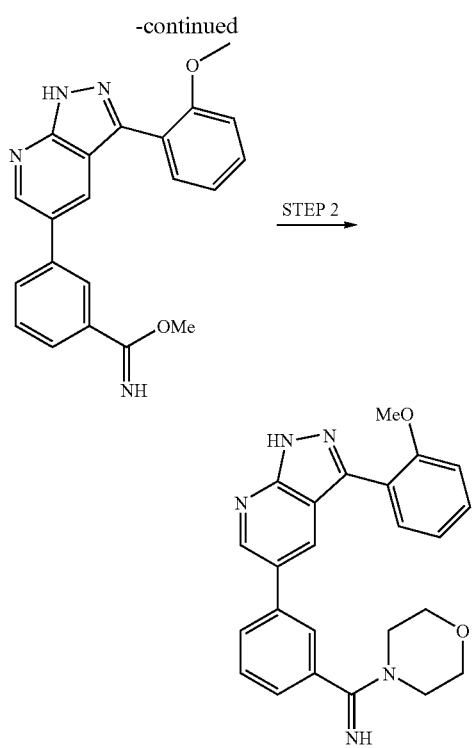

Step 1: Synthesis of methyl 3-(3-(2-methoxyphenyl)-1H-pyrazolo[3,4-b]pyridin-5-yl)benzimidate HCl gas was bubbled through a suspension of 3-[3-(2-Methoxy-phenyl)-1-(2-trimethylsilanyl-ethoxymethyl)-1H-pyrazolo[3,4-b]pyridin-5-yl]-benzonitrile (40 mg, 0.088 mmol) in 2.5 ml of anhydrous MeOH for 3 minutes at 0° C. After stirring for 23 hours at room temperature, ether (10 mL) was added and precipitation occurred. The solid was collected after filtration and dried to afford methyl 3-(3-(2-methoxyphenyl)-1H-pyrazolo[3,4-b]pyridin-5-yl)benzimidate as a yellow solid.

Step 2: Synthesis of C-{3-[3-(2-Methoxy-phenyl)-1H-pyrazolo[3,4-b]pyridin-5-yl]-phenyl}-C-morpholin-4-yl-methyleneamine A solution of methyl 3-(3-(2-methoxyphenyl)-1H-pyrazolo[3,4-b]pyridin-5-yl)benzimidate from Step in MeOH (1.0 mL) was added morphiline (15.3 mg, 0.176 mmol) and triethylamine (90 mg, 0.88 mmol), the mixture was stirred at room temperature for 3 days. The solvent was then removed and the crude product purified by reverse phase HPLC to afford C-{3-[3-(2-Methoxy-phenyl)-1H-pyrazolo[3,4-b]pyridin-5-yl]-phenyl}-C-morpholin-4-yl-methyleneamine (3.7 mg, 10% yield two steps) as a white solid. $^1$H-NMR (500 MHz, CD3OD) δ 8.86 (d, 2 Hz, 1H), 8.45 (d, 2 Hz, 1H), 8.37 (br s, 1H), 8.02 (m, 1H), 7.96 (t, 1.8 Hz, 1H), 7.76 (t, 7.8 Hz, 1H), 7.66 (dd, 1.8 Hz, 7.8 Hz, 1H), 7.63 (m, 1H), 7.49 (m, 1H), 7.21 (d, 8 Hz, 1H), 7.12 (dt, 1 Hz, 7.8 Hz, 1H), 3.95 (m, 2H), 3.88 (s, 3H), 3.82 (m, 2H) 3.78 (m, 2H), 3.59 (m, 2H). MS: m/z 414.1 [MH$^+$].

Other Compounds Prepared by Method 24:

TABLE 18

| Structure |
|---|
| <br>MS: m/z 412.1 [MH$^+$]. |

Bioassays:

Kinase assays known to those of skill in the art may be used to assay the inhibitory activities of the compounds and compositions of the present invention. Kinase assays include, but are not limited to, the following examples.

Although the first of these examples uses the kinase domain of a mutant form of Abl T315I ("Abl T315I KD"), the kinase assays may use various forms of mutant and wild type enzymes, including, for example, the entire protein, the kinase domain, or a portion thereof (e.g. Abl Y393F). The kinases used in the assays may also be of varying phosphorylation states. In the c-Abl example, a mutant kinase at a zero phosphorylation state was used.

c-Abl Pyruvate Kinase/Lactate Dehydrogenase Coupled Enzyme Assay

In the c-Abl Pyruvate Kinase (PK)/Lactate Dehydrogenase (LDH) Coupled Assay the protein kinase dependant phosphorylation of a substrate peptide was coupled to the oxidation of NADH. The oxidation of NADH to NAD+ was detected by monitoring a decrease in absorbance at 340 nm.

Materials: Abl substrate peptide=EAIYAAPFAKKK-OH (Biopeptide, San Diego, Calif.); βNADH (Sigma Cat#N-8129, FW=709.4); 2M MgCl$_2$; 1M HEPES buffer, pH 7.5; Phosphoenolpyruvate (PEP) (Sigma Cat#P-7002, FW=234); Lactate dehydrogenase (LDH) (Worthington Biochemical Cat#2756); Pyruvate Kinase (PK) (Sigma Cat#P-9136); ATP (Sigma Cat#A-3377, FW=551); Greiner 384-well UV star plate; and purified and unphosphorylated T315I Abl kinase domain.

Stock Solutions: 10 mM NADH (7.09 mg/ml in miliQH$_2$O) made fresh daily; 10 mM Abl substrate peptide (13.4 mg/ml in miliQH$_2$O) stored at −20° C.; 100 mM HEPES buffer, pH 7.5 (5 ml 1M stock+45 ml miliQH$_2$O); 100 mM MgCl$_2$ (5 ml 2M MgCl$_2$+95 ml dH$_2$O); 100 mM PEP (23.4 mg/ml in dH$_2$O) stored at −20° C.; 10 mM ATP (5.51 mg/ml in dH$_2$O) stored at −20° C. (diluted 50 μl into total of 10 ml miliQH$_2$O daily=50 μM ATP working stock); 1000 U/ml PK (U/mg varies with lot) flash-frozen under liquid N$_2$ and stored at −80° C.; and 1000 U/ml LDH (U/mg varies with lot) flash-frozen under liquid N$_2$ and stored at −80° C.

Standard Assay Setup for 384-well format (50 µl reaction): 300 µM NADH; 10 mM MgCl$_2$; 2 mM PEP; 45 U/ml PK; 60 U/ml LDH; 200 µM Abl substrate peptide; 2.5 µl test compound (in DMSO); 2 µg/ml Abl kinase domain; 10 µM ATP; 100 mM HEPES buffer. Positive controls contained DMSO with no test compound. Negative controls contained 5 µl of 0.5M EDTA (50 mM in the assay). The dephosphorylated form of the c-Abl T315I mutant was used in the biochemical screening assays. The kinase reaction was initiated at time t=0 by the addition of ATP.

Activity was measured by following the time-dependent loss of NADH by absorbance spectroscopy at 340 nm. The linear portion of the resulting progress curve was then analyzed by linear regression to get the activity in absorbance units/time, reported as the slope of that best fit line (moles/unit time can be calculated from using molar extinction coefficient for NADH at 340 nm, 6250M$^{-1}$ cm$^{-1}$).

Data was evaluated using the equation: $Z'=1-[3*(\sigma_++\sigma_-)/|\mu_+-\mu_-|]$ (Zhang, et al., 1999 J Biomol Screening 4(2) 67-73), where µ denotes the mean and a the standard deviation. The subscript designates positive or negative controls. The Z' score for a robust screening assay should be ≧0.50. The typical threshold=$\mu_+-3*\sigma_+$. Any value that falls below the threshold was designated a "hit".

Dose response was analyzed using the equation: $y=\min+\{(\max-\min)/(1+10^{[compound]-\log\ IC50})\}$, where y is the observed initial slope, max=the slope in the absence of inhibitor, min=the slope at infinite inhibitor, and the IC$_{50}$ is the [compound] that corresponds to 2 the total observed amplitude (Amplitude=max−min).

To measure modulation, activation, or inhibition of Abl KD, a test compound was added to the assay at a range of concentrations. Inhibitors may inhibit Abl KD activity at an IC$_{50}$ in the micromolar range, the nanomolar range, or, for example, in the subnanomolar range.

Additional Kinase Assays

In addition to the c-Abl PK/LDH coupled assay (above), homogeneous luminescence-based inhibitor screening assays were developed for c-Abl, MET, AurA, and PDK1 kinases (among others). Each of these assays made use of an ATP depletion assay (Kinase-Glo™, Promega Corporation, Madison, Wis.) to quantitate kinase activity. The Kinase-Glo™ format uses a thermostable luciferase to generate luminescent signal from ATP remaining in solution following the kinase reaction. The luminescent signal is inversely correlated with the amount of kinase activity.

cAbl Luminescence-based Enzyme Assay

Materials: Abl substrate peptide=EAIYAAPFAKKK-OH (Biopeptide, San Diego, Calif.), ATP (Sigma Cat#A-3377, FW=551), HEPES buffer, pH 7.5, Bovine serum albumin (BSA) (Roche 92423420), MgCl$_2$, Staurosporine (*Streptomyces* sp. Sigma Cat#85660-1 MG), white Costar 384-well flat-bottom plate (VWR Cat#29444-088), Abl kinase (see below), Kinase-Glo™ (Promega Cat#V6712).

Stock Solutions: 10 mM Abl substrate peptide (13.4 mg/ml in miliQH$_2$O) stored at −20° C.; 100 mM HEPES buffer, pH 7.5 (5 ml 1M stock+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 1% BSA (1 g BSA in 100 ml 0.1 M HEPES, pH 7.5, stored at −20° C.), 100 mM MgCl$_2$; 200 µM Staurosporine, 2X Kinase-Glo™ reagent (made fresh or stored at −20° C.).

Standard Assay Setup for 384-well format (20 µl kinase reaction, 40 µl detection reaction): 10 mM MgCl$_2$; 100 µM Abl substrate peptide; 0.1% BSA; 1 µl test compound (in DMSO); 0.4 µg/ml Abl kinase domain; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 30 min, then 20 µl of Kinase-Glo™ reagent were added to each well to quench the kinase reaction and initiate the luminescence reaction. After a 20 min incubation at 21° C., the luminescence was detected in a plate-reading luminometer.

MET Luminescence-Based Enzyme Assay

Materials: Poly Glu-Tyr (4:1) substrate (Sigma Cat# P-0275), ATP (Sigma Cat#A-3377, FW=551), HEPES buffer, pH 7.5, Bovine serum albumin (BSA) (Roche 92423420), MgCl$_2$, Staurosporine (*Streptomyces* sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml IM stock+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 1% BSA (1 g BSA in 100 ml 0.1M HEPES, pH 7.5, stored at −20° C.), 100 mM MgCl$_2$; 200 µM Staurosporine, 2X Kinase-Glo™ reagent (made fresh or stored at −20° C.).

Standard Assay Setup for 384-well format (20 µl kinase reaction, 40 µl detection reaction): 10 mM MgCl$_2$; 0.3 mg/ml poly Glu-Tyr; 0.1% BSA; 1 µl test compound (in DMSO); 0.4 µg/ml MET kinase; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 60 min, then 20 µl of Kinase-Glo™ reagent were added to each well to quench the kinase reaction and initiate the luminescence reaction. After a 20 min incubation at 21° C., the luminescence was detected in a plate-reading luminometer.

Aura Luminescence-Based Enzyme Assay

Materials: Kemptide peptide substrate=LRRASLG (Biopeptide, San Diego, Calif.), ATP (Sigma Cat#A-3377, FW=551), HEPES buffer, pH 7.5, 10% Brij 35 (Calbiochem Cat#203728), MgCl$_2$, Staurosporine (*Streptomyces* sp. Sigma Cat#85660-1MG), white Costar 384-well flat-bottom plate (VWR Cat#29444-088), Autophosphorylated AurA kinase (see below), Kinase-Glo™ (Promega Cat#V6712).

Stock Solutions: 10 mM Kemptide peptide (7.72 mg/ml in water), stored at −20° C.; 100 mM HEPES buffer+0.015% Brij 35, pH 7.5 (5 ml 1M HEPES stock+75 µL 10% Brij 35+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 100 mM MgCl$_2$; 200 µM Staurosporine, 2X Kinase-Glo™ reagent (made fresh or stored at −20° C.).

AurA Autophosphorylation Reaction: ATP and MgCl$_2$ were added to 1-5 mg/ml AurA at final concentrations of 10 mM and 100 mM, respectively. The autophosphorylation reaction was incubated at 21° C. for 2-3 h. The reaction was stopped by the addition of EDTA to a final concentration of 50 mM, and samples were flash frozen with liquid N$_2$ and stored at −80° C.

Standard Assay Setup for 384-well format (20 µl kinase reaction, 40 µl detection reaction): 10 mM MgCl$_2$; 0.2 mM Kemptide peptide; 1 µl test compound (in DMSO); 0.3 µg/ml Autophosphorylated AurA kinase; 10 µM ATP; 100 mM HEPES+0.015% Brij buffer. Positive controls contained DMSO with no test compound. Negative controls contained 5 µM staurosporine. The kinase reactions were initiated at time t=0 by the addition of ATP. Kinase reactions were incubated at 21° C. for 45 min, then 20 µl of Kinase-Glo™ reagent were added to each well to quench the kinase reaction and initiate the luminescence reaction. After a 20 min incubation at 21° C., the luminescence was detected in a plate-reading luminometer.

PDK1 Luminescence-Based Enzyme Assay

Materials: PDKtide peptide substrate=KTFCGTPEY-LAPEVRREPRILSEEEQEMFRDFDYIADWC (Upstate Cat# 12-401), ATP (Sigma Cat#A-3377, FW=551), HEPES buffer, pH 7.5, 10% Brij 35 (Calbiochem Cat#203728), $MgCl_2$, Staurosporine (*Streptomyces* sp. Sigma Cat#85660-1MG), white Costar 384-well flat-bottom plate (VWR Cat#29444-088), PDK1 kinase (see below), Kinase-Glo™ (Promega Cat#V6712).

Stock Solutions: 1 mM PDKtide substrate (1 mg in 200 µl, as supplied by Upstate), stored at −20° C.; 100 mM HEPES buffer, pH 7.5 (5 ml 1M HEPES stock+45 ml miliQ$H_2$O); 10 mM ATP (5.51 mg/ml in d$H_2$O) stored at −20° C. (diluted 25 µl into total of 10 ml miliQ$H_2$O daily=25 µM ATP working stock); 100 mM $MgCl_2$; 10% Brij 35 stored at 2-8° C.; 200 µM Staurosporine, 2X Kinase-Glo™ reagent (made fresh or stored at −20° C.).

Standard Assay Setup for 384-well format (20 µl kinase reaction, 40 µl detection reaction): 10 mM $MgCl_2$; 0.01 mM PDKtide; 1 µl test compound (in DMSO); 0.1 µg/ml PDK1 kinase; 5 µM ATP; 10 mM $MgCl_2$; 100 mM HEPES+0.01% Brij buffer. Positive controls contained DMSO with no test compound. Negative controls contained 10 µM staurosporine. The kinase reactions were initiated at time t=0 by the addition of ATP. Kinase reactions were incubated at 21° C. for 40 min, then 20 µl of Kinase-Glo™ reagent were added to each well to quench the kinase reaction and initiate the luminescence reaction. After a 20 min incubation at 21° C., the luminescence was detected in a plate-reading luminometer.

Preparation of Co-Expression Plasmid

A lambda phosphatase co-expression plasmid was constructed as follows.

An open-reading frame for Aurora kinase was amplified from a *Homo sapiens* (human) HepG2 cDNA library (ATCC HB-8065) by the polymerase chain reaction (PCR) using the following primers:

```
Forward primer: TCAAAAAAGAGGCAGTGGGCTTTG

Reverse primer: CTGAATTTGCTGTGATCCAGG.
```

The PCR product (795 base pairs expected) was gel purified as follows. The PCR product was purified by electrophoresis on a 1% agarose gel in TAE buffer and the appropriate size band was excised from the gel and eluted using a standard gel extraction kit. The eluted DNA was ligated for 5 minutes at room temperature with topoisomerase into pSB2-TOPO. The vector pSB2-TOPO is a topoisomerase-activated, modified version of pET26b (Novagen, Madison, Wis.) wherein the following sequence has been inserted into the NdeI site: CATAATGGGCCATCATCATCATCATCACGG TGGTCATATGTCCCTT and the following sequence inserted into the BamHI site: AAGGGGGATCC TAAACTGCAGAGATCC. The sequence of the resulting plasmid, from the Shine-Dalgarno sequence through the "original" NdeI site, the stop site and the "original" BamHI site is as follows: AAGGAGGAGATATACATAATGGG CCATCATCATCATCATCACGGTGGTCATATGT CCCTT [ORF] AAGGGGGATCCTAAACTGCAGAGATCC. The Aurora kinase expressed using this vector has 14 amino acids added to the N-terminus (MetGlyHisHisHisHisHisHisGly GlyHisMetSerLeu) and four amino acids added to the C-terminus (GluGlyGlySer).

The phosphatase co-expression plasmid was then created by inserting the phosphatase gene from lambda bacteriophage into the above plasmid (Matsui T, et al., Biochem. Biophys. Res. Commun., 2001, 284:798-807). The phosphatase gene was amplified using PCR from template lambda bacteriophage DNA (HinDIII digest, New England Biolabs) using the following oligonucleotide primers:

```
Forward primer (PPfor): GCAGAGATCCGAATTCGAGCTC
CGTCGACGGATGGAGTGAAAGAGATGCGC Reverse primer (PPrev): GGTGGTGGTGCTCGAGTGCGGCCGCA
AGCTTTCATCATGCGCCTTCTCCCTGTAC.
```

The PCR product (744 base pairs expected) was gel purified. The purified DNA and non-co-expression plasmid DNA were then digested with SacI and XhoI restriction enzymes. Both the digested plasmid and PCR product were then gel purified and ligated together for 8 h at 16° C. with T4 DNA ligase and transformed into Top10 cells using standard procedures. The presence of the phosphatase gene in the co-expression plasmid was confirmed by sequencing. For standard molecular biology protocols followed here, see also, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

This co-expression plasmid contains both the Aurora kinase and lambda phosphatase genes under control of the lac promoter, each with its own ribosome binding site. By cloning the phosphatase into the middle of the multiple cloning site, downstream of the target gene, convenient restriction sites are available for subcloning the phosphatase into other plasmids. These sites include SacI, SalI and EcoRI between the kinase and phosphatase and HinDIII, NotI and XhoI downstream of the phosphatase.

Protein Kinase Expression

An open-reading frame for c-Abl was amplified from a *Mus musculus* (mouse) cDNA library prepared from freshly harvested mouse liver using a commercially available kit (Invitrogen) by PCR using the following primers:

```
Forward primer: GACAAGTGGGAAATGGAGC

Reverse primer: CGCCTCGTTTCCCCAGCTC.
```

The PCR product (846 base pairs expected) was purified from the PCR reaction mixture using a PCR cleanup kit (Qiagen). The purified DNA was ligated for 5 minutes at room temperature with topoisomerase into pSGX3-TOPO. The vector pSGX3-TOPO is a topoisomerase-activated, modified version of pET26b (Novagen, Madison, Wis.) wherein the following sequence has been inserted into the NdeI site: CATATGTCCCTT and the following sequence inserted into the BamHI site: AAGGGCATCATCACCAT-CACCACTGATCC. The sequence of the resulting plasmid, from the Shine-Dalgarno sequence through the stop site and the BamHI, site is as follows: AAGGAGGA GATATACAT ATGTC CCTT[ORF]AAGGGCATCAT CACCATCACCAC TGATCC. The c-Abl expressed using this vector had three amino acids added to its N-terminus (Met Ser Leu) and 8 amino acids added to its C-terminus (GluGlyHisHisHis HisHisHis).

A c-Abl/phosphatase co expression plasmid was then created by subcloning the phosphatase from the Aurora co-expression plasmid of Example 1 into the above plasmid. Both the Aurora co-expression plasmid and the Abl non-co-expression plasmid were digested 3 hrs with restriction enzymes EcoRI and NotI. The DNA fragments were gel purified and the phosphatase gene from the Aurora plasmid was ligated with the digested c-Abl plasmid for 8 h at 16° C. and transformed into Top 10 cells. The presence of the phosphatase gene in the resulting construct was confirmed by restriction digestion analysis.

This plasmid codes for c-Abl and lambda phosphatase co expression. It has the additional advantage of two unique restriction sites, XbaI and NdeI, upstream of the target gene that can be used for subcloning of other target proteins into this phosphatase co-expressing plasmid.

The plasmid for Abl T3151 was prepared by modifying the Abl plasmid using the Quick Change mutagenesis kit (Stratagene) with the manufacturer's suggested procedure and the following oligonucleotides:

```
Mm05582dS4  5'-CCACCATTCTACATAATCATTGAGTTCATGAC
CTATGGG-3'

Mm05582dA4  5'-CCCATAGGTCATGAACTCAATGATTATGTAGA
ATGGTGG-3'.
```

Protein from the phosphatase co-expression plasmids was purified as follows. The non-co-expression plasmid was transformed into chemically competent BL21 (DE3) Codon+ RIL (Stratagene) cells and the co-expression plasmid was transformed into BL21 (DE3) pSA0145 (a strain that expresses the lytic genes of lambda phage and lyses upon freezing and thawing (Crabtree S, Cronan J E Jr. J Bacteriol 1984 April; 158(1):354-6)) and plated onto petri dishes containing LB agar with kanamycin. Isolated single colonies were grown to mid-log phase and stored at −80° C. in LB containing 15% glycerol. This glycerol stock was streaked on LB agar plates with kanamycin and a single colony was used to inoculate 10 ml cultures of LB with kanamycin and chloramphenicol, which was incubated at 30° C. overnight with shaking. This culture was used to inoculate a 2 L flask containing 500 ml of LB with kanamycin and chloramphenicol, which was grown to mid-log phase at 37° C. and induced by the addition of IPTG to 0.5 mM final concentration. After induction flasks were incubated at 21° C. for 18 h with shaking.

The c-Abl T3151 KD (kinase domain) was purified as follows. Cells were collected by centrifugation, lysed in diluted cracking buffer (50 mM Tris HCl, pH 7.5, 500 mM KCl, 0.1% Tween 20, 20 mM Imidazole, with sonication, and centrifuged to remove cell debris. The soluble fraction was purified over an IMAC column charged with nickel (Pharmacia, Uppsala, Sweden), and eluted under native conditions with a gradient of 20 mM to 500 mM imidazole in 50 mM Tris, pH7.8, 50 mM NaCl, 10 mM methionine, 10% glycerol. The protein was then further purified by gel filtration using a Superdex 75 preparative grade column equilibrated in GF5 buffer (10 mM HEPES, pH7.5, 10 mM methionine, 500 mM NaCl, 5 mM DTT, and 10% glycerol). Fractions containing the purified c-Abl T3151 KD kinase domain were pooled. The protein obtained was 98% pure as judged by electrophoresis on SDS polyacrylamide gels. Mass spectroscopic analysis of the purified protein showed that it was predominantly singly phosphorylated. The protein was then dephosphorylated with Shrimp Alkaline Phosphatase (MBI Fermentas, Burlington, Canada) under the following conditions: 100 U Shrimp Alkaline Phosphatase/mg of c-Abl T3151 KD, 100 mM $MgCl_2$, and 250 mM additional NaCl. The reaction was run overnight at 23° C. The protein was determined to be unphosphorylated by Mass spectroscopic analysis. Any precipitate was spun out and the soluble fraction was separated from reactants by gel filtration using a Superdex 75 preparative grade column equilibrated in GF4 buffer (10 mM HEPES, pH7.5, mM methionine, 150 mM NaCl, 5 mM DTT, and 10% glycerol).

Purification of Met:

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1 L of original culture. One tablet of Roche Complete, EDTA-free protease inhibitor cocktail (Cat# 1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat# 30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat# 10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat# 17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat# 17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat# UFC901024).

Purification of AurA:

The Sf9 insect cell pellets (~18 g) produced from 6 L of cultured cells expressing human Aurora-2 were resuspended in 50 mM Na Phosphate pH 8.0, 500 mM NaCl, 10% glycerol, 0.2% n-octyl-β-D-glucopyranoside (BOG) and 3 mM β-Mercaptoethanol (BME). One tablet of Roche Complete, EDTA-free protease inhibitor cocktail (Cat# 1873580) and 85 units Benzonase (Novagen Cat#70746-3)) were added per 1 L of original culture. Pellets were resuspended in approximately 50 ml per 1 L of original culture and were then sonicated on ice with two 30-45 sec bursts (100% duty cycle). Debris was removed by centrifugation and the supernatant was passed through a 0.8 μm syringe filter before being loaded onto a 5 ml $Ni^{2+}$ HiTrap column (Pharmacia). The column was washed with 6 column volumes of 50 mM Na Phosphate pH 8.0, 500 mM NaCl, 10% glycerol, 3 mM BME. The protein was eluted using a linear gradient of the same buffer containing 500 mM Imidazole. The eluant (24 ml) was cleaved overnight at 4° C. in a buffer containing 50 mM Na Phosphate pH 8.0, 500 mM NaCl, 10% glycerol, 3 mM BME and 10,000 units of TEV (Invitrogen Cat# 10127-017). The protein was passed over a second nickel affinity column as described above; the flow-through was collected. The cleaved protein fractions were combined and concentrated using spin concentrators. Further purification was done by gel filtration chromatography on a S75 sizing column in 50 mM Na Phosphate (pH 8.0), 250 mM NaCl, 1 mM EDTA, 0.1 mM AMP-PNP or ATP buffer, and 5 mM DTT. The cleanest fractions were combined and concentrated to approximately 8-11 mg/ml, and were either flash frozen in liquid nitrogen in 120 μl aliquots and stored at −80° C., or stored at 4° C.

Purification of PDK1:

Cell pellets produced from 6 L of Sf9 insect cells expressing human PDK1 were resuspended in a buffer containing 50 mM Tris-HCl pH 7.7 and 250 mM NaCl in a volume of approximately 40 mL per 1 L of original culture. One tablet of Roche Complete, EDTA-free protease inhibitor cocktail (Cat# 1873580) and 85 units Benzonase (Novagen Cat#70746-3)) were added per 1 L of original culture. The suspension was stirred for 1 hour at 4° C. Debris was removed by centrifugation for 30 minutes at 39,800×g at 4° C. The supernatant was decanted into a 500 mL beaker and 10 ml of a 50% slurry of Qiagen Ni-NTA Agarose (Cat# 30250) that had been pre-equilibrated in 50 mM Tris-HCl pH 7.8, 500 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, and 500 mM Imidazole, sequentially. The 6×Histidine tag was cleaved overnight using 40 units of TEV protease (Invitrogen Cat# 10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat# 17-0409-01) charged with Nickel and equilibrated in 50 mM Tris-HCl pH 7.8, 500 mM NaCl, 10% Glycerol, 10 mM Imidazole, and 10 mM Methionine. The cleaved protein eluted in the flow-through, whereas the uncleaved protein and the His-tag remained bound to the Ni-column. The cleaved protein fractions were combined and concentrated using spin concentrators. Further purification was done by gel filtration chromatography on an Amersham Biosciences HiLoad 16/60 Superdex 200 prep grade (Cat# 17-1069-01) equilibrated in 25 mM Tris-HCl pH 7.5, 150 mM NaCl, and 5 mM DTT. The cleanest fractions were combined and concentrated to 15 mg/ml by centrifugation in an Amicon Ultra-15 10,000 Da MWCO centrifugal filter unit (Cat# UFC901024).

Cell Assays:

MV4-11 and THP cells were maintained in Iscove's Modified Dulbecco's Medium supplemented with 10% fetal bovine serum (FBS) and penicillin/streptomycin, Ba/F3 cells were maintained in RPMI 1640 supplemented with 10% FBS, penicillin/streptomycin and 5 ng/ml recombinant mouse IL-3.

Cell Survival Assays

Compounds were tested in the following assays in duplicate.

96-well XTT assay: Cells were grown in growth media containing various concentrations of compounds (duplicates) on a 96-well plate for 72 hours at 37° C. The starting cell number was 5000-8000 cells per well and volume was 120 μl. At the end of the 72-hour incubation, 40 μl of XTT labeling mixture (50:1 solution of sodium 3'-[1-(phenylamino-carbonyl)-3,4-tetrazolium]-bis(4-methoxy-6-nitro) benzene sulfonic acid hydrate and Electron-coupling reagent: PMS (N-methyl dibenzopyrazine methyl sulfate) were added to each well of the plate. After an additional 2-6 hours of incubation at 37° C., the absorbance reading at 405 nm with background correction at 650 nm was measured with a spectrophotometer.

384-well AlamarBlue assay: 90 l of cell suspension were plated onto each well of a 384-well plate preprinted with 0.5 μl of compound in DMSO or DMSO only. The starting cell number was 4000 cells per well. After a 72-hour incubation, 10 μl of AlamarBlue solution (440 μM resazurin in PBS) were then added to each well of the plate. After an additional 2-hour incubation at 37° C., fluorescence was measured using a TECAN plate reading fluorometer with excitation at 535 nm and emission at 591 nm.

BCR-ABL Phospho-ELISA Assay

The following table shows the reagents that were typically used in the BCR-ABL phospho-ELISA ("P-ELISA") assay.

TABLE 19

BCR-ABL phospho-ELISA(p-ELISA) Typical Reagent List

| Description | Vendor | Catalog # |
|---|---|---|
| RPMI 1640 | Invitrogen | 11875-135 |
| 10% Fetal Bovine Serum, characterized, heat inactivated | VWR | 16777-014 |
| Human Plasma, Anticoagulant = EDTA | Bioreclamation Inc. | HMPLEDTA |
| c-Abl (Ab-3) monoclonal antibody | VWR | 80001-286 |
| Recombinant Mouse Interleukin-3 | Chemicon | IL015 |
| Adhesive Plate Seals | | |
| 96well PP 325 μl round bottom plate w/lid TC | Thompson Instrument Co | 932465 |
| 96well Nunc Maxisorp plate (for colorimetric assay) | Fisher Scientific | 12-565-136 |
| 96well white flat-bottom plate (for luminescent assay) | Matrix | 4923 |
| Lysis buffer components | | |
| Tris-Cl pH 7.4 (20 mM) | | |
| NP-40 (1%) | | |
| EDTA (5 mM) | | |
| Sodium pyrophosphate (NaPP; 5 mM) | | |
| NaF (5 mM) | | |
| NaCl (150 mM) | | |
| Protease Inhibitor Cocktail | Sigma | P2714 |
| PMSF (1 mM) | | |
| Sodium vanadate (NaVO$_4$; 2 mM) | | |
| PBS, ice cold | | |
| Anti-Phosphotyrosine (4G10 ™), HRP conjugate or unconjugated | Upstate | 16-105 or 05-321 |
| Goat Anti-Mouse IgG, HRP conjugate (if unconjugated 4G10 is used) | Upstate | 12-349 |
| BD OptEIA Reagent Set B Coating Buffer (0.1M Na-carbonate, pH 9.5) Assay Diluent Wash buffer (.05% Tween/PBS) Stop Solution (2N sulfuric acid) Substrate Reagents A&B | BD Biosciences | 550534 |

TABLE 19-continued

BCR-ABL phospho-ELISA(p-ELISA) Typical Reagent List

| Description | Vendor | Catalog # |
|---|---|---|
| SuperSignal ELISA Pico Chemiluminescent Substrate (may be used instead of Substrate Reagents A&B) | Pierce | 37070 |

Cells (Ba/F$_3$ cells transfected with WT BCR-ABL, other kinases, or T315I, Y253F, or other mutant forms of BCR-ABL) were grown in the absence of IL-3 at least ½ week before the assay. The day before assay, the cells were fed with fresh media so that at the time of assay the cells were in log phase. Ba/F3 cells that had been grown in the absence of IL-3 for at least ½ week were resuspended in RPMI 1640 so that each well of a 96-well plate would contain approximately 200,000 cells. Cells were distributed in a 96-well plate containing serially diluted concentrations of test compounds. Cells were typically incubated with or without test compounds for 60-120 minutes at 5% CO$_2$, 37° C. The incubation was performed with or without other additives such as 10% FCS or 50% human plasma. After incubation of compounds, lysis buffer was added and incubated for 10-15 minutes; the lysate was cleared by centrifugation.

To make the ELISA plate, commercially available Anti-ABL antibodies (e.g. (Ab-3, Calbiochem OP20) were prepared at a concentration of 0.125 μg/ml in coating buffer (0.1M Na-carbonate, pH 9.5), and plated at 10 ml per plate (12.5 μl 100 μg/ml Ab/10 ml). In a high binding multi-well plate, 100 μl Ab in coating buffer were added to each well, and each plate was covered with a plate seal and incubated overnight at 4° C.

Excess antibody was removed and the ELISA plate was washed 3-4 times with 200 μl of wash buffer (0.05% Tween in PBS, pH 7.4). 150 μl of lysate (see above) were transferred to the ELISA plate. Plates were sealed and incubated 2 hours at room temperature. The detection antibody (e.g. HRP conjugated anti-pTyr or unconjugated α-p-Y 4G10, Upstate) was prepared in assay diluent. The antibody was diluted 1:1000 (stock=2 μg/μl, 200 μg in 100 μl; f.c.=2 μg/ml) in assay diluent and 10 ml of diluted antibody per plate were added. The lysate was removed from the ELISA plates, and wells were washed four times with 200 μl of wash buffer per well. 100 μl of detection antibody was added to each well; the plate was covered, and incubated 1 hr at room temperature (21° C.). Excess detection antibody was removed from the ELISA plates, and the wells were washed four times with 200 μl of wash buffer per well.

If necessary, (i.e. for unconjugated anti-pTyr antibody) secondary antibody (goat anti-rabbit HRP) was diluted 1:3000 in assay diluent (3.33 μl per 10 ml diluent) and added at 10 ml of diluted antibody per plate. Excess secondary antibody was removed from the ELISA plate, and the plate was washed four times with 200 μl per well of wash buffer.

Substrate Reagent A and Substrate Reagent B (Pierce Cat#37070 SuperSignal ELISA Pico Chemiluminescent Substrate) were added immediately before use (10 ml resultant solution per plate). 100 μl substrate were added per well, mixed for 1 minute, and chemiluminescent signal was measured with a luminometer.

TABLE 20

Selected assay results:

| compound | Abl_T315I_ OP IC50 | Abl_Y393F IC50 | P_ELISA_[T315I_Cells] or Ba/F3 T315I proliferation (XTT) | AurA IC50 | MET IC50 | PDK1 IC50 |
|---|---|---|---|---|---|---|
| 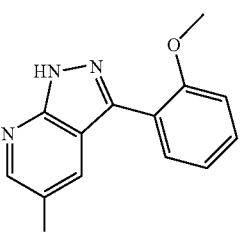 | C | C | B | | | |
| 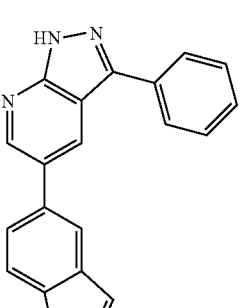 | C | C | B | | | |

TABLE 20-continued
Selected assay results:
| compound | Abl_T315I_ 0P IC50 | Abl_Y393F IC50 | P_ELISA_[T 315I_Cells] or Ba/F3 T315I proliferation (XTT) | AurA IC50 | MET IC50 | PDK1 IC50 |
|---|---|---|---|---|---|---|
| 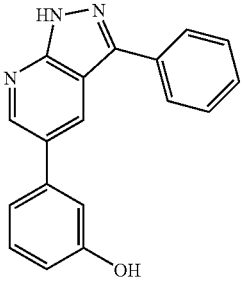 | C | C | C | | | |
| 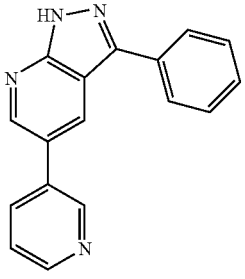 | C | C | A | | | |
| 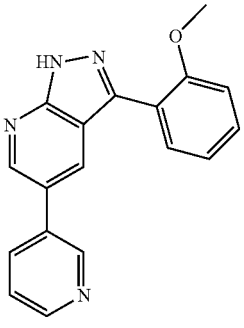 | C | C | B | | | |
| 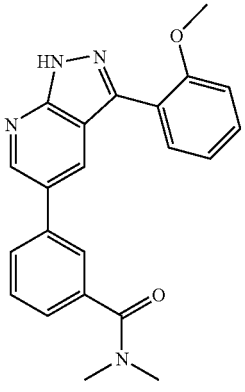 | C | C | C | | | |

TABLE 20-continued
Selected assay results:
| compound | Abl_T315I_ 0P IC50 | Abl_Y393F IC50 | P_ELISA_[T 315I_Cells] or Ba/F3 T315I proliferation (XTT) | AurA IC50 | MET IC50 | PDK1 IC50 |
|---|---|---|---|---|---|---|
| 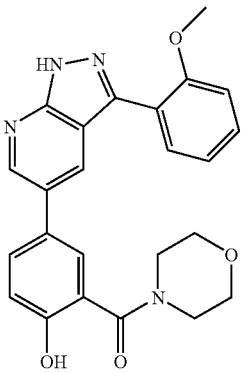 | C | C | C | | | |
| 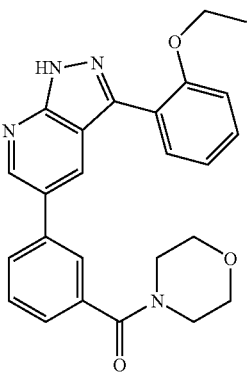 | C | C | B | | | |
| 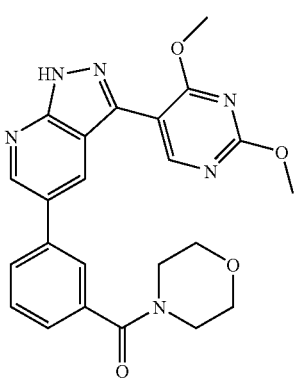 | C | C | B | | | |

TABLE 20-continued
Selected assay results:
| compound | Abl_T315I_OP IC50 | Abl_Y393F IC50 | P_ELISA_[T315I_Cells] or Ba/F3 T315I proliferation (XTT) | AurA IC50 | MET IC50 | PDK1 IC50 |
|---|---|---|---|---|---|---|
| 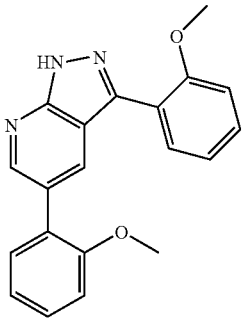 | C | C | B | | | |
| 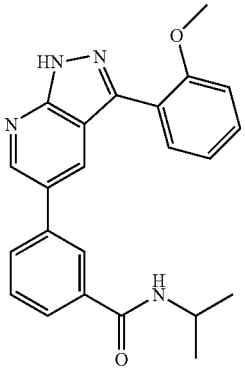 | C | C | B | | | |
| 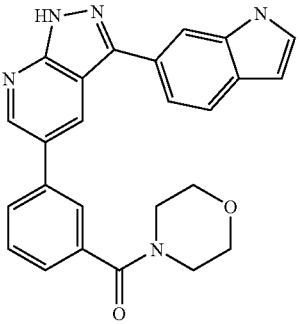 | C | C | B | | | |
| 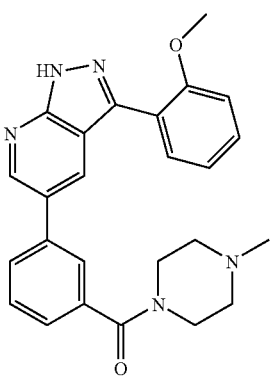 | C | C | C | | | |

TABLE 20-continued

Selected assay results:

| compound | Abl_T315I_0P IC50 | Abl_Y393F IC50 | P_ELISA_[T315I_Cells] or Ba/F3 T315I proliferation (XTT) | AurA IC50 | MET IC50 | PDK1 IC50 |
|---|---|---|---|---|---|---|
| *[3-(3-ethylphenyl)-1H-pyrazolo[3,4-b]pyridin-5-yl]phenyl morpholinyl ketone* | C | C | C | | | |
| *[3-(4-fluoro-2-methylphenyl)-1H-pyrazolo[3,4-b]pyridin-5-yl]phenyl morpholinyl ketone* | C | C | B | | | |
| *[3-(3-fluoro-2-methoxyphenyl)-1H-pyrazolo[3,4-b]pyridin-5-yl]phenyl morpholinyl ketone* | C | C | C | | | |
| *[3-(3-methylthiophen-2-yl)-1H-pyrazolo[3,4-b]pyridin-5-yl]phenyl morpholinyl ketone* | C | C | C | | | |

TABLE 20-continued

| | Selected assay results: | | | | | |
|---|---|---|---|---|---|---|
| compound | Abl_T315I_ 0P IC50 | Abl_Y393F IC50 | P_ELISA_[T 315I_Cells] or Ba/F3 T315I proliferation (XTT) | AurA IC50 | MET IC50 | PDK1 IC50 |
| *structure* | C | C | C | | | |
| *structure* | C | C | C | | | |
| *structure* | C | C | B | | | |
| *structure* | C | C | B | | | |

TABLE 20-continued

Selected assay results:

| compound | Abl_T315I_ 0P IC50 | Abl_Y393F IC50 | P_ELISA_[T 315I_Cells] or Ba/F3 T315I proliferation (XTT) | AurA IC50 | MET IC50 | PDK1 IC50 |
|---|---|---|---|---|---|---|
| *(structure)* | C | C | C | | | |
| *(structure)* | C | C | B | | B | |
| *(structure)* | C | C | C | | | |

TABLE 20-continued

Selected assay results:

| compound | Abl_T315I_OP IC50 | Abl_Y393F IC50 | P_ELISA_[T315I_Cells] or Ba/F3 T315I proliferation (XTT) | AurA IC50 | MET IC50 | PDK1 IC50 |
|---|---|---|---|---|---|---|
| [structure] | C | C | B | | | |
| [structure] | C | C | C | | | |
| [structure] | C | C | C | | | |

TABLE 20-continued
Selected assay results:
| compound | Abl_T315I_ OP IC50 | Abl_Y393F IC50 | P_ELISA_[T 315I_Cells] or Ba/F3 T315I proliferation (XTT) | AurA IC50 | MET IC50 | PDK1 IC50 |
|---|---|---|---|---|---|---|
| 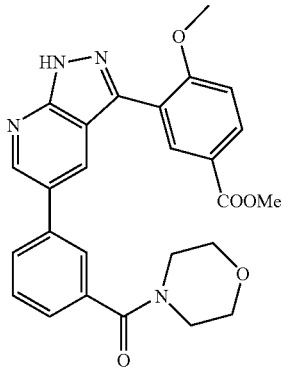 | C | C | A | C | | |
| 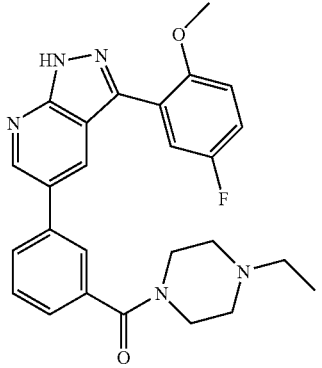 | C | C | C | | B | |
| 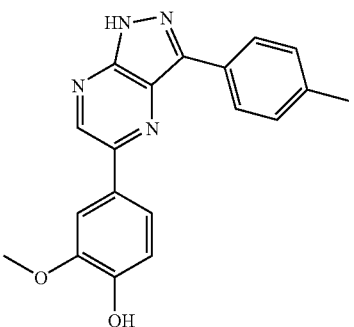 | C | C | C | | B | |

TABLE 20-continued
| | Selected assay results: | | | | | |
|---|---|---|---|---|---|---|
| compound | Abl_T315I_ 0P IC50 | Abl_Y393F IC50 | P_ELISA_[T 315I_Cells] or Ba/F3 T315I proliferation (XTT) | AurA IC50 | MET IC50 | PDK1 IC50 |
| 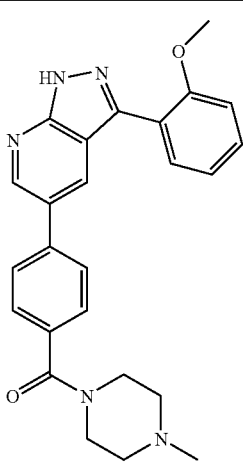 | C | C | C | | | B |
| 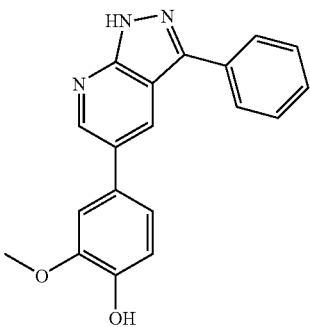 | C | C | B | | | B |
| 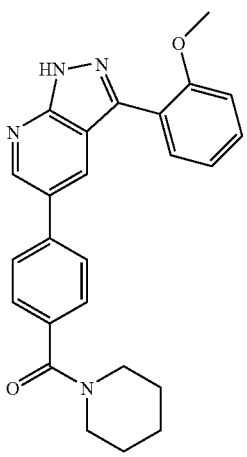 | C | B | | | | B |

TABLE 20-continued

Selected assay results:

| compound | Abl_T315I_0P IC50 | Abl_Y393F IC50 | P_ELISA_[T315I_Cells] or Ba/F3 T315I proliferation (XTT) | AurA IC50 | MET IC50 | PDK1 IC50 |
|---|---|---|---|---|---|---|
| 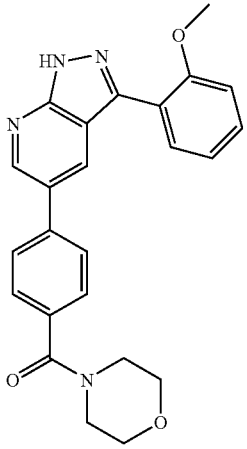 | C | C | B | | | B |
| 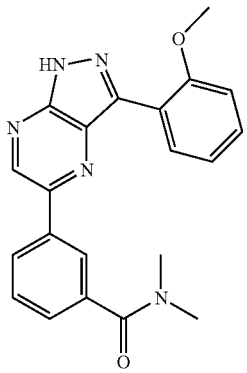 | C | C | A | | | |

For Table 21 above, the activity symbols represent an IC50 as follows: A>10 μM; B=1-10 μM; C<1 μM.

---

What is claimed is:

1. A method of inhibiting the activity of a protein kinase comprising contacting said protein kinase with a compound having the formula:

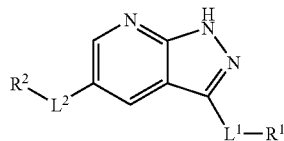

wherein

L$^1$ and L$^2$ are independently a bond, —S(O)$_n$—, —O—, —NH—, unsubstituted C$_1$-C$_5$ alkylene, or unsubstituted 2 to 5 membered heteroalkylene, wherein n is an integer from 0 to 2, and R$^1$ and R$^2$ are independently substituted or unsubstituted cycloalkyl, substituted or unsubstituted heterocycloalkyl, substituted or unsubstituted heteroaryl, or substituted or unsubstituted aryl;

with the proviso that R$^1$ is not substituted or unsubstituted pyrrolyl, and that L$^1$ is not unsubstituted 2 to 5 membered heteroalkylene when R$^1$ and R$^2$ are both unsubstituted phenyl, and that L$^1$ is not —S(O)$_2$— when R$^2$ is unsubstituted piperazinyl, and that R$^1$ is not substituted or unsubstituted isoxazolyl when R$^2$ is unsubstituted pyridinyl.

2. The method of claim 1, wherein said protein kinase is an Abelson tyrosine kinase, Ron receptor tyrosine kinase, Met receptor tyrosine kinase, Fms-like tyrosine kinase-3, Aurora kinases, p21-activated kinase-4, or 3-phosphoinositide-dependent kinase-1.

3. The method of claim 1, wherein said protein kinase is a Bcr-Abl kinase having a mutation selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V3791, F382L, L387M, H396P, H396R, S417Y, E459K and F486S.

4. The method of claim 3, wherein said protein kinase has a T315I mutation.

5. A pharmaceutical composition comprising one or more pharmaceutically acceptable excipients and a compound having the formula:

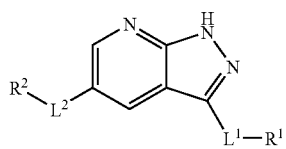

wherein
L$^1$ and L$^2$ are independently a bond, —S(O)$_n$—, —O—, —NH—, unsubstituted C$_1$-C$_5$ alkylene, or unsubstituted 2 to 5 membered heteroalkylene, wherein n is an integer from 0 to 2, and R$^1$ and R$^2$ are independently substituted or unsubstituted cycloalkyl, substituted or unsubstituted heterocycloalkyl, substituted or unsubstituted heteroaryl, or substituted or unsubstituted aryl;
with the proviso that R$^1$ is not substituted or unsubstituted pyrrolyl, and that L$^1$ is not unsubstituted 2 to 5 membered heteroalkylene when R$^1$ and R$^2$ are both unsubstituted phenyl, and that L$^1$ is not —S(O)$_2$— when R$^2$ is unsubstituted piperazinyl, and that R$^1$ is not substituted or unsubstituted isoxazolyl when R$^2$ is unsubstituted pyridinyl.

6. The method of claim 1, wherein L$^1$ and L$^2$ are independently a bond, —S(O)$_n$—, —O—, —NH—, or unsubstituted C$_1$-C$_5$ alkylene.

7. The method of claim 1, wherein L$^1$ and L$^2$ are a bond.

8. The method of claim 1, wherein L$^1$ or L$^2$ is a bond.

9. The method of claim 1, wherein R$^1$ is substituted or unsubstituted cycloalkyl, substituted or unsubstituted heterocycloalkyl, substituted or unsubstituted 5 or 6 membered heteroaryl, or substituted or unsubstituted aryl.

10. The method of claim 1, wherein R$^1$ is substituted or unsubstituted 6 membered heteroaryl, or substituted or unsubstituted aryl.

11. The method of claim 1, wherein R$^1$ is
(1) unsubstituted C$_3$-C$_7$ cycloalkyl;
(2) unsubstituted 3 to 7 membered heterocycloalkyl;
(3) unsubstituted heteroaryl;
(4) unsubstituted aryl;
(5) substituted C$_3$-C$_7$ cycloalkyl;
(6) substituted 3 to 7 membered heterocycloalkyl;
(7) substituted aryl; or
(8) substituted heteroaryl;
wherein
(5) and (6) are substituted with an oxo, —OH, —CF$_3$, —COOH, cyano, halogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, R$^{12}$-substituted or unsubstituted heteroaryl, -L$^{12}$-C(X$^1$)R$^7$, -L$^{12}$-OR$^8$, -L$^{12}$-NR$^{91}$R$^{92}$, or -L$^{12}$-S(O)$_m$R$^{10}$, (7) and (8) are substituted with an —OH, —CF$_3$, —COOH, cyano, halogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$_{11}$-substituted or unsubstituted 3 to 7 membered heterocycloalkyl, R$^{12}$-substituted or unsubstituted aryl, R$^{12}$-substituted or unsubstituted heteroaryl, -L$^{12}$-C(X$^1$)R$^7$, -L$^{12}$-OR$^8$, -L$^{12}$-NR$^{91}$R$^{92}$, or L$^{12}$S(O)$_m$R$^{10}$, wherein (a) X$^1$ is =S, =O, or =NR$^{15}$, wherein R$^{15}$ is H, —OR$^{151}$, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, or R$^{12}$-substituted or unsubstituted heteroaryl, wherein R$^{151}$ is hydrogen or R$^{11}$-substituted or unsubstituted C$_1$-C$_{10}$ alkyl, (b) m is an integer from 0 to 2;

(c) R$^7$ is hydrogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, R$^{12}$-substituted or unsubstituted heteroaryl, —OR$^{71}$, or —NR$^{72}$R$^{73}$, wherein R$^{71}$, R$^{72}$, and R$^{73}$ are independently hydrogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, or R$^{12}$-substituted or unsubstituted heteroaryl, wherein R$^{72}$ and R$^{73}$ are optionally joined with the nitrogen to which they are attached to form an R$^{11}$-substituted or unsubstituted 3 to 7 membered heterocycloalkyl, or R$^{12}$-substituted or unsubstituted heteroaryl;

(d) R$^8$, R$^{91}$ and R$^{92}$ are independently hydrogen, —CF$_3$, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, R$^{12}$-substituted or unsubstituted heteroaryl, —C(X$^2$)R$^{81}$, or —S(O)$_w$R$^{81}$, wherein R$^{91}$ and R$^{92}$ are optionally joined with the nitrogen to which they are attached to form an R$^{11}$-substituted or unsubstituted 3 to 7 membered heterocycloalkyl, or R$^{12}$-substituted or unsubstituted heteroaryl, wherein (i) X$^2$ is =S, =O, or =NR$^{16}$, wherein R$^{16}$ is R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, or R$^{12}$-substituted or unsubstituted heteroaryl;

(ii) w is an integer from 0 to 2, and (iii) R$^{81}$ is hydrogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, R$^{12}$-substituted or unsubstituted heteroaryl, or —NR$^{811}$R$^{812}$, wherein R$^{811}$ and R$^{812}$ are independently hydrogen, R1$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, or R$^{12}$-substituted or unsubstituted heteroaryl, wherein R$^{811}$ and R$^{812}$ are optionally joined with the nitrogen to which they are attached to form an R$^{11}$-substituted or unsubstituted 3 to 7 membered heterocycloalkyl, or R$^{12}$-substituted or unsubstituted heteroaryl;

(e) R$^{10}$ is hydrogen, R$^{11}$-substituted or unsubstituted C$_1$-C$_{10}$ alkyl, R$^{11}$-substituted or unsubstituted 2 to 10 membered heteroalkyl, R$^{11}$-substituted or unsubstituted C$_3$-C$_7$ cycloalkyl, R$^{11}$-substituted or unsubstituted 3 to 7 membered heterocycloalkyl, R$^{12}$-substituted or unsubstituted aryl, R$^{12}$-substituted or unsubstituted heteroaryl, or —NR$^{101}$R$^{102}$, wherein (i) R$^{101}$ and R$^{102}$ are independently hydrogen, R$^{11}$-substituted or unsubstituted C$_1$-C$_{10}$ alkyl, R$^{11}$-substituted or unsubstituted 2 to 10 membered heteroalkyl, $R^{11}$-substituted or unsubstituted $C_3$-$C_7$ cycloalkyl, $R^{11}$-substituted or unsubstituted 3 to 7 membered heterocycloalkyl, $R^{12}$-substituted or unsubstituted aryl, or $R^{12}$-substituted or unsubstituted heteroaryl, wherein $R^{101}$ and $R^{102}$ are optionally joined with the nitrogen to which they are attached to form an $R^{11}$-substituted or unsubstituted 3 to 7 membered heterocycloalkyl, or $R^{12}$-substituted or unsubstituted heteroaryl;

(f) $L^{12}$ is a bond, unsubstituted $C_1$-$C_{10}$ alkylene, or unsubstituted heteroalkylene;

(g) $R^{11}$ is oxo, —OH, —COOH, —$CF_3$, —$OCF_3$, —CN, amino, halogen, $R^{13}$-substituted or unsubstituted 2 to 10 membered alkyl, $R^{13}$-substituted or unsubstituted 2 to 10 membered heteroalkyl, $R^{13}$-substituted or unsubstituted $C_3$-$C_7$ cycloalkyl, $R^{13}$-substituted or unsubstituted 3 to 7 membered heterocycloalkyl, $R^{14}$-substituted or unsubstituted aryl, or $R^{14}$-substituted or unsubstituted heteroaryl;

(h) $R^{12}$ is —OH, —COOH, amino, halogen, —$CF_3$, —$OCF_3$, —CN, $R^{13}$-substituted or unsubstituted 2 to 10 membered alkyl, $R^{13}$-substituted or unsubstituted 2 to 10 membered heteroalkyl, $R^{13}$-substituted or unsubstituted $C_3$-$C_7$ cycloalkyl, $R^{13}$-substituted or unsubstituted 3 to 7 membered heterocycloalkyl, $R^{14}$-substituted or unsubstituted aryl, or $R^{14}$-substituted or unsubstituted heteroaryl;

(i) $R^{13}$ is oxo, —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl; and (j) $R^{14}$ is —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

12. The method of claim 1, wherein $R^1$ is substituted or unsubstituted 6 membered heteroaryl, or substituted or unsubstituted aryl.

13. The method of claim 1, wherein $L^1$ is a bond.

14. The method of claim 11, wherein $R^1$ is (7) or (8), wherein (7) and (8) are substituted with an —OH, —$CF_3$, halogen, unsubstituted $C_1$-$C_{10}$ alkyl, unsubstituted 2 to 10 membered heteroalkyl, unsubstituted $C_3$-$C_7$, cycloalkyl, unsubstituted 3 to 7 membered heterocycloalkyl, unsubstituted aryl, unsubstituted heteroaryl, or -$L^{12}$-$OR^8$, wherein $L^{12}$ is a bond.

15. The method of claim 14, wherein $R^8$ is $CF_3$.

16. The method of claim 11, wherein $R^1$ is (7) or (8), wherein (7) and (8) are substituted with an —$OCH_3$, —$OCF_3$, —$CH_3$, —$CF_3$, —$OCH_2CH_3$, halogen, or cyclopropyloxy.

17. The method of claim 11 wherein $L^1$ and $L^2$ are a bond.

18. The method of claim 1, wherein $R^2$ is (1) unsubstituted $C_3$-$C_7$ cycloalkyl;
(2) unsubstituted 3 to 7 membered heterocycloalkyl;
(3) unsubstituted heteroaryl;
(4) unsubstituted aryl;
(5) substituted $C_3$-$C_7$ cycloalkyl;
(6) substituted 3 to 7 membered heterocycloalkyl;
(7) substituted aryl; or
(8) substituted heteroaryl;
wherein (5) and (6) are substituted with an oxo, —OH, —$CF_3$, —COOH, cyano, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, -$L^{22}$-$C(X^3)R^3$, -$L^{22}$-$OR^4$, -$L^{22}$-$NR^{51}R^{52}$, or -$L^{22}S(O)_qR^6$, (7) and (8) are substituted with an —OH, —$CF_3$, —COOH, cyano, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, -$L^{22}$-$C(X^3)R^3$, -$L^{22}OR^4$, -$L^{22}$-$NR^{51}R^{52}$, or -$L^{22}S(O)_qR^6$, wherein (a) $X_3$ is S, =O, or =$NR^{17}$, wherein $R^{17}$ is H, —$OR^{171}$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{171}$ is H or $R^{21}$-substituted or unsubstituted $C_1$-$C_{10}$ alkyl;

(b) q is an integer from 0 to 2;

(c) $R^3$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$OR^{31}$, or —$NR^{32}R^{33}$, wherein (i) $R^{31}$, $R^{32}$, and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl;

(d) $R^4$, $R^{51}$ and $R^{52}$ are independently hydrogen, —$CF_3$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$C(X^4)R^{41}$, or —$S(O)_vR^{41}$, wherein $R^{51}$ and $R^{52}$ are optionally joined with the nitrogen to which they are attached to form an $R^{21}$-substituted or unsubstituted 3 to 7 membered heterocycloalkyl, or $R^{22}$-substituted or unsubstituted heteroaryl, wherein (ii) $X^4$ is =S, =O, or =$NR^{18}$, wherein $R^{18}$ is $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl;

(ii) v is an integer from 0 to 2;

(iii) $R^{41}$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —$NR^{411}R^{412}$, wherein $R^{411}$ and $R^{412}$ are independently selected from hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{411}$ and $R^{412}$ are optionally joined with the nitrogen to which they are attached to form an $R^{21}$-substituted or unsubstituted 3 to 7 membered heterocycloalkyl, or $R^{22}$-substituted or unsubstituted heteroaryl;

(e) $R^6$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$, cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —$NR^{61}R^{62}$, wherein (i) $R^{61}$ and $R^{62}$ are hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{61}$ and $R^{62}$ are optionally joined with the nitrogen to which they are attached to form an $R^{21}$-substituted or unsubstituted 3 to 7 membered heterocycloalkyl, or $R^{22}$-substituted or unsubstituted heteroaryl;

(f) $L^{22}$ is a bond, unsubstituted $C_1$-$C_{10}$ alkylene or unsubstituted heteroalkylene;

(g) $R^{21}$ is oxo, —OH, —COOH, —$CF_3$, —$OCF_3$, —CN, amino, halogen, $R^{23}$-substituted or unsubstituted 2 to 10 membered alkyl, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl;

(h) $R^{22}$ is —OH, —COOH, amino, halogen, —$CF_3$, —$OCF_3$, —CN, $R^{23}$-substituted or unsubstituted 2 to 10 membered alkyl, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl;

(i) $R^{23}$ is oxo, —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl; and (j) $R^{24}$ is —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

19. The method of claim 18, wherein $L^2$ is a bond.

20. The method of claim 18, wherein $R^2$ is (3), (4), (7), or (8).

21. The method of claim 19, wherein $R^2$ is (7) or (8).

22. The method of claim 21, wherein (7) and (8) are substituted with an -$L^{22}$-$C(X^3)R^3$, -$L^{22}$-$OR^4$, -$L^{22}$-$NR^{51}R^{52}$, -$L^{22}C(NH)NR^{32}R^{33}$, or -$L^{22}$-$S(O)_qR^6$.

23. The method of claim 22, wherein
$R^3$ is —$NR^{32}R^{33}$;
$X^3$ is =O or =$NR^{17}$;
$R^6$ is —$NR^{61}R^{62}$;
$R^{51}$ is —$C(O)R^{41}$ or —$S(O)_vR^{41}$.

24. The method of claim 23, wherein $R^{41}$ is —$NR^{411}R^{412}$.

25. The method of claim 19, wherein $R^2$ is (7) or (8), wherein (7) and (8) are substituted with —OH, —$CF_3$, —COOH, amino, halogen, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, or -$L^{22}$-$C(X^3)R^3$, wherein
$X^3$ is =O;
$R^3$ is unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, or —$NR^{32}R^{33}$, wherein
$R^{32}$ and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl.

26. The method of claim 19, wherein $R^2$ is (7) or (8), wherein (7) and (8) are substituted with unsubstituted 2 to 10 membered heteroalkyl, or -$L^{22}$-$C(O)R^3$, wherein
$L^{22}$ is a bond; and
$R^3$ is —$NR^{32}R^{33}$, wherein
$R^{32}$ and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$, cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, wherein $R^{32}$ and $R^{33}$ are optionally joined with the nitrogen to which they are attached to form an $R^{21}$-substituted or unsubstituted 3 to 7 membered heterocycloalkyl, or $R^{22}$-substituted or unsubstituted heteroaryl.

27. The method of claim 1, wherein $R^1$ is a substituted or unsubstituted fused ring aryl or substituted or unsubstituted fused ring heteroaryl.

28. The method of claim 1, wherein $R^2$ is substituted or unsubstituted indolyl, substituted or unsubstituted quinolinyl, or substituted or unsubstituted benzodioxolyl.

29. The method of claim 1, wherein $R^2$ is a substituted or unsubstituted fused ring aryl or substituted or unsubstituted fused ring heteroaryl.

30. The method of claim 1, wherein $R^2$ is substituted or unsubstituted indolyl, substituted or unsubstituted quinolinyl, or substituted or unsubstituted benzodioxolyl.

31. The method of claim 1, wherein $R^1$ and $R^2$ are independently substituted or unsubstituted hydantoinyl, substituted or unsubstituted dioxolanyl, substituted or unsubstituted dioxanyl, substituted or unsubstituted trioxanyl, substituted or unsubstituted tetrahydrothienyl, substituted or unsubstituted tetrahydrofuranyl, substituted or unsubstituted tetrahydrothiophenyl, substituted or unsubstituted tetrahydropyranyl, substituted or unsubstituted tetrahydrothiopyranyl, substituted or unsubstituted pyrrolidinyl, substituted or unsubstituted morpholino, substituted or unsubstituted piperidinyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyridyl, substituted or unsubstituted pyrazyl, substituted or unsubstituted pyrimidyl, substituted or unsubstituted pyridazinyl, substituted or unsubstituted thiazolyl, substituted or unsubstituted isothioazolyl, substituted or unsubstituted triazolyl, substituted or unsubstituted thienyl, substituted or unsubstituted triazinyl, substituted or unsubstituted thiadiazolyl, or substituted or unsubstituted tetrazolyl.

32. The method of claim 7, wherein $R^1$ and $R^2$ are independently substituted or unsubstituted aryl.

33. The method of claim 32, wherein $R^1$ and $R^2$ are independently substituted or unsubstituted phenyl.

34. The method of claim 33, wherein $R^1$ and $R^2$ are each substituted phenyl.

35. The method of claim 34, wherein the substituents are selected from halogen, $C_1$-$C_3$ unsubstituted alkyl, —C(=O)NR$^{72}$R$^{73}$, —OR$^8$ and —NR$^{91}$R$^{92}$.

* * * * *